United States Patent [19]

Rody et al.

[11] Patent Number: 5,059,689

[45] Date of Patent: Oct. 22, 1991

[54] TETRAMETHYLPIPERIDINO-S-TRIAZINES

[75] Inventors: Jean Rody, Riehen; Gerhard Rytz, Schwarzenburg; Mario Slongo, Tafers, all of Switzerland

[73] Assignee: Ciba-Geigy Corporation, Ardsley, N.Y.

[21] Appl. No.: 303,217

[22] Filed: Jan. 30, 1989

[30] Foreign Application Priority Data

Feb. 8, 1988 [CH] Switzerland ............................ 440/88

[51] Int. Cl.$^5$ .................. C07D 279/12; C07D 403/06; C07D 401/06; C07D 403/12

[52] U.S. Cl. .......................................... 544/6; 544/70; 544/113; 544/198; 544/209; 544/212; 252/401; 252/402; 252/403; 524/100; 106/287.21; 430/614

[58] Field of Search ............... 544/198, 209, 212, 113, 544/6, 70

[56] References Cited

U.S. PATENT DOCUMENTS

| | | | |
|---|---|---|---|
| 3,382,221 | 6/1966 | Petropoulos et al. | 544/198 |
| 3,576,805 | 4/1971 | Cantrall et al. | 544/198 |
| 3,925,376 | 12/1975 | Chalmers et al. | 544/198 |
| 4,033,957 | 7/1977 | Hofer et al. | 544/198 |
| 4,086,204 | 4/1978 | Cassandrini et al. | 544/198 |
| 4,108,829 | 8/1978 | Cassandrini et al. | 544/198 |
| 4,407,993 | 10/1983 | Hinsken et al. | 544/198 |
| 4,629,752 | 12/1986 | Layer et al. | 544/198 |
| 4,692,486 | 9/1987 | Gugumus | 544/198 |
| 4,696,961 | 9/1987 | Cantatore | 544/198 |
| 4,707,507 | 11/1987 | Akutsu et al. | 544/198 |
| 4,722,806 | 2/1988 | Lai et al. | 544/198 |
| 4,816,507 | 3/1989 | Cantatore et al. | 544/198 |

FOREIGN PATENT DOCUMENTS

0165608 12/1985 European Pat. Off. .

OTHER PUBLICATIONS

C.A., vol. 99, No. 39335g (1983).

*Primary Examiner*—Johann Richter
*Attorney, Agent, or Firm*—JoAnn Villamizar

[57] ABSTRACT

Compounds which contain at least one group of the formula I

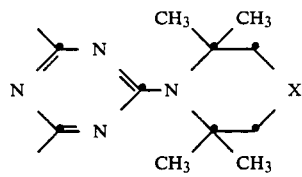

in which X is a group which completes the ring to form a piperidine ring, are effective stabilizers for organic materials against damage by light, oxygen and heat.

18 Claims, No Drawings

TETRAMETHYLPIPERIDINO-S-TRIAZINES

The invention relates to new triazine derivatives which contain at least one tetramethylpiperidino group and their use as stabilizers for organic materials.

Compounds which contain at least one triazine group and one 2,2,6,6-tetramethyl-4-piperidinyl group in their molecule are known as stabilizers for organic materials. Such compounds either contain only one triazine group, for example the compounds described in U.S. Pat. No. 3,925,376, or they contain a number of triazine groups, for example the compounds described in U.S. Pat. No. 4,108,829. They can also be oligomers or polymers having a recurring triazine group, for example the compounds described in U.S. Pat. No. 4,086,204. In all these known compounds, the piperidine radical is linked with the triazine ring via its 4-position.

Compounds have now been found in which the 2,2,6,6-tetramethylpiperidine radical is bonded to the triazine ring via its 1-position (the nitrogen atom). Two such compounds are described in DE-A-2,025,080 and were proposed as medicaments therein. Use as stabilizers is not mentioned.

The invention relates to compounds which contain at least one group of the formula I

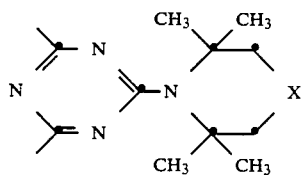

where X is a group which completes the ring to form a piperidine ring, with the exception of 2-(2,2,6,6-tetramethyl-1-piperidino)-4,6-bis(2,4,4-trimethyl-2-pentylamino)-triazine and 2,4-dichloro-6-(2,2,6,6-tetramethyl-1-piperidino)-triazine.

Compounds are preferred here which contain at least one group of the formula I, in which X is not $CH_2$. Such groups may be present in the most diverse classes of compounds. The most important compound classes according to the invention are the following 1) compounds of the formula II

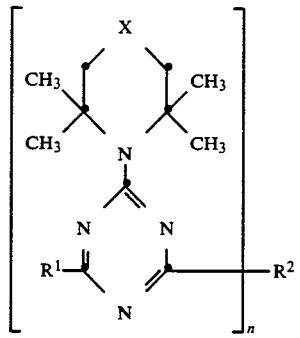

in which n is an integer from 1 to 6, $R^1$ is a radical of the formula

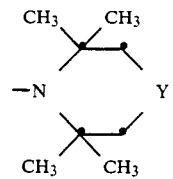

or Cl, OH, $-OR^3$, $-SR^3$ or $-NR^4R^5$, where $R^3$ is $C_1$-$C_{18}$alkyl, allyl, cyclohexyl, benzyl, phenyl or a group of the formula A

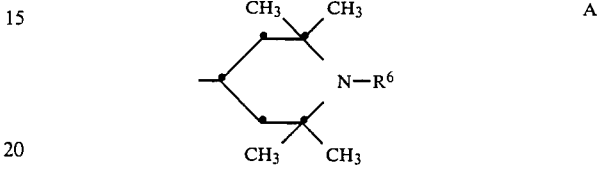

$R^4$ is hydrogen, $C_1$-$C_{12}$alkyl, 2-hydroxyethyl, allyl, cyclohexyl, benzyl or a group of the formula A, $R^5$ is $C_1$-$C_{12}$alkyl, 2-hydroxyethyl, allyl, cyclohexyl, benzyl, phenyl, phenyl which is substituted by halogen, $C_1$-$C_4$alkyl or $C_1$-$C_4$alkoxy, a group of the formula A or a group of the formula C

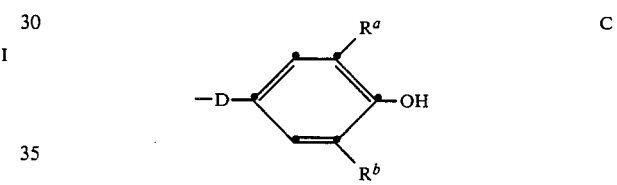

in which D is $C_2$-$C_{20}$alkylene interrupted by

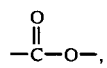

$R^a$ and $R^b$ are $C_1$-$C_{12}$alkyl, $C_5$-$C_6$cycloalkyl, $C_6$-$C_{10}$aryl or $C_7$-$C_9$phenylalkyl and $R^a$ is also hydrogen, or $R^4$ and $R^5$ together are $C_4$-$C_8$alkylene which can be interrupted by $-O-$ or $-N(R^8)-$ and in which $R^8$ is hydrogen, $C_1$-$C_4$alkyl or acetyl, $R^6$ is hydrogen, $C_1$-$C_{12}$alkyl, $C_7$-$C_9$phenylalkyl, $C_3$-$C_5$alkenyl, $C_2$-$C_4$alkanoyl, $C_3$-$C_5$alkenoyl, $-O-$, $-OH$ or $-OR^7$ and $R^7$ is $C_1$-$C_{18}$alkyl, $C_5$-$C_8$cycloalkyl, $C_7$-$C_9$phenylalkyl, phenyl, $C_2$-$C_{18}$alkanoyl or benzoyl, $R^2$, if $n=1$, is Cl, OH, $-OR^3$, $-SR^3$ or $-NR^4R^5$, if $n=2$, $R^2$ is a group $-O-R^9-O-$, $-S-R^9-S-$, $-N(R^{10})-R^9-N(R^{10})-$, $-O-R^9-N(R^{10})-$,

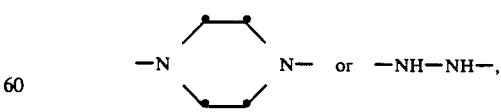

where $R^9$ is $C_2$-$C_{20}$alkylene which can be interrupted by one or more $-O-$, $-N(R^8)-$ or $-OOC-R^{1-}_{7}-COO-$, $C_4$-$C_8$alkenylene, $C_5$-$C_8$cycloalkylene, xylylene, phenylene or tolylene, $R^{10}$ is hydrogen, $C_1$-$C_{12}$allyl, 2-hydroxyethyl, benzyl, phenyl or a group of the formula A, if $n=3$, $R^2$ is a group

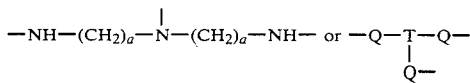

in which a is 2 or 3, Q is —O—, —S— or —N(R$^{10}$)— and T is C$_3$–C$_{20}$alkanetriyl or a group

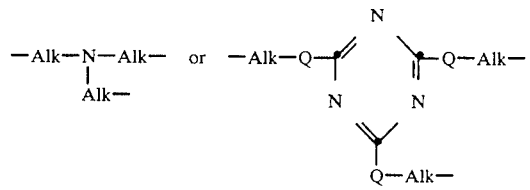

in which Alk is a C$_2$–c$_{12}$alkylene group, if n=4, R$^2$ is a group C(CH$_2$O—)$_4$ or

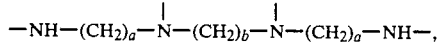

in which a is 2 or 3 and b is 2–12, if n=5, R$^2$ is a group and if n=6, R$^2$ is a group Y is a group

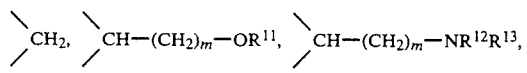

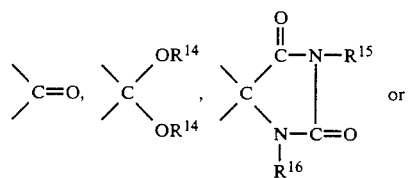

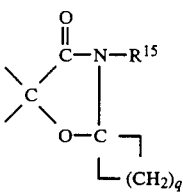

in which m is 0, 1 or 2, q is an integer from 5–11, R$^{11}$ is hydrogen, C$_1$–C$_{18}$alkyl, C$_3$–C$_7$alkenyl, C$_5$–C$_8$cycloalkyl, C$_7$–C$_{11}$aralkyl or a group —CO—R$^{18}$, R$^{12}$ is hydrogen, C$_1$–C$_{12}$alkyl, C$_3$–C$_7$alkenyl, C$_5$–C$_8$cycloalkyl, C$_7$–C$_{11}$aralkyl, C$_2$–C$_4$hydroxyalkyl, C$_3$–C$_8$alkoxyalkyl, C$_4$–C$_{20}$dialkylaminoalkyl, C$_3$–C$_{14}$alkoxycarbonylalkyl or a group of the formula A, R$^{13}$ is C$_1$–C$_{12}$alkyl, C$_2$–C$_4$-hydroxyalkyl, C$_3$–C$_7$alkenyl, C$_5$–C$_8$cycloalkyl, phenyl, phenyl which is substituted by halogen, C$_1$–C$_4$alkyl or C$_1$–C$_4$alkoxy, C$_2$–C$_{20}$alkanoyl, C$_3$–C$_8$alkenoyl, benzoyl, phenylacetyl or a triazinyl radical of the formula B

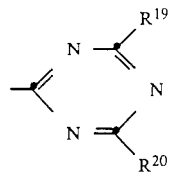

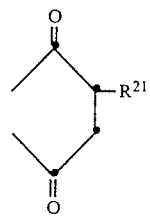

or R$^{12}$ and R$^{13}$ together are C$_4$–C$_8$alkylene which can be interrupted by —O— or —N(R$^8$)— or R$^{12}$ and R$^{13}$ together are a radical of the formula in which R$^{21}$ is C$_1$–C$_{18}$alkyl, R$^{14}$ is C$_1$–C$_{18}$alkyl, C$_5$–C$_8$-cycloalkyl or C$_7$–C$_9$phenylalkyl or both groups R$^{14}$ together are C$_2$–C$_6$alkylene, o-phenylene or o-xylylene, R$^{15}$ is hydrogen, C$_1$–C$_{12}$alkyl, C$_3$–C$_5$alkenyl, C$_7$–C$_9$-phenylalkyl, C$_2$–C$_4$hydroxyalkyl, C$_3$–C$_8$alkoxyalkyl or C$_3$–C$_{14}$alkoxycarbonylalkyl, R$^{16}$ is hydrogen, C$_1$–C$_{12}$alkyl, allyl or benzyl, R$^{17}$ is C$_1$–C$_{12}$alkylene, vinylene, cyclohexylene, xylylene or C$_6$–C$_{12}$arylene, R$^{18}$ is C$_1$–C$_{18}$alkylene, C$_2$–C$_6$alkenyl, C$_5$–C$_8$cycloalkyl, C$_7$–C$_9$phenylalkyl, phenyl or phenyl which is substituted by halogen, nitro, C$_1$–C$_4$alkyl, hydroxyl or C$_1$–C$_4$alkoxy or C$_7$–C$_9$phenylalkyl which is substituted by hydroxyl and C$_1$–C$_4$alkyl, R$^{19}$ is as defined for R$^1$, and R$^{20}$ is Cl, —OH, —OR$^3$, —SR$^3$ or —NR$^4$R$^5$.

If any substituent is alkyl, this may be straight-chain or branched alkyl. Examples of this are methyl, ethyl, n-propyl, iso-propyl, n-butyl, sec-butyl, tert-butyl, iso-pentyl, n-hexyl, n-heptyl, n-octyl, 2-ethylhexyl, iso-decyl, n-dodecyl, n-hexadecyl or n-octadecyl. R$^{12}$, R$^{13}$ and R$^{15}$ in the context of hydroxyalkyl may be, for example 2-hydroxypropyl, 3-hydroxypropyl or 2-hydroxybutyl, but in particular 2-hydroxyethyl.

R$^{12}$ and R$^{15}$ as alkoxyalkyl may be, for example, 2-methoxyethyl, 2-ethoxyethyl, 2-methoxypropyl, 2-butoxypropyl or 2-hexyloxyethyl. R$^{12}$ as dialkylaminoalkyl may be, for example, 2-dimethylaminoethyl, 2-dibutylaminoethyl, 2-diethylaminopropyl or 2-dihexylaminoethyl.

R$^{18}$ as C$_2$–C$_8$-alkenyl may in particular be vinyl or 2-propenyl. R$^6$, R$^{11}$, R$^{12}$, R$^{13}$ and R$^{15}$ as alkenyl may in particular by allyl or methallyl.

R$^6$, R$^7$, R$^{14}$, R$^{15}$, R$^{17}$ and R$^{18}$ as C$_7$–C$_9$phenylalkyl may in particular be benzyl or phenylethyl. R$^{12}$ as C$_7$–C$_{11}$aralkyl may be, for example, benzyl, phenylethyl or naphthylmethyl.

R$^7$, R$^{11}$, R$^{12}$, R$^{13}$, R$^{14}$, and R$^{18}$ as cycloalkyl may in particular be cyclohexyl.

R$^6$, R$^7$, R$^{13}$ and R$^{17}$ as alkanoyl may be straight-chain or branched. Examples of this are acetyl, propionyl, isobutyryl, hexanoyl, octanoyl, lauroyl or stearoyl. R$^6$ as alkenoyl may in particular be acryloyl or methacryloyl.

R$^9$ as alkylene may be straight-chain or branched or interrupted by hetero atoms. Examples of this are di-, tri-, tetra-, hexa-, octa-, deca- or dodecamethylene, 2,2- dimethyltrimethylene or 2,2,4-trimethyltetramethylene, 3-oxapentamethylene, 3-azapentamethylene, 2-methylazapentamethylene, 4-butylazaheptamethylene or 3,6-dioxaoctamethylene.

$R^4$ and $R^5$ together and $R^{12}$ and $R^{13}$ together may be $C_4$-$C_8$alkylene which can be interrupted by —O— or —N($R^8$)—. In this case they form, together with the N atom to which they are bonded, a heterocyclic ring which is preferably 5- or 6-membered. Examples of this are pyrrolidine, piperidine, 2,6-dimethylpiperidine, morpholine, piperazine, 4-methylpiperazine or 4-acetylpiperazine. $R^9$ as alkenylene may in particular be 2-but-1,4-enylene. $R^9$ as cycloalkylene may in particular be 1,4-cyclohexylene.

If $R^2$ is $C_3$-$C_{20}$alkanetriyl, this radical may be straight-chain or branched. Examples of this are propane-1,2,3-triyl, butane-1,3,4-triyl, pentane-1,3,5-triyl or 2-methylpentane-1,3,5-triyl.

Those compounds of the formula II are preferred in which n is an integer from 1–4, $R^1$ is a radical Cl, —$OR^3$ or —$NR^4R^5$, in which $R^3$, $R^4$ and $R^5$ are as defined previously, $R^2$, if n=1, is Cl, —$OR^3$ or —$NR^4R^5$, if n=2, $R^2$ is a group —N($R^{10}$)—$R^9$—N($R^{10}$)— or

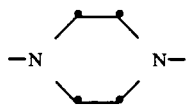

in which $R^9$ and $R^{10}$ are as defined previously, if n=3, $R^2$ is a group

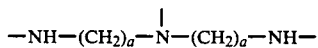
—NH—(CH$_2$)$_a$—N—(CH$_2$)$_a$—NH— and if n=4, $R^2$ is a group

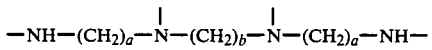
—NH—(CH$_2$)$_a$—N—(CH$_2$)$_b$—N—(CH$_2$)$_a$—NH— in which a is 2 or 3 and b is 2 to 8 and Y is a group

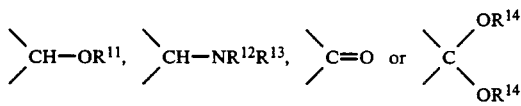

in which $R^{11}$, $R^{12}$, $R^{13}$ and $R^{14}$ are as defined previously.

Among these, those compounds of the formula II are preferred in which n=1 and $R^1$ and $R^2$ are identical.

Compounds of the formula II are particularly preferred in which n=1, $R^1$ and $R^2$ independently of one another are Cl or —$NR^4R^5$, $R^4$ is hydrogen or $C_1$-$C_{12}$alkyl, $R^5$ is $C_1$-$C_{12}$alkyl or $R^4$ and $R^5$ together are pentamethylene or 3-oxapentamethylene, and Y is a group

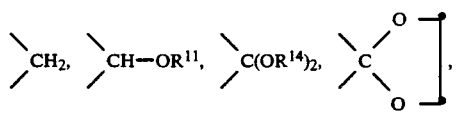

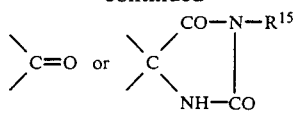

in which $R^{11}$ is hydrogen, $C_1$-$C_{12}$alkyl or —CO—$R^{18}$ and $R^{18}$ is $C_1$-$C_{18}$alkyl or phenyl, $R^{14}$ is $C_1$-$C_4$alkyl and $R^{15}$ is hydrogen or $C_1$-$C_{12}$alkyl.

Compounds of the formula II are advantageously prepared starting from cyanuric chloride and reacting this with an equivalent of a tetramethylpiperidine of the formula XIII.

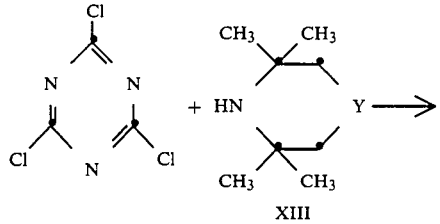

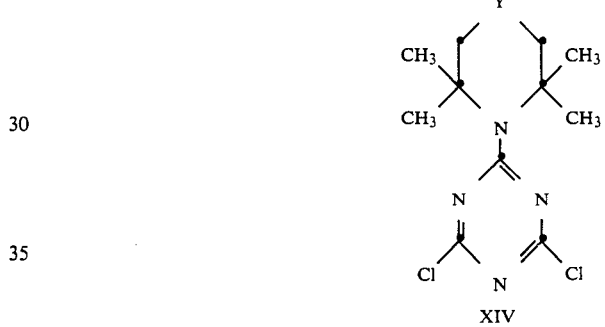

The dichlorotriazine XIV obtained can be reacted in a second reaction step with one mole of a compound $R^1H$, a monochlorotriazine XV being obtained.

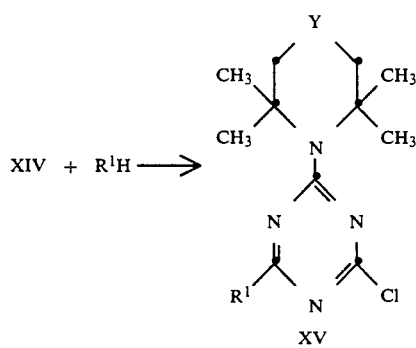

By reacting n equivalents of XV with a compound $R^2$—(H)$_n$, the desired compound of the formula II is obtained in a third reaction step.

The individual reaction steps can be carried out without isolation of the intermediates XIV and XV. All three reaction steps are preferably carried out in an inert solvent with the addition of bases as HCl entrainers.

Examples of suitable solvents are benzene, toluene or xylene. Examples of suitable bases are tertiary amines such as tributylamine or dimethylaniline or alkali metal hydroxides such as NaOH or KaOH or alkali metal carbonates such as Na$_2$CO$_3$ or K$_2$CO$_3$. An excess of the piperidine XIII can also be used as the HCl entrainer.

The reactions preferably take place with warming of the reaction mixtures. The base is preferably added successively to the material as the reaction progresses. The progress of the reaction can, for example, be monitored by analyzing the bound and/or ionized chlorine. Another possibility for checking the reaction is chromatographic analysis of the reaction mixture.

In order to isolate the product, the base salts are expediently filtered off or extracted with water and the organic solution is evaporated. If it is wished to isolate the intermediates, the same procedure is used.

Alternatively, the intermediate XIV can first be reacted with R$^2$(H)$_n$ and subsequently with R$^1$H. If R$^1$ and R$^2$ are identical, the second and third reaction steps can be combined by reacting XIV with 2 equivalents of R$^1$H.

It is obvious that in the first step a compound XIII is used whose Y group is inert towards cyanuric chloride under the reaction conditions. In particular, Y should contain no free OH, NH or SH group. Following the three-step synthesis of II, the original (inert) group Y can be exchanged for another group Y in a further reaction or reaction sequence. For example, an original ketal group $$\diagdown_{\diagup}\!\!C\!\!\diagup^{OR^{14}}_{\diagdown OR^{14}}$$

can be hydrolyzed to the keto group $$\diagdown_{\diagup}C=O.$$

The keto group can be reduced to the group $$\diagdown_{\diagup}CH-OH,$$

which can, in turn, be etherified or esterified with the formation of $$\diagdown_{\diagup}CH-OR^{11}.$$

The keto group $$\diagdown_{\diagup}C=O$$

can be converted by reductive amination into an amino group CH—NHR$^{12}$ which can then be converted into a group $$\diagdown_{\diagup}CH-NR^{12}R^{13}$$

by corresponding N-substitution.

The keto group $$\diagdown_{\diagup}C=O$$

can be converted into the corresponding α-hydroxy- or α-aminonitriles which can, in turn, again be converted into the corresponding spirohydantoins and spirooxazolidones by addition of isocyanates or ketones.

In an analogous manner, other known reactions can be used for the conversion of the group Y.

Examples of individual compounds of the formula II are the following compounds.

| n | R$^1$ | R$^2$ | Y |
|---|---|---|---|
| 1 | 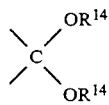 | —N(C$_2$H$_5$)$_2$ | $\diagdown_{\diagup}$CH$_2$ |
| 1 | (C$_4$H$_9$)$_2$N— | —(CH$_2$CH$_2$OH)$_2$ | $\diagdown_{\diagup}$CH$_2$ |
| 1 |  | = R$^1$ | $\diagdown_{\diagup}$CH$_2$ |
| 1 | HOCH$_2$CH$_2$NH— | = R$^1$ | $\diagdown_{\diagup}$CH$_2$ |

-continued

| n | R¹ | R² | Y |
|---|---|---|---|
| 2 | C₄H₉NH— | —NH—(CH₂)₆—NH— | $\rangle$CH₂ |
| 2 | HOCH₂CH₂NH— | —NH—(CH₂)₆—NH— | $\rangle$CH₂ |
| 2 | (C₄H₉)₂N— | —NH—CH₂CH₂—NH— | $\rangle$CH₂ |
| 3 | C₄H₉NH— | —NH—CH₂CH₂—N(—)—CH₂CH₂—NH— | $\rangle$CH₂ |
| 1 | (C₂H₅)₂N— | —NH—⟨C₆H₁₀⟩ | $\rangle$CH—OH |
| 1 | HOCH₂CH₂NH— | = R¹ | $\rangle$CH—OH |
| 1 | (C₄H₉)₂N— | = R¹ | $\rangle$CH—OCOCH₃ |
| 1 | (C₂H₉)(CH₃)N— | = R¹ | $\rangle$CH—OCOC₁₁H₂₃ |
| 1 | (C₄H₉)(CH₃)N— | = R¹ | $\rangle$CH—OCH₂CH=CH₂ |
| 1 | ⟨C₅H₁₀⟩N— | —NHC₈H₁₇ | $\rangle$CH—OCH₂Phenyl |
| 1 | (CH₃)₂N— | = R¹ | $\rangle$CH—O—C₁₂H₂₅ |
| 1 | C₄H₉NH— | = R¹ | $\rangle$CH(O—CH₂)(O—CH₂) |
| 1 | (CH₃)₂N— | = R¹ | $\rangle$CH(O—CH—CH₂OH)(O—CH₂) |
| 1 | C₄H₉NH— | = R¹ | $\rangle$CH(O—CH—CH₂OCO Phenyl)(O—CH₂) |

-continued
| n | R¹ | R² | Y |
|---|---|---|---|
| 1 | $(C_2H_5)_2N-$ | $= R^1$ | $\diagdown CH-N(C_4H_9)-COCH_3$ |
| 1 | $(CH_3)_2N-$ | $= R^1$ | $\diagdown CH-N(C_4H_9)-COOC_2H_5$ |
| 1 | $(C_4H_9)_2N-$ | $= R^1$ | 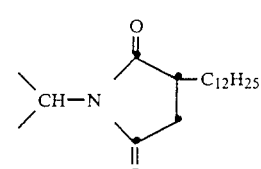 |
| 1 | $(C_4H_9)(CH_3)N-$ | $= R^1$ | $\diagdown CH-N(CH_3)-COC_{11}H_{23}$ |
| 1 | $(C_4H_9)_2N-$ | $= R^1$ | 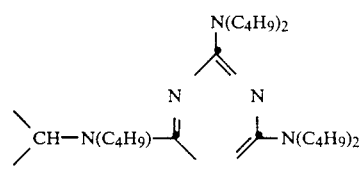 |
| 1 | $C_8H_{17}NH-$ | $= R^1$ | 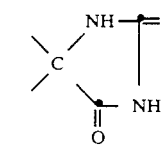 |
| 1 | $(CH_3)_2N-$ | $= R^1$ | 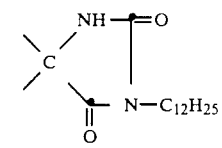 |
| 1 | $(C_4H_9)_2N-$ | $= R^1$ | 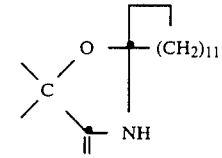 |
| 1 | 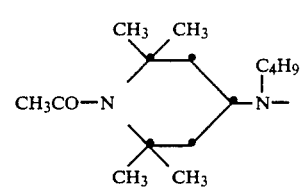 | $= R^1$ | $\diagdown CH_2$ |
| 2 | $C_4H_9NH-$ | $-NHCH_2CH_2OOC(CH_2)_4COOCH_2CH_2NH-$ | $\diagdown CH_2$ |
| 2 | $(C_4H_9)(CH_3)N-$ | $-NH(CH_2)_3OOC-(CH_2)_8-COO(CH_2)_3NH-$ | 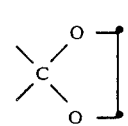 |

-continued
| n | R¹ | R² | Y |
|---|---|---|---|
| 4 | C₄H₉NH— | —NH(CH₂)₃—N(|)—CH₂CH₂—N(|)—(CH₂)₃—NH— | >CH₂ |
| 1 |  | = R₁ | >C—OC₆H₁₃ |
| 1 | —N(CH₂CH—C₄H₉)(C₂H₅) | = R₁ | >CH—OC₁₂H₂₅ |
| 1 | 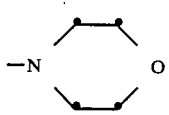 | = R₁ | >CH—OC₆H₁₃ |
| 1 | 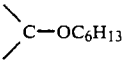 | = R¹ | 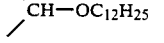 |
| 1 | 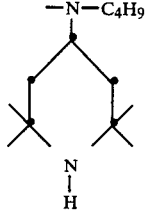 | 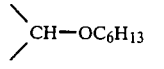 | >CH₂ |
| 2 | 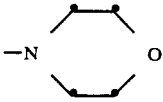 | —NH—(CH₂)₆—NH— | >CH₂ |
| 1 | 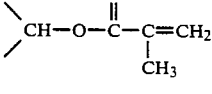 | Cl | >CH₂ |
2) Compounds of the formula III

III

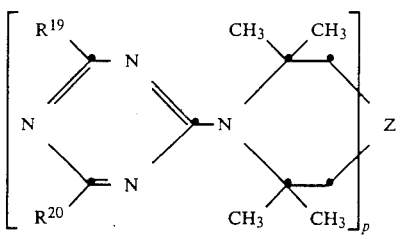

in which p is 2, 3 or 4, $R^{19}$ and $R^{20}$ are as defined previously and Z, if p=2, is one of the groups

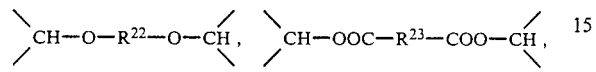

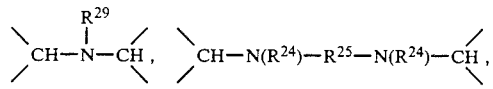

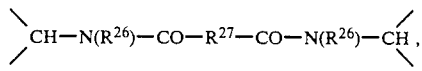

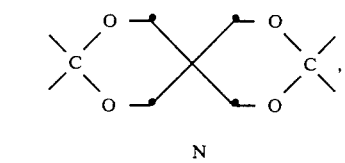

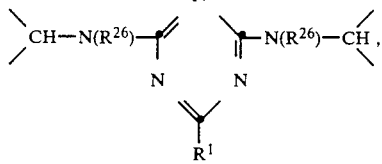

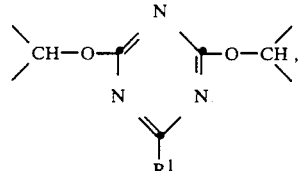

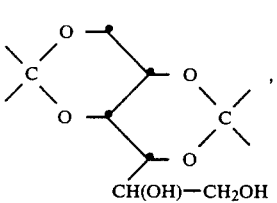

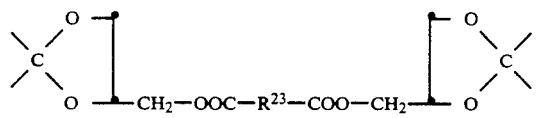

in which $R^{22}$ is $C_2$-$C_{12}$alkylene, $C_4$-$C_8$alkenylene, xylylene or —CO—, $R^{23}$ is $C_1$-$C_{12}$alkylene, vinylene, cyclohexylene, xylylene, $C_6$-$C_{12}$arylene or phenylene which is substituted by halogen, nitro or $C_1$-$C_4$alkyl, or a direct bond, $R^{24}$ is hydrogen, $C_1$-$C_{12}$alkyl, $C_5$-$C_8$cycloalkyl, $C_7$-$C_9$phenylalkyl, $C_3$-$C_7$alkenyl, $C_2$-$C_{18}$alkanoyl, $C_3$-$C_7$alkenoyl, or benzoyl, $R^{25}$ is $C_2$-$C_{12}$alkylene, $C_4$-$C_{16}$alkylene which is interrupted by NH or O, $C_4$-$C_8$alkenylene, xylylene or cyclohexylene, $R^{26}$ is hydrogen, $C_1$-$C_{12}$alkyl, $C_5$-$C_8$cycloalkyl or a group of the formula A, $R^{27}$ is as defined for $R^{23}$ or is a group —NH—$R^{28}$—NH—, $R^{28}$ is $C_2$-$C_{12}$alkylene or $C_6$-$C_{12}$arylene which can be substituted by $C_1$-$C_4$alkyl, $R^{29}$ is hydrogen, $C_1$-$C_{12}$alkyl, $C_2$-$C_{18}$alkanoyl or a triazinyl radical of the formula B, and $R^1$ is as defined at the beginning, and if p=3, Z is one of the groups

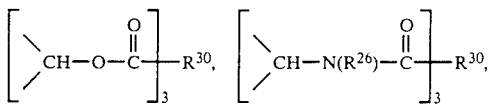

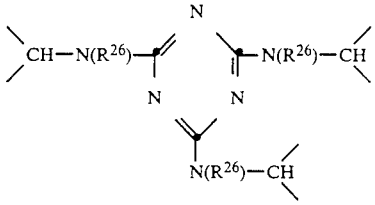

in which $R^{30}$ is $C_3$-$C_{18}$alkanetriyl or $C_8$-$C_{12}$arenetriyl, and if p=4, Z is one of the groups

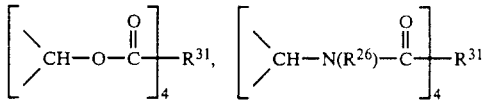

in which $R^{31}$ is $C_4$-$C_{16}$alkanetetrayl or $C_6$-$C_{12}$arenetetrayl.

If $R^{24}$, $R^{26}$ or $R^{29}$ is $C_1$-$C_{12}$alkyl, this may be straight-chain or branched alkyl, for example methyl, ethyl, iso-propyl, n-butyl, sec-butyl, iso-amyl, n-hexyl, n-octyl, 2-ethylhexyl, n-decyl or n-dodecyl. $R^{24}$ as $C_3$-$C_7$alkenyl may in particular be allyl.

$R^{24}$ and $R^{26}$ as $C_5$-$C_8$cycloalkyl may in particular be cyclohexyl. $R^{24}$ as $C_7$-$C_9$phenylalkyl may in particular be benzyl.

$R^{24}$ and $R^{29}$ as $C_2$-$C_{18}$alkanoyl may be straight-chain or branched. Examples of this are acetyl, propionyl, butyroyl, octanoyl, lauroyl or stearoyl. $R^{24}$ as $C_3$-$C_7$alkenoyl may in particular be acryloyl or methacryloyl.

$R^{22}$, $R^{25}$ and $R^{28}$ as $C_2$-$C_{12}$alkylene may be straight-chain or branched. Examples of this are di-, tri-, tetra-, hexa-, octa-, deca- or dodecamethylene, 2,2-dimethyl-trimethylene, diethylmethylene or 2,2,4-trimethyltetramethylene. Moreover, $R^{23}$ as $C_1$-$C_{14}$alkylene may also be, for example, methylene or tetradecamethylene. $R^{25}$ as interrupted alkylene may be, for example, 3-oxapentamethylene, 3-azapentamethylene, 3-methylazapentamethylene or 4-oxaheptamethylene. $R^{22}$ as $C_4$-$C_8$alkenylene may in particular be 2-but-12,4-enylene.

$R^{23}$ and $R^{28}$ as $C_6$-$C_{12}$arylene may be, for example, phenylene, diphenylene or naphthylene.

$R^{30}$ as a trivalent radical may be, for example, propane-1,2,3triyl, butane-1,2,4-triyl, benzene-1,2,4-triyl or naphthalene-1,4,6-triyl.

$R^{31}$ as a tetravalent radical may be, for example, butane-1,2,3,4-tetrayl, benzene-1,2,4,5-tetrayl or naphthalene-1,4,5,8-tetrayl.

Preferred compounds of the formula II are those in which p is 2, 3 or 4, and $R^{19}$ and $R^{20}$ independently of one another are —$OR^3$ or —$NR^4R^5$, in which $R^3$, $R^4$ and $R^5$ are as defined previously, Z, if p=2, is one of the groups

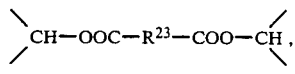

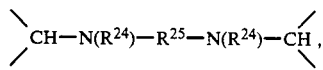

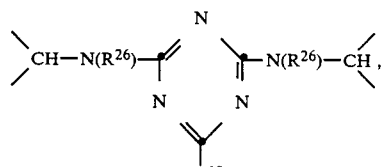

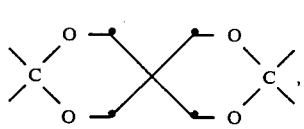

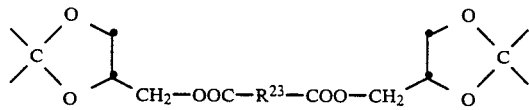

in which $R^{23}$, $R^{24}$, $R^{25}$ and $R^{26}$ are as defined previously, if p=3, Z is one of the groups

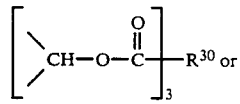

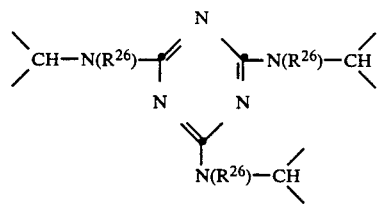

in which $R^{30}$ is $C_3$–$C_8$alkanetriyl or $C_6$–$C_{12}$arenetriyl and $R^{26}$ is as defined previously, and if p=4, Z is a group

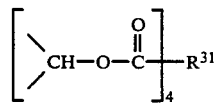

in which $R^{31}$ is $C_4$–$C_{12}$alkanetetrayl or $C_6$–$C_{12}$arenetetrayl.

Among these, compound of the formula III are preferred in which $R^{19}$ and $R^{20}$ are identical.

To prepare the compounds of the formula III, p equivalents of cyanuric chloride can be reacted in a first step with a bis-, tris- or tetrakispiperidine compound XVI.

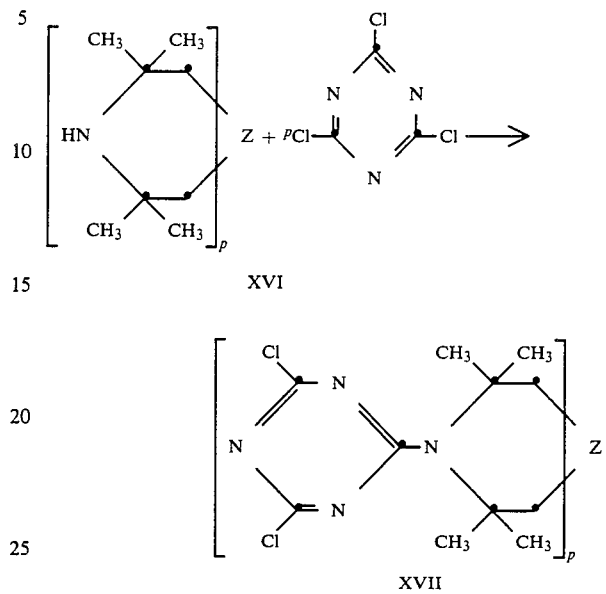

The intermediate XVII can then be reacted in two further reaction steps with $R^{19}H$ and $R^{20}H$. If $R^{19}$ and $R^{20}$ are identical, they can be introduced in one step.

The individual reaction steps mean stepwise substitution of the three chlorine atoms on the triazine ring. They can be carried out as was described previously for the synthesis of II.

Alternatively, a compound of the formula XVIII can be prepared as described for the preparation of II, and this can be reacted with di-, tri- or tetravalent reagents XIX.

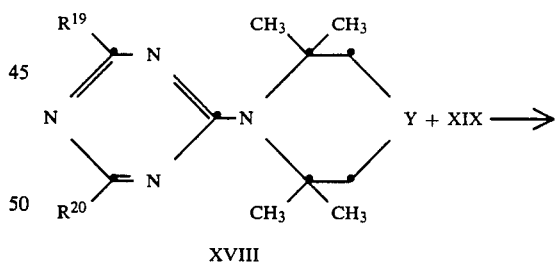

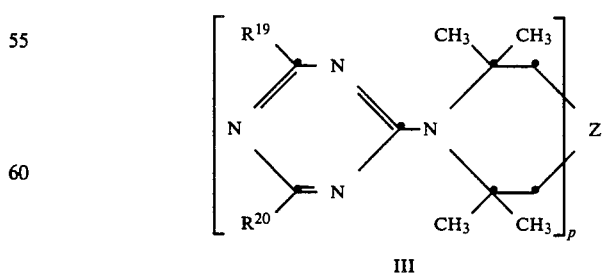

If, for example, Y is a >CH—OH group, a compound Hal—$R^{22}$—Hal, ClCO—$R^{23}$—CoCl, AlkOOC—$R^2$3—COOAlk, or

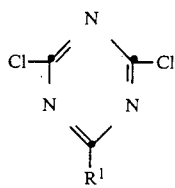

can be used as divalent XIX. A compound $(ClCO)_3R^{30}$, $(AlkOOC)_3R^{30}$ or cyanuric chloride can be used as the trivalent reagent XIX, and a compound $(ClCO)_4R^{31}$ or $(AlkOOC)_4R^{31}$ as the tetravalent XIX. In this, Hal is a halogen atom and Alk is a $C_1$-$C_4$alkyl group.

If Y is a $>CH-NHR^{26}$ group, an analogous procedure can be used. If Y is a $>C=O$ group, this can be reacted, for example, with a tetraol with the formation of a bisketal.

Examples of compounds of the formula III are the following compounds:

| p | $R^{19}$ | $R^{20}$ | Z |
|---|----------|----------|---|
| 2 | iso-$C_3H_7NH$— | $=R^{19}$ | $>CH-OOC-(CH_2)_2-COO-CH<$ |
| 2 | $C_4H_9NH$— | $=R^{19}$ | $>CH-OOC-(CH_2)_8-COO-CH<$ |
| 2 | $(C_2H_5)_2N$— | $=R^{19}$ | (bicyclic diketal structure) |
| 2 | $(CH_3)_2N$— | $=R^{19}$ | (bis-dioxolane with $C_2H_5$ groups and $CH_2OOC-(CH_2)_8-COOCH_2$ linker) |
| 2 | morpholino | —$NHC_4H_9$ | $>CH-N(COCH_3)-(CH_2)_6-N(COCH_3)-CH<$ |
| 2 | $C_8H_{17}NH$— | $=R^{19}$ | $>CH-NH-CO-(CH_2)_4-CO-NH-CH<$ |
| 2 | $C_4H_9NH$— | $=R^{19}$ | $>CH-N(COCH_3)-CH<$ |
| 2 | $(C_2H_5)_2N$— | $=R^{19}$ | triazine: $(C_2H_5)_2N$ and $N(C_2H_5)_2$ substituted triazine linked via $>CH-N-CH<$ |
| 2 | $(C_4H_9)(CH_3)N$— | $=R^{19}$ | bis-triazine with $C_4H_9$ groups, linked via $>CH-N$ and $-N-CH<$, with $OCH(CH_3)_2$ |

-continued

| p | R¹⁹ | R²⁰ | Z |
|---|---|---|---|
| 2 | (C₄H₉)(CH₃)N— | = R¹⁹ | (structure: triazine with two CH-O- linkages and NHC₈H₁₇ substituent) |
| 3 | (C₄H₉)₂N— | = R¹ | (structure: triazine with three CH-N(C₄H₉)- linkages) |
| 4 | C₄H₉NH— | —N(CH₃)₂ | (structure: two triazines bridged by —NH—(CH₂)₆—NH—, each with CH-N(C₂H₅)- substituents) |
| 2 | (CH₃)₂CHNH— | = R¹⁹ | (structure: two triazines bridged by —(CH₂)₆—, with (CH₃)₂N- and N(CH₃)₂ substituents) |
| 4 | C₄H₉O— | = R¹⁹ | (structure: CH₂—CH—CH—CH₂ chain with CO-O-CH branches) |
| 2 | —N(morpholine ring with O) | = R¹⁹ | \CH—N(H)—(CH₂)₆—N(H)—CH/ |

3) Compounds of the formula IV

IV

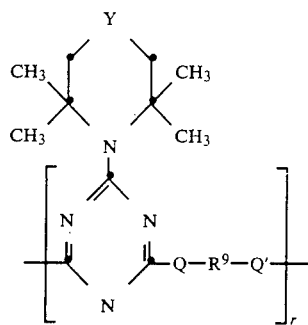

in which r has a value from 3 to 50, Q and Q' independently of one another are —O—, —S— or —N(R¹⁰)— and Y, R⁹ and R¹⁰ are as defined previously, or in which —Q—R⁹—Q'— is a group —NHNH—,

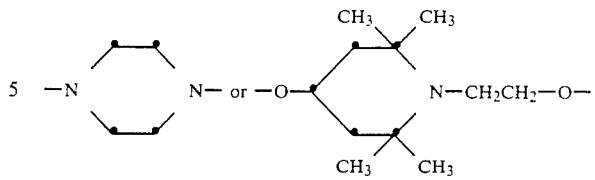

Preferably, r has a value from 3 to 25 and Q and Q' are —O— or —N($R^{10}$).

These compounds can be prepared by reaction of a dichlorotriazine XIV with a compound HQ—$R^9$—Q'H. The latter compound may be, for example, a diol, a dithiol, a diamine or a hydroxyamine. Depending on the molar ratio of the two educts, products having high or low degrees of polycondensation r are obtained. The polycondensation is carried out in the presence of bases which bind the HCl formed.

Examples of compounds of the formula IV are the following compounds:

| Y | Q | Q' | $R^9$ |
|---|---|---|---|
| ⟩CH₂ | NH | NH | —(CH₂)₆— |
| ⟩CH—OCOCH₃ | O | O | —(CH₂)₄— |
| ⟩C⟨O—⟩ (cyclic carbonate-like) | NH | NH | —(CH₂)₆— |
| ⟩CH₂ | NH | NH | —CH₂CH₂OCC(CH₂)₂COOCH₂CH₂— |
| ⟩CH—N(C₄H₉)—COCH₃ | O | O | piperidine—N—CH₂CH₂— (2,2,6,6-tetramethyl) |
| ⟩CH—OC₄H₉ | NH | NH | —CH₂CH₂NHCH₂CH₂— |
| ⟩CH—N(C₄H₉)—[triazine with N(C₄H₉)₂ groups] | NH | NH | —(CH₂)₃—O—(CH₂)₃— |

4) Compounds of the formula V

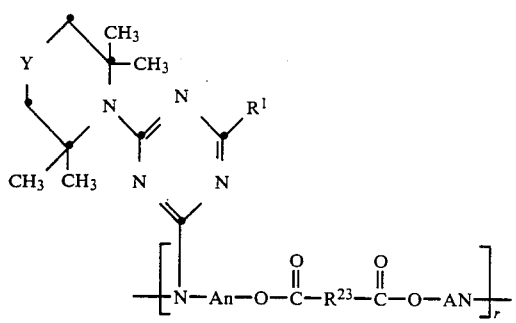

V

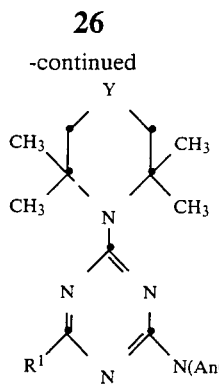

-continued

+ AlkOOC—R²³—COOAlk

↓

V in which r has a value from 3 to 50, Y and $R^1$ are as defined previously, An is a $C_2$-$C_4$alkylene group and $R^{23}$ is as defined previously.

These compounds can be prepared from a monochlorotriazine of the formula XV by reaction with a compound HN(AnOH)$_2$ and subsequent polycondensation with a dicarboxylic acid dialkyl ester XV + HN(AnOH)$_2$ 

In this, Alk is $C_1$-$C_4$alkyl. An is preferably —CH$_2$CH$_2$—. The degree of polycondensation r here can also be varied by varying the molar ratio of the educts. Examples of utilizable dicarboxylic acid dialkyl esters are dimethyl succinate, diethyl adipate, dimethyl sebacate, dimethyl terephthalate or diethyl isophthalate.

Examples of compounds of the formula V are the following compounds:

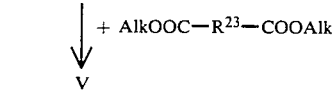

| Y | $R^1$ | An | $R^{23}$ |
|---|---|---|---|
| ＼CH₂／ | —N(C₄H₉)₂ | —CH₂CH₂— | —CH₂CH₂— |
| ＼CH₂／ | (tetramethylpiperidinyl)—N | —CH₂CH₂— | (phenylene) |
| ＼C=O／ | —N(C₂H₅)₂ | —CH₂CH₂— | —(CH₂)₄— |
| ＼CH—OCH₂CH=CH₂／ | —NHC₄H₉ | —CH₂—CH(CH₃)— | —(CH₂)₈— |
| ＼C(O)(O)／ (dioxolane) | —N(morpholinyl) | —CH₂CH₂— | —CH₂CH₂— |

5) Compounds of the formula VI

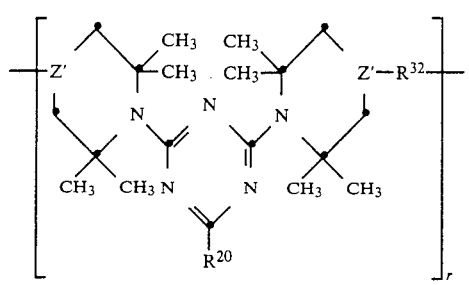

in which r has a value from 3 to 50, $R^{20}$ is as defined previously and

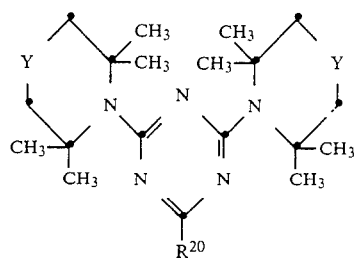

in which Y contains an OH or NH group, by stepwise substitution of cyanuric chloride as described under (1) and reacting this with a difunctional reagent. If, for

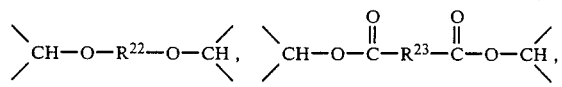

is one of the following groups

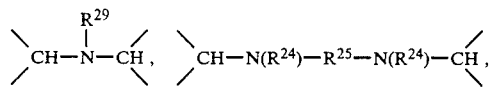

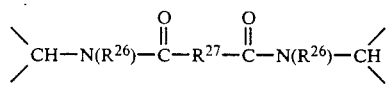

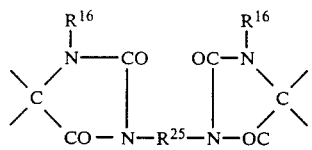

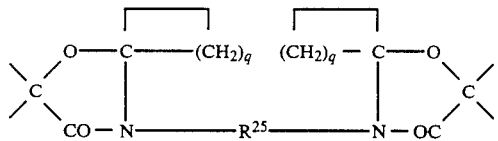

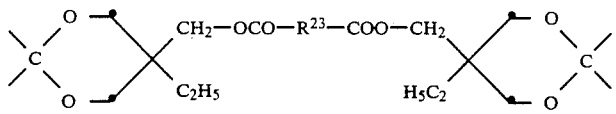

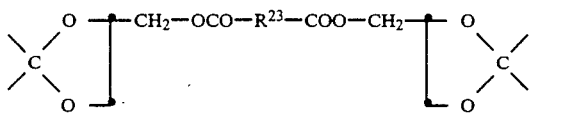

in which q, $R^{16}$, $R^{22}$, $R^{23}$, $R^{24}$, $R^{25}$, $R^{26}$, $R^{27}$ and $R^{29}$ are as defined previously.

These compounds can be prepared by first preparing a compound of the formula XX example, Y is a CH—OH group, a compound Hal—$R^{2}$-2—Hal or AlkOOC—$R^{23}$—COOAlk can be used as the difunctional reagent.

Alternatively, a bis-piperidine compound of the formula XXI

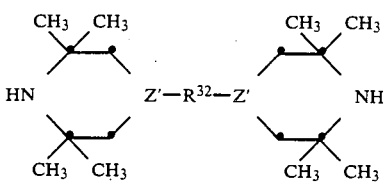

can be reacted with a compound of the formula XXII

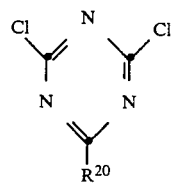

Or a compound XXI is reacted with one equivalent of cyanuric chloride and $R^{20}$ is introduced at the end by reaction with $R^{20}H$.

Examples of compounds of the formula VI are

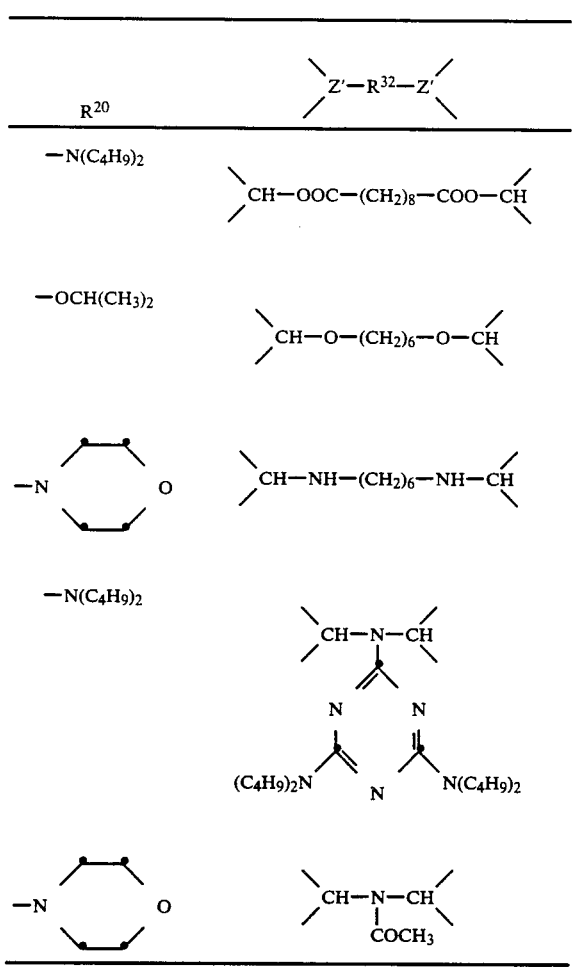

6) Compounds of the formula VII

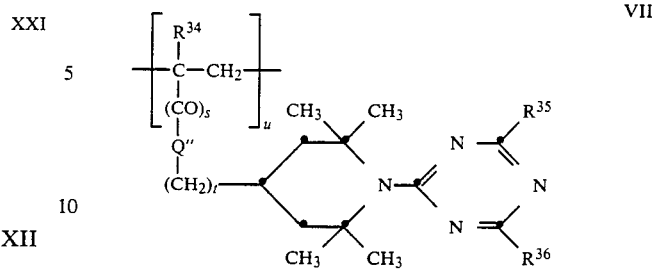

in which s is 0 or 1, t is 0 or 2 and u has a value from 5 to 100, Q'' is —O—, —NH— or —N($C_1$-$C_4$alkyl)—, $R^{34}$ is hydrogen or methyl, $R^{35}$ and $R^{36}$ independently of one another are —$OR^3$, —$SR^3$ or —$NR^4R^5$, and copolymers of such a compound with (meth)acrylic acid, alkyl (meth)acrylates, hydroxyalkyl (meth)acrylates or maleic anhydride.

Such compounds can be prepared by polymerization of a monomer of the formula XXIII

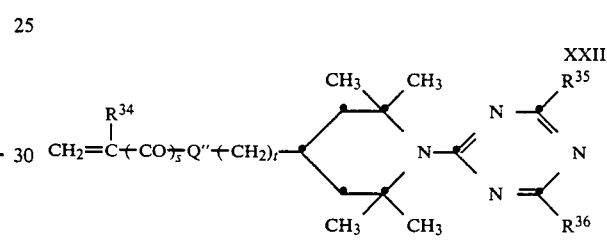

or by copolymerization of XXIII with (meth)acrylic acid, an alkyl (meth)acrylate, a hydroxyalkyl (meth)acrylate or maleic anhydride. The polymerization takes place using radical polymerization initiators, for example organic peroxides or azo compounds. The monomers XXIII can be prepared by stepwise substitution of cyanuric chloride - as described under (1).

Preferred compounds of the formula VII are those in which s=1, t=0 and Q'' is —O—.

Examples of compounds of the formula VII are:

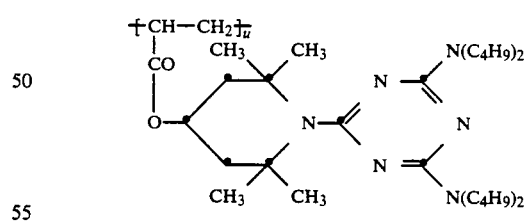

and its 1:1-copolymer with methyl acrylate,

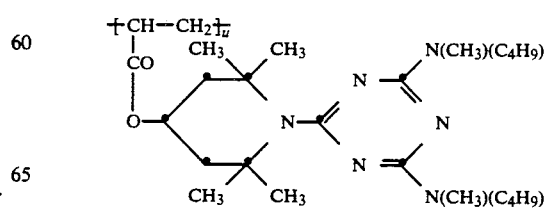

and its 1:1-copolymer with butyl acrylate,

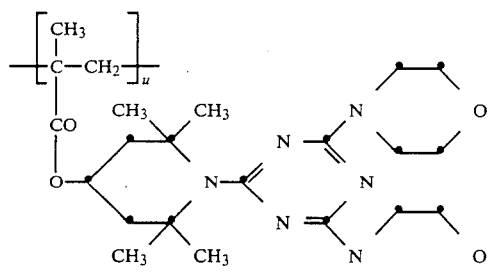

and its 1:1-copolymer with methyl methacrylate,

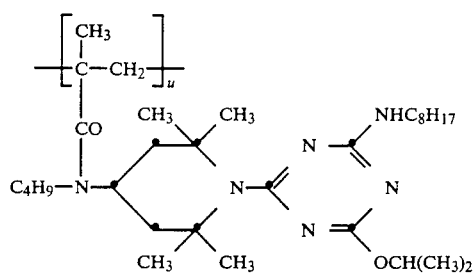

and its 1:1-copolymer with hydroxyethyl acrylate.

7) Compounds of the formula VIII

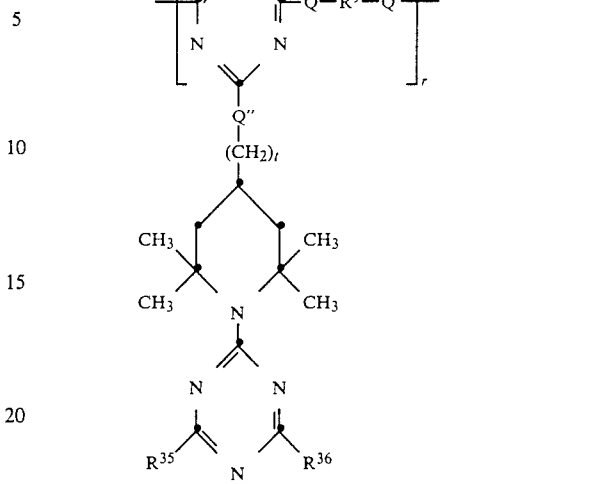

VIII in which r has a value from 3 to 50, t is 0 or 2, Q and Q' are as defined previously, Q" is —O—, —NH— or —N($C_1$-$C_4$alkyl)— and $R^9$, $R^{35}$ and $R^{36}$ are as defined previously.

These compounds can be prepared by polycondensation of a compound of the formula XXIV

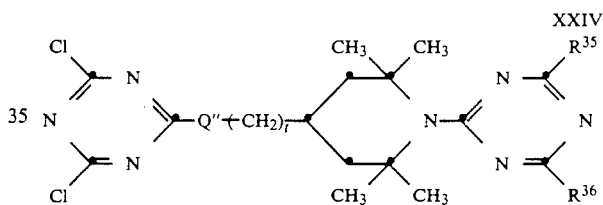

XXIV with a difunctional compound HQ—$R^9$—Q'H in the presence of two equivalents of a base. The educts XXIV can be prepared by stepwise substitution of cyanuric chloride - as described under (1).

Preferred compounds of the formula VIII are those in which t=0.

Examples of compounds of the formula VIII are the following compounds:

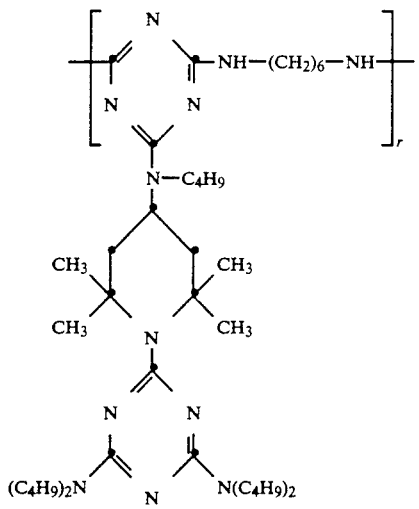

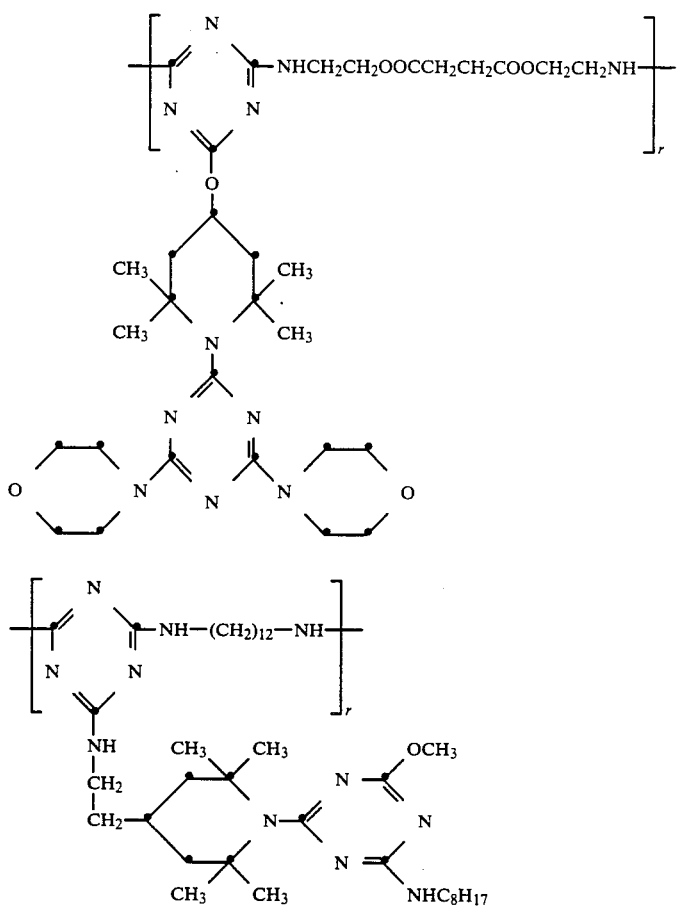

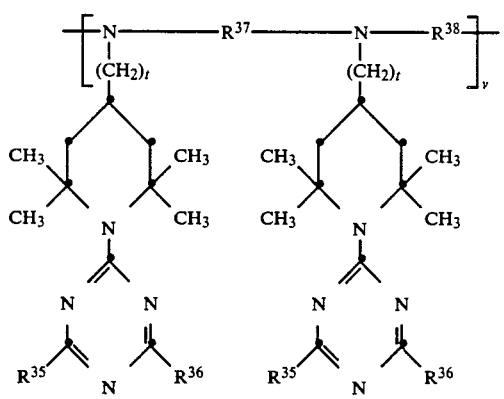

8) Compounds of the formula IX

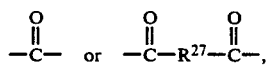
                                               IX in which v has a value from 2 to 30, t is 0 or 2, $R^{35}$ and $R^{36}$ are as defined previously, $R^{37}$ is $C_2$-$C_8$alkylene, $C_4$-$C_8$alkenylene, xylylene, —$CH_2$—CH(OH)—$CH_2$— or —$CH_2$CH(OH)$CH_2$—O—$R^{39}$—O—$CH_2$CH(CH)$CH_2$—, $R^{38}$ is as defined for $R^{37}$ or is $$-\overset{O}{\underset{\|}{C}}- \quad \text{or} \quad -\overset{O}{\underset{\|}{C}}-R^{27}-\overset{O}{\underset{\|}{C}}-,$$

$R^{39}$ is $C_2$-$C_8$alkylene, phenylene or

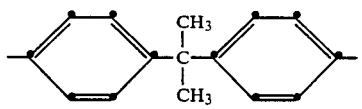

and $R^{27}$ is as defined previously.

These compounds can be prepared from a compound of the formula XXV

 XXV

by reaction with a difunctional compound whose functional groups can react with secondary amines. Examples of this are the dihalides Hal—$R^{38}$—Hal or epichlorohydrin or diglycidyl ethers of the formula XXVa

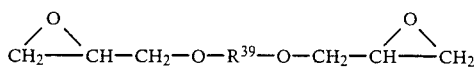

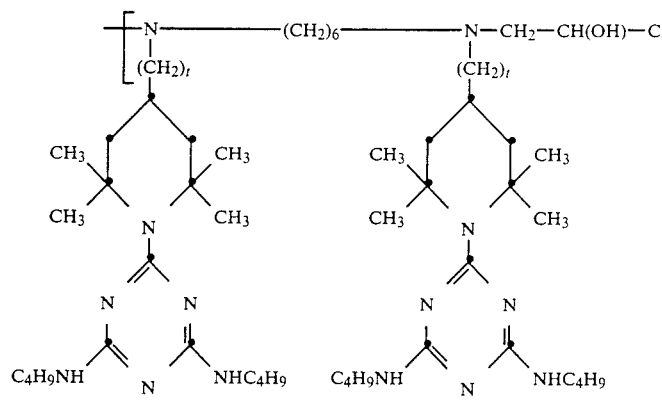

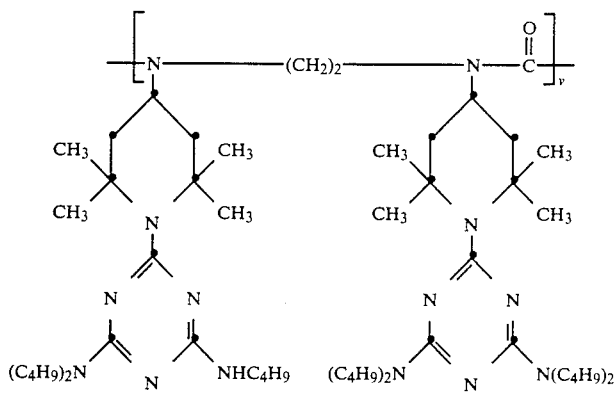

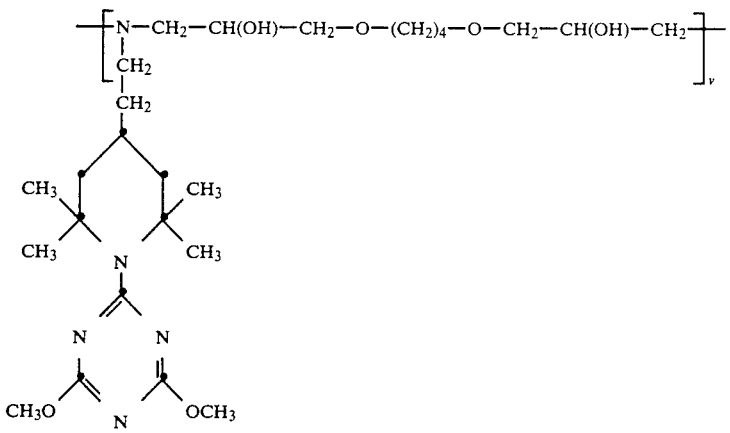

by reaction with Hal—R$^{37}$—Hal, with epichlorohydrin or with a diglycidyl ether XXVa. The educts XXV and XXVI can be prepared by stepwise substitution of cyanuric chloride - as described under (1) or (2).

Examples of compounds of the formula IX are:

If R$^{38}$ is identical to R$^{37}$, the compounds of the formula IX can be prepared from a primary amine of the formula XXVI

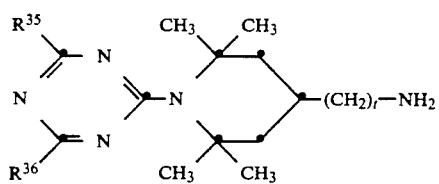

XXVI

9) Compounds of the formula X

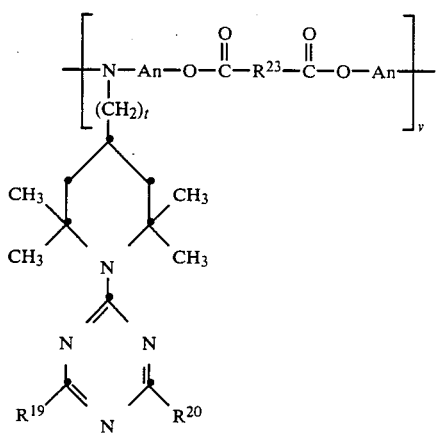

X in which t is 0 or 2, v has a value from 2 to 30, An is $C_2-C_4$alkylene, and $R^{19}$, $R^{20}$ and $R^{23}$ are as defined previously. These compounds can be prepared by polycondensation of compounds of the formula XXVII

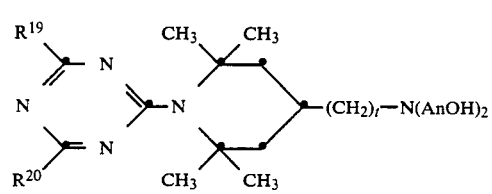

XXVII with dicarboxylic acid dialkyl esters AlkOOC—$R^2$-3—COOAlk. Preferred compounds of the formula X are those in which t is zero and An is —$CH_2CH_2$—. The educts XXVII can be prepared by stepwise substitution of cyanuric chloride - as described in (1).

Examples of compounds of the formula X are:

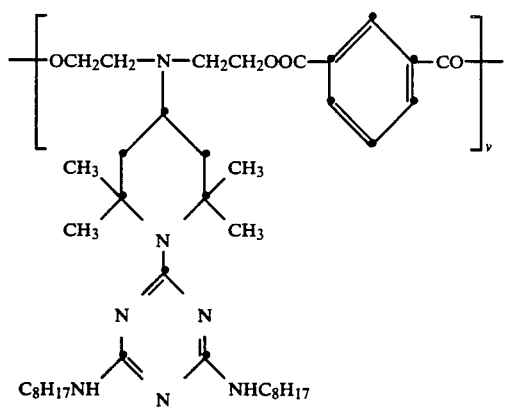

-continued

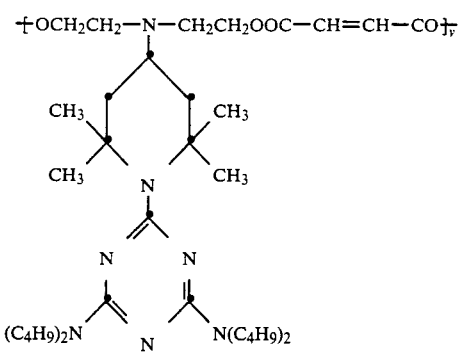

10) compounds of the formula XI

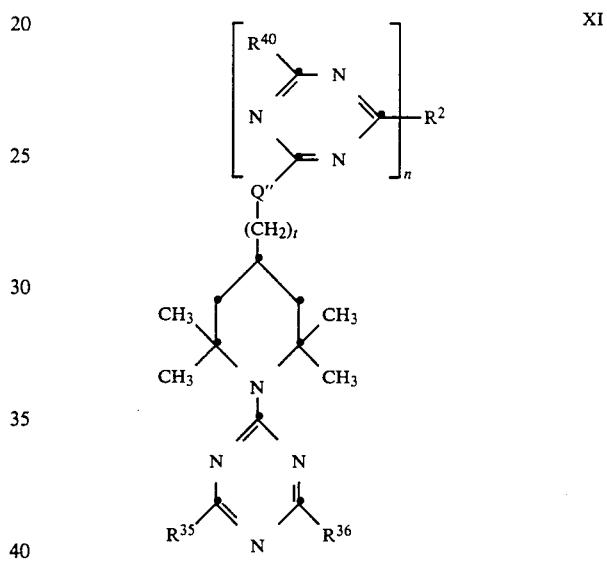

XI in which n is an integer from 1 to 6, t is 0 or 2, $R^2$, $Q''$, $R^{35}$ and $R^{36}$ are as defined previously and $R^{40}$ is either as defined for $R^1$ or is a group

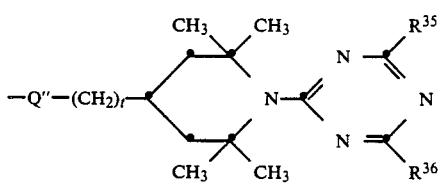

To prepare these compounds, n equivalents of a compound of the formula XXVIII

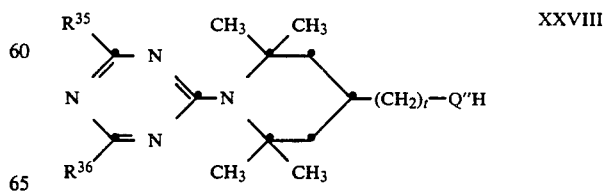

XXVIII can be reacted with one equivalent of a compound of the formula

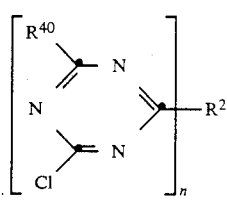

in the presence of n equivalents of a base.

However, a compound of the formula XXVIIIa

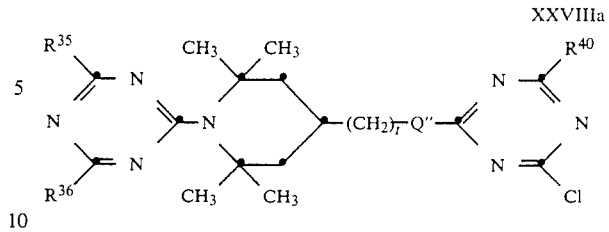

can also first be prepared and subsequently n equivalents of XXVIIIa can be reacted with one equivalent of $R^2(H)_n$.

The educts XXVIII and XXVIIIa can be prepared by stepwise substitution of cyanuric chloride - as described under (1).

Examples of compounds of the formula XI are the following compounds:

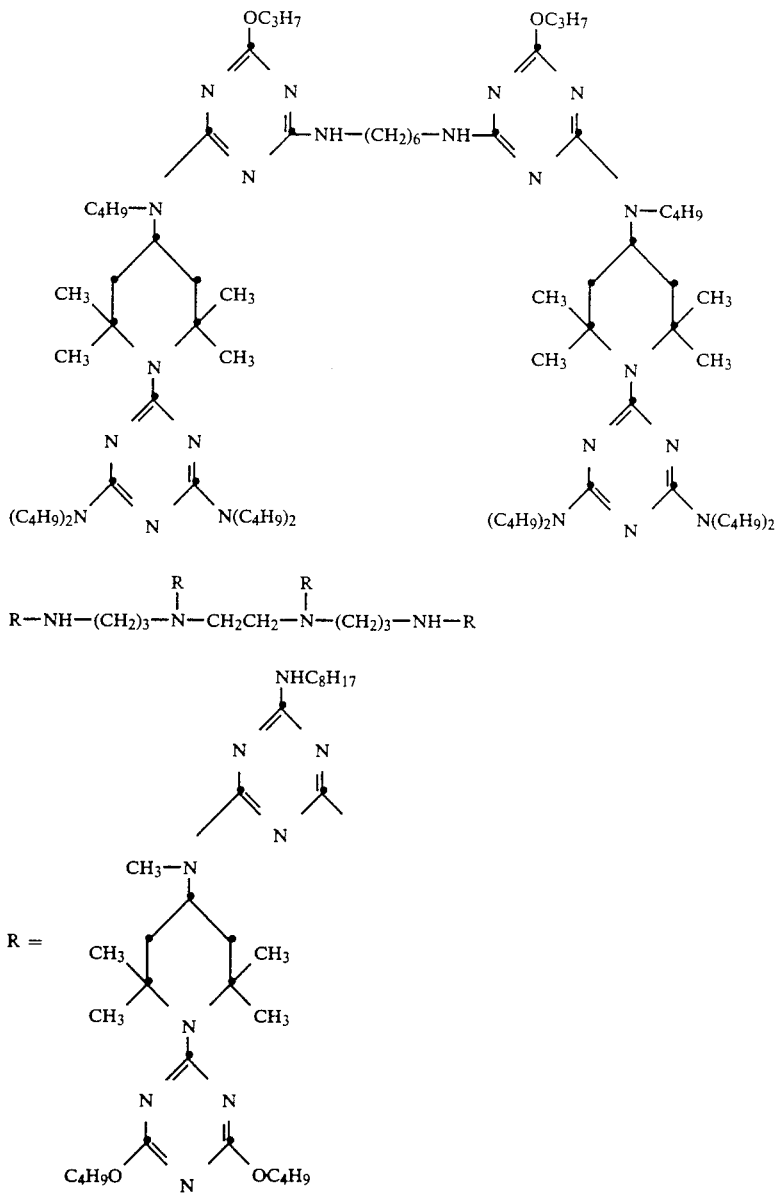

11) compounds of the formula XII

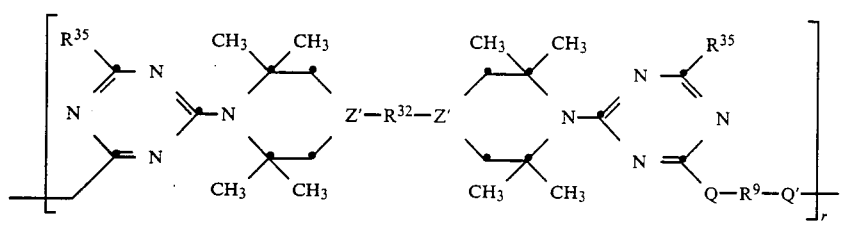
XII in which r has a value from 3 to 50, $R^9$ and $R^{35}$ are as defined previously, the group

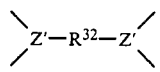

is as defined for class 5 and Q and Q' independently of one another are —O—, —S— or —N($R^{10}$)—.

To prepare these compounds, a bis-piperidine compound of the formula XXIX

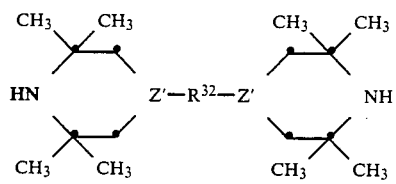
XXIX is first reacted with 2 equivalents of cyanuric chloride, the radical $R^{35}$ is then introduced by reaction with 2 equivalents of $R^{35}$H and the product is reacted with a difunctional compound HQ—$R^9$—Q'H. This can be, for example, a diol, a dithiol, a diamine or a hydroxyamine.

Examples of compounds of the formula XII are:

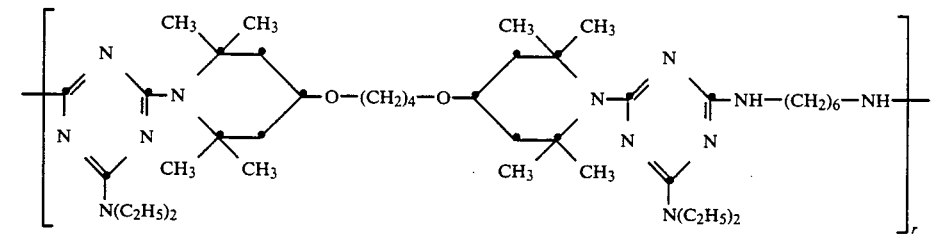

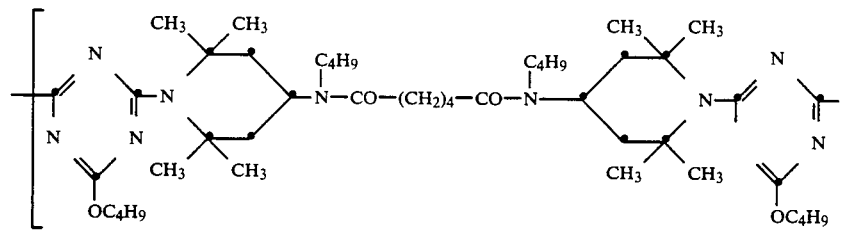

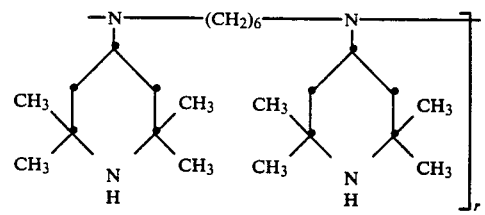

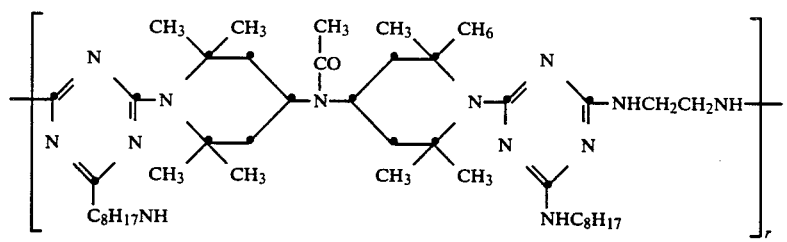

The compounds of the formulae IV to X and XII are polymeric compounds where the formula represents the recurring molecular unit. The terminal groups of these polymeric products may be appropriate groups from the educts or from the polymerization catalyst. A desired limit to the molecular weight of the polymeric products can be achieved by addition of monofunctional compounds or of chain terminators in the preparation (polymerization). In this case, terminal groups also result which correspond to these additives.

The compounds according to the invention are utilizable as stabilizers for organic materials against damage by light, oxygen and heat. Such materials to be stabilized may be, for example, oils, fats, waxes, cosmetics, biocides or photographic or reprographic materials. Use in polymeric materials as present in plastics, rubbers, paints or adhesives is of particular interest. Examples of polymers which may be stabilized in this manner are the following:

1. Polymers of mono- and diolefins, for example polypropylene, polyisobutylene, polybut-1-ene, polymethylpent-1-ene, polyisoprene or polybutadiene and polymers of cycloolefins, for example, cyclopentene or norbornene; furthermore polyethylene (which may or may not be crosslinked), for example high density polyethylene (HDPE), low density polyethylene (LDPE), and linear low density polyethylene (LLDPE).

2. Mixtures of the polymers mentioned under 1), for example mixtures of polypropylene with polyisobutylene, polypropylene with polyethylene (for example PP/HDPE, PP/LDPE) and mixtures of various polyethylene types (for example LDPE/HDPE).

3. Copolymers of mono- and diolefins with one another or with other vinyl monomers, for example ethylene-propylene copolymers, linear low density polyethylene (LLDPE) and mixtures thereof with low density polyethylene (LDPE), propylene-but-1-ene copolymers, propylene-isobutylene copolymers, ethylene-but-1-ene copolymers, ethylene-hexene copolymers, ethylene-methylpentene copolymers, ethylene-heptene copolymers, ethylene-octene copolymers, propylene-butadiene copolymers, isobutylene-isoprene copolymers, ethylene-alkyl acrylate copolymers, ethylene-alkyl methacrylate copolymers, ethylene-vinyl acetate copolymers or ethylene-acrylic acid copolymers and their salts (ionomers), and also terpolymers of ethylene with propylene and a diene, such as hexadiene, dicyclopentadiene or ethylidenenorbornene; furthermore mixtures of such copolymers with one another and with polymers mentioned under 1), for example polypropylene/ethylene-propylene copolymers, LDPE/ethylene-vinyl acetate copolymers, LDPE/ethylene-acrylic acid copolymers, LLDPE/ethylene-vinyl acetate copolymers and LLDPE/ethylene-acrylic acid copolymers.

3a. Hydrocarbon resins (for example $C_5$–$C_9$), including hydrogenated modifications thereof (for example tackifying resins).

4. Polystyrene, poly-(p-methylstyrene), poly—(α-methylstyrene).

5. Copolymers of styrene or α-methylstyrene with dienes or acrylic derivatives, for example styrene-butadiene, styrene-acrylonitrile, styrene-alkyl methacrylate, styrene-butadiene-alkyl acrylate, styrene-maleic anhydride, styrene-acrylonitrile-methyl acrylate; mixtures of high impact strength of styrene copolymers and another polymer, for example a polyacrylate, a diene polymer or an ethylene-propylene-diene terpolymer; and also block copolymers of styrene, for example styrene-butadiene-styrene, styrene-isoprene-styrene, styrene-ethylene/butylene-styrene or styrene-ethylene/propylene-styrene.

6. Graft copolymers of styrene or α-methylstyrene, for example styrene on polybutadiene, styrene on polybutadiene-styrene or polybutadiene-acrylonitrile copolymers, styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene, styrene and alkyl acrylates or alkyl methacrylates on polybutadiene, styrene and acrylonitrile on ethylenepropylene-diene terpolymers, styrene and acrylonitrile on poly(alkyl acrylates) or poly(alkyl methacrylates), styrene and acrylonitrile on acrylate-butadiene copolymers, and also mixtures thereof with the copolymers mentioned under 5), which are known, for example, as so-called ABS, MBS, ASA or AES polymers.

7. Halogen-containing polymers, for example polychloroprene, chlorinated rubber, chlorinated or chlorosulfonated polyethylene, epichlorohydrin homo- and copolymers, in particular polymers of halogen-containing vinyl compounds, for example polyvinyl chloride, polyvinylidene chloride, polyvinyl fluoride, polyvinylidene fluoride; and also copolymers thereof such as vinyl chloride-vinylidene chloride, vinyl chloride-vinyl acetate or vinylidene chloride-vinyl acetate.

8. Polymers which are derived from α,β-unsaturated acids and their derivatives, such as polyacrylates and polymethacrylates, polyacrylamides and polyacrylonitriles.

9. copolymers of the monomers mentioned under 8) with one another or with other unsaturated monomers, for example acrylonitrile-butadiene copolymers, acrylonitrile-alkyl acrylate copolymers, acrylonitrile-alkoxyalkyl acrylate copolymers, acrylonitrile-vinyl halide copolymers or acrylonitrile-alkyl methacrylate-butadiene terpolymers.

10. Polymers which are derived from unsaturated alcohols and amines or their acyl derivatives or acetals, such as polyvinyl alcohol, polyvinyl acetate, stearate, benzoate or maleate, polyvinylbutyral, poly(allyl phthalate), polyallylmelamine; and their copolymers with the olefins mentioned in item 1.

11. Homo- and copolymers of cyclic ethers, such as polyalkylene glycols, polyethylene oxide, polypropylene oxide or their copolymers with bisglycidyl ethers.

12. Polyacetals, such as polyoxymethylene, and also those polyoxymethylenes which contain comonomers, for example ethylene oxide; polyacetals which are modified with thermoplastic polyurethanes, acrylates or MBS.

13. Polyphenylene oxides and sulfides and their mixtures with styrene polymers or polyamides.

14. Polyurethanes which are derived from polyethers, polyesters and polybutadienes with terminal hydroxyl groups on the one hand and aliphatic or aromatic polyisocyanates on the other hand, and their precursors.

15. Polyamides and copolyamides which are derived from diamines and dicarboxylic acids and/or from aminocarboxylic acids or the corresponding lactams, such as polyamide 4, polyamide 6, polyamide 6/6, 6/10, 6/9, 6/12, 4/6, polyamide 11, polyamide 12, aromatic polyamides originating from m-xylene, diamine and adipic acid; polyamides prepared from hexamethylenediamine and iso- and/or terephthalic acid and, if desired, an elastomer as a modifier, for example poly-2,4,4-trimethylhexamethyleneterephthalamide and poly-m-phenyleneisophthalamide. Block copolymers of the polyamides mentioned previously with polyolefins, olefin copolymers, ionomers or chemically bonded or grafted elastomers; or with polyethers, for example with polyethylene glycol, polypropylene glycol or polytetramethylene glycol. Furthermore with EPDM or ABS-modified polyamides or copolyamides; and also polyamides condensed during processing ("RIM polyamide systems").

16. Polyureas, polyimides, polyamide-imides and polybenzimidazoles.

17. Polyesters which are derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate, polyhydroxybenzoates, and also block polyether esters which are derived from polyethers having hydroxyl terminal groups; furthermore with polycarbonates or MBS-modified polyesters.

18. Polycarbonates and polyester carbonates.

19. Polysulfones, polyether sulfones and polyether ketones.

20. Crosslinked polymers which are derived from aldehydes on the one hand and phenols, urea or melamine on the other hand, such as phenol-formaldehyde, urea-formaldehyde and melamine-formaldehyde resins.

21. Drying and non-drying alkyd resins.

22. Unsaturated polyester resins which are derived from copolyesters of saturated and unsaturated dicarboxylic acids with polyhydric alcohols, and also vinyl compounds as crosslinking agents, and also their halogen-containing, poorly flammable modifications.

23. Crosslinkable acrylic resins which are derived from substituted acrylic acid esters, for example epoxyacrylates, urethane acrylates or polyester acrylates.

24. Alkyd resins, polyester resins and acrylate resins which are crosslinked with melamine resins, urea resins, polyisocyanates or epoxy resins.

25. Crosslinked epoxy resins which are derived from polyepoxides, for example from bis-glycidyl ethers or from cycloaliphatic diepoxides.

26. Natural polymers, such as cellulose, natural rubber, gelatin, and also their chemically derived polymer homologue derivatives, such as cellulose acetates, propionates and butyrates, or the cellulose ethers, such as methylcellulose; also colophony resins and derivatives.

27. Mixtures (polyblends) of the previously mentioned polymers, for example PP/EPDM, polyamide/EPDM or ABS, PVC/EVA, PVC/ABS, PVC/MBS, PC/ABS, PBTP/ABS, PC/ASA, PC,PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP and PA/PPO.

The stabilization of polyolefins and of binders for paints is of particular significance.

The stabilizers are expediently added to the organic materials in an amount from 0.01 to 5% by weight, calculated on the material to be stabilized. 0.1 to 2% by weight is preferably used. The addition to polymeric materials may even be carried out during their preparation (polymerization). Preferably, it is carried out before or during the molding of the polymer.

In certain cases it may be advantageous to use mixtures of two or more of the stabilizers according to the invention.

Other stabilizers or various customary additives can also be added to the organic material together with the stabilizers according to the invention. Examples of this are the following additives:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-i-butylphenol, 2,6-dicyclopentyl-4-methylphenol, 2-(α-methylcyclohexyl)-4,6-dimethylphenol, 2,6-di-octadecyl-4-methylphenol, 2,4,6-tri-cyclohexylphenol, 2,6-di-tert-butyl-4-methoxymethylphenol, 2,6-di-nonyl-4-methylphenol.

1.2. Alkylated hydroquinones, for example 2,6-di-tert-butyl-4-methoxyphenyl, 2,5-di-tert-butyl-hydroquinone, 2,5-di-tert-amyl-hydroquinone, 2,6-di-phenyl-4-octadecyloxyphenol.

1.3. Hydroxylated thiodiphenyl ethers, for example 2,2'-thio-bis-(6-tert-butyl-4-methylphenol), 2,2'-thio-bis-(4-octylphenol), 4,4'-thio-bis-(6-tert-butyl-3-methylphenol), 4,4'-thio-bis-(6-tert-butyl-2-methylphenol).

1.4. Alkylidene disphenols, for example 2,2'-methylene-bis-(6-tert-butyl-4-methylphenol), 2,2'-methylene-bis-(6-tert-butyl-4-ethylphenol), 2,2'-methylene-bis-[4-methyl-6-(α-methylcyclohexyl)-phenol], 2,2'-methylene-bis-(4-methyl-6-cyclohexylphenol), 2,2'-methylene-bis-(6-nonyl-4-methylphenol), 2,2'-methylene-bis-(4,6-di-tert-butylphenol), 2,2'-ethylidene-bis-(4,6-di-tert-butylphenol), 2,2'-ethylidene-bis-(6-tert-butyl-4-isobutylphenol), 2,2'-methylene-bis-[6-(α-methylbenzyl)-4-nonylphenol], 2,2'-methylene-bis-[6-(α,α-dimethylbenzyl)-4-nonylphenol], 4,4'-methylene-bis-(2,6-di-tert-butylphenol), 4,4'-methylene-bis-(6-tert-butyl-2-methyl-phenol), 1,1-bis-(5-tert-butyl-4-hydroxy-2-methylphenyl)-butane, 2,6-bis-(3-tert-butyl-5-methyl-2-hydroxybenzyl)-4-methylphenol, 1,1,3tris-(5-tert-butyl-4-hydroxy-2-methylphenyl)-butane, 1,1-bis-(5-tert-butyl-4-hydroxy-2-methylphenyl)-3-n-dodecylmercaptobutane, ethylene glycol-bis-[3,3-bis-(3'-tert-butyl-4'-hydroxyphenyl)-butyrate], bis-(3-tert-butyl-4-hydroxy-5-methylphenyl)-dicyclopentadiene, bis-[2-(3'-tert-butyl-2'-hydroxy-5'-methyl-benzyl)-6-tert-butyl-4-methyl-phenyl]terephthalate.

1.5 Benzyl compounds, for example 1,3,5-tris-(3,5-di-tert-butyl-4-hydroxybenzyl)-2,4,6-trimethylbenzene, bis-(3,5-di-tert-butyl-4-hydroxybenzyl)-sulfide, isooctyl 3,5-di-tert-butyl-4-hydroxybenzyl-mercaptoacetate, bis-(4-tert-butyl-3-hydroxy-2,6-dimethylbenzyl)-dithioterephthalate, 1,3,5-tris-(3,5-di-tert-butyl-4-hydroxybenzyl) isocyanurate, 1,3,5-tris-(4-tert-butyl-3-hydroxy-2,6-dimethylbenzyl) isocyanurate, dioctadecyl 3,5-di-tert-butyl-4-hydroxybenzyl-phosphinate, Ca salt of 3,5-di-tert-butyl-4-hydroxybenzyl-phosphonic acid monoethyl ester, 1,3,5-tris-(3,5-dicyclohexyl-4-hydroxybenzyl) isocyanurate.

1.6. Acylaminophenols, for example 4-hydroxylauranilide, 4-hydroxystearanilide, 2,4-bis-(octylmercapto)-6-(3,5-di-tert-butyl-4-hydroxyanilino)-s-triazine, octyl N-(3,5-di-tert-butyl-4-hydroxyphenyl)-carbamate.

1.7. Esters of β-(3,5-di-tert-butyl-4-hydroxyphenyl)-propionic acid with mono- or polyhydric alcohols, for example with methanol, octadecanol, 1,6-hexanediol, neopentyl glycol, thiodiethylene glycol, diethylene glycol, triethylene glycol, pentaerythritol, tris-hydroxyethyl) isocyanurate, N,N'-bis-(hydroxyethyl)-oxalamide.

1.8. Esters of β-(5-tert-butyl-4-hydroxy-3-methylphenyl)propionic acid with mono- or polyhydric alcohols, for example with methanol, octadecanol, 1,6-hexanediol, neopentyl glycol, thiodiethylene glycol, diethylene glycol, triethylene glycol, pentaerythritol, tris-(hydroxyethyl) isocyanurate, N,N'-bis-(hydroxyethyl)-oxalamide.

1.9. Esters of β-(3,5-dicyclohexyl-4-hydroxyphenyl)-propionic acid with mono- or polyhydric alcohols, for example with methanol, octadecanol, 1,6-hexanediol, neopentyl glycol, thiodiethylene glycol, diethylene glycol, triethylene glycol, pentaerythritol, tris-(hydroxyethyl) isocyanurate, N,N'-bis-(hydroxyethyl)-oxalamide.

1.10. Amides of β-(3,5-di-tert-butyl-4-hydroxyphenyl)-propionic acid, for example N,N'-bis-(3,5-di-tert-butyl-4-hydroxyphenylpropionyl)-hexamethylenediamine, N,N'-bis-(3,5-di-tert-butyl-4-hydroxyphenylpropionyl)-tri-methylenediamine, N,N'-bis-(3,5-di-tert-butyl-4-hydroxyphenylpropionyl)-hydrazine.

2. UV absorbers and light stabilizers 2.1. 2-(2'-Hydroxyphenyl)-benzotriazoles, for example the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-sec-butyl-5'-tert-butyl, 4'-octoxy, 3',5'-di-tert-amyl, 3',5'-bis-(α,α-dimethylbenzyl) derivative.

2.2. 2-Hydroxybenzophenones, for example the 4-hydroxy, 4-methoxy, 4-octoxy, 4-decyloxy, 4-dodecyloxy, 4-benzyloxy, 4,2', 4'-trihydroxy, 2'-hydroxy-4,4'-dimethoxy derivative.

2.3. Esters of substituted or unsubstituted benzoic acids, for example 4-tert-butyl-phenyl salicylate, phenyl salicylate, octyphenyl salicylate, dibenzoylresorcinol, bis-(4-tert-butylbenzoyl)-resorcinol, benzoylresorcinol, 2,4-di-tert-butylphenyl 3,5-di-tert-butyl-4-hydroxybenzoates, hexadecyl 3,5-di-tert-butyl-4-hydroxybenzoates.

2.4. Acrylates, for example ethyl or isoocrtyl α-cyano-β,β-diphenylacrylates, methyl α-carbomethoxycinnamates, methyl or butyl α-cyano-β-methyl-p-methoxy-cinnamates, methyl α-carbomethoxy-p-methoxycinnamates, N-(β-carbomethoxy-β-cyanovinyl)-2-methyl-indoline.

2.5. Nickel compounds, for example nickel complexes of 2,2'-thio-bis-[4-(1,1,3,3-tetramethylbutyl) -phenol], such as the 1:1 or the 1:2 complex, if desired with additional ligands, such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl of ethyl ester, nickel complexes of ketoximes, such as of 2-hydroxy-4-methyl-phenyl-undecylketoxime, nickel complexes of 1-phenyl-4-lauroyl-5-hydroxypyrazole, if desired with additional ligands.

2.6. Sterically hindered amines, for example bis-(2,2,6,6-tetramethylpiperidyl) sebacate, bus-(1,2,2,6,6-pentamethylpiperidyl) sebacate, bis-1,2,2,6,6-pentamethylpiperidyl) n-butyl-3,5-di-tert-butyl-4-hydroxybenzylmalonate, the condensation product from 1-hydroxyethyl-2,2,6,6-tetramethyl-4-hydroxypiperidine and succinic acid, the condensation product from N,N'-bis-(2,2,6,6-tetramethyl-4-piperidyl)-hexamethylenediamine and 4-tert-octylaminol-2,6-dichloro-1,3,5-s-triazine, tris-(2,2,6,6-tetramethyl-4-piperidyl) nitrilotriacetate, tetrakis-(2,2,6,6-tetramethyl-4piperidyl) 1,2,3,4-butanetetraoate, 1,1'-(1,2-ethanediyl)-bis-(3,3,5,5-tetramethyl-piperazinone).

2.7. Oxalamides, for example 4,4'-di-octyloxy-oxanilide, 2,2'-di-octyloxy-5,5'-di-tert-butyl-oxanilide, 2,2'-di-dodecyloxy-5,5'-di-tert-butyl-oxanalide, 2-ethoxy-2'-ethyl-oxanilide, N,N'-bis-(3-dimethylamino-propyl)-oxalamide, 2-ethoxy-5-tert-butyl-2'-ethoxanilide and its mixture with 2-ethoxy-2'-ethyl-5,4'-di-tert-butyl-oxanilide, mixtures of o- and p-methoxy and of o- and p-ethoxy di-substituted oxanilides.

2.8. 2-(2-Hydroxyphenyl)-1,3,5-triazines, for example 2,4,6-tris-(2-hydroxy-4-octyloxyphenyl)-1,3,5-triazine, 2-(2-hydroxy-4-octyloxyphenyl)-4,6-bis(2,4dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine.

3. Metal deactivators, for example N,N'-diphenyloxalamide, N-salicylal-N'-salicyloylhydrazine, N,N'-bis-(salicyloyl)-hydrazine, N,N'-bis-(3,5-di-tert-butyl-4-hydroxyphenylpropionyl)-hydrazine, 3-salicyloylamino-1,2,4-triazole, bis-(benzylidene)-oxalic acid dihydrazide.

4. Phosphites and phosphonites, for example triphenyl phosphite, diphenylalkyl phosphites, phenyldialkyl phosphites, tris-(nonylphenyl) phosphite, trilauryl phosphite, trioctadecyl phosphite, distearyl-pentaerythritol diphosphite, tris-(2,4-di-tert-butylphenyl) phosphite, diisodecylpentaerythritol diphosphite, bis-(2,4-di-tert-butylphenyl)-pentaerythritol diphosphite, tristearyl-sorbitol triphosphite, terakis-(2,4-di-tert-butylphenyl)-4,4'-biphenylene diphosphonite, 3,9-bis-(2,4-di-tert-butylphenoxy)-2,4,8,10-tetraoxa-3,9-diphosphaspiro[5.5]undecane.

5. Peroxide-destroying compounds, for example esters of β-thio-dipropionic acid, for example the lauryl, stearyl, myristyl or tridecyl esters, mercaptobenzimidazole, the zinc salt of 2-mercaptobenzimidazole, zinc dibutyl-dithiocarbamate, dioctadecyl disulfide, pentaerythritol-tetrakis-(β-dodecylmercapto) propionate.

6. Polyamide stabilizers, for example copper salts in combination with iodides and/or phosphorus compounds and salts of divalent manganese.

7. Basic co-stabilizers, for example melamine, polyvinylpyrrolidone, dicyandiamide, triallyl cyanurate, urea derivatives, hydrazine derivatives, amines, polyamides, polyurethanes, alkali metal and alkaline earth metal salts of higher fatty acids, for example Ca stearate, Zn stearate, Mg stearate, Na ricinoleate, K palmitate, antimony pyrocatecholate or tin pyrocatecholate.

8. Nucleating agents, for example 4-tert-butylbenzoic acid, adipic acid, diphenylacetic acid.

9. Fillers and reinforcing agents, for example calcium carbonate, silicates, glass fibers, asbestos, talc, kaolin, mica, barium sulfate, metal oxides and hydroxides, soot, graphite.

10. Various additives, for example softeners, lubricants, emulsifiers, pigments, optical brighteners, flame retardants, antistatics, propellants.

Synergistic effects may occur with the additional use of such costabilizers, which is the case in particular with the additional use of UV absorbers.

When the compounds according to the invention are used as stabilizers for photographic materials, use in photographic layers, for example on films or photographic papers, is in particular of interest.

Some of the compounds according to the invention may also be used as intermediates in the preparation of other compounds according to the invention. This applies in particular to compounds which have chlorine atoms on the triazine ring. Those compounds which contain no chlorine atoms on the triazine radicals are preferred as stabilizers.

The following examples illustrate the preparation and use of the compounds according to the invention in more detail. In these examples, parts and percentages are by weight. The temperatures are given in degrees Celsius.

EXAMPLE 1

2,4-Dichloro-6-(2,2,6,6-tetramethylpiperidinl-1-yl)-1,3,5-triazine.

92.2 g of cyanuric chloride and 142.6 g of 2,2,6,6-tetramethylpiperidine are stirred for 10 hours at 120° in 400 ml of xylene. After cooling to room temperature, the solution is filtered off from the 2,2,6,6-tetramethylpiperidine hydrochloride formed and the latter is washed with 100 ml of xylene. The yellow to brownish xylene solution is washed three times, each with 100 ml of water, dried over sodium sulfate, stirred for 10 minutes with 5 g of Tonsil Optimum (bleaching earth) and 5 g of animal charcoal, clarified and evaporated in vacuo. The residue obtained is optimally recrystallized from 300 ml of hexane with the addition of 3 g of Tonsil. 2,4-Dichloro-6-(2,2,6,6-tetramethylpiperidinl-1-yl)-1,3,5-triazine is obtained as colorless crystals having a melting point of 129°.

EXAMPLE 2

2,4-Dichloro-6-(2,2,6,6-tetramethyl-4-benzoyloxy-piperidin-1-yl)-1,3,5-triazine.

46.1 g of cyanuric chloride and 136.0 g of 2,2,6,6-tetramethyl-4-benzoyloxypiperidine are reacted in 300 ml of xylene as described in Example 1 and worked up. After recrystallization from isopropanol, 2,4-dichloro-6-(2,2,6,6-tetramethyl-4-benzoyloxy-piperidin-1-yl)-1,3,5-triazine are obtained as colorless crystals having a melting point of 145°.

EXAMPLE 3

2-Chloro-4-ethylamino-6-(2,2,6,6-tetramethylpiperidin-1-yl)-1,3,5-triazine.

15 g of a 70% aqueous ethylamine solution is added to 28.9 g of 2,4-dichloro-6-(2,2,6,6-tetramethylpiperidin-1-yl)-1,3,5-triazine (prepared according to Example 1) in 250 ml of ethanol at room temperature. The temperature climbs rapidly to about 35°. The mixture is subsequently stirred at 55° for 12 hours, 25 ml of water are added and the mixture is cooled to 5°. The resulting precipitate is filtered off, washed with 200 ml of water and dried. 2-Chloro-4-ethylamino-6-(2,2,6,6-tetramethylpiperidin-1-yl)-1,3,5-triazine is obtained by crystallization from acetonitrile as colorless crystals having a melting point of 148°.

EXAMPLE 4

2-Chloro-4-diethylamino-6-(2,2,6,6-tetramethyl-piperidin-1-yl)-1,3,5-triazine. 15 g of diethylamine is used in place of the ethylamine solution and the procedure is otherwise as described in Example 3. 2-Chloro-4-diethylamino-6-(2,2,6,6-tetramethylpiperidin-1-yl)-1,3,5-triazine is obtained as a colorless substance having a melting point of 77°.

EXAMPLE 5

2,4-Bis-isopropylamino-6-(2,2,6,6-tetramethylpiperidin-1-yl)-1,3,5-triazine.

43.4 g of 2,4-dichloro-6-(2,2,6,6-tetramethylpiperidin-1-yl)-1,3,5-triazine are heated in an autoclave to 160° for 8 hours with 39.0 g of isopropylamine in 200 ml of xylene. After cooling to room temperature, the autoclave contents are washed three times, each with 100 ml of water, and the yellowish xylene solution is dried over sodium sulfate, stirred for 10 minutes with 5 g of Tonsil Optimum (bleaching earth), filtered and evaporated. The 2,4-bis-isopropylamino-6-(2,2,6,6-tetramethyl-piperidin-1-yl)-1,3,5-triazine obtained is a slightly yellowish resin which could not be crystallized.

EXAMPLE 6

2,4-Bis-dibutylamino-6-(2,2,6,6-tetramethylpiperidin-1-yl)-1,3,5-triazine.

57.8 g of 2,4-dichloro-6-(2,2,6,6-tetramethylpiperidin-1-yl)-1,3,5-triazine are suspended in 200 ml of xylene at room temperature. 25.8 g of dibutylamine are added dropwise to this during the course of 15 minutes, the temperature climbing to 40°. A solution of 8.87 g of sodium hydroxide in 40 ml of water is added to the reaction mixture in about 15 minutes and it is subsequently stirred at 60° for 2 hours. The aqueous phase is then separated off and 28.4 g of dibutylamine and a solution of 9.6 g of sodium hydroxide in 20 ml of water is added to the clear organic phase. The mixture is then heated in a water separator until an internal temperature of about 135° is reached and is then stirred for 12 hours at this temperature. The contents of the flask are cooled to 90°, a solution of 3 g of sodium hydroxide in 100 ml of water is added and the mixture is vigorously stirred at 90° for 30 minutes. The aqueous phase is then separated off, the xylene solution is washed five times, each with 100 ml of water, and evaporated in vacuo. The yellowish, oily residue is distilled in a high vacuum. 2,4-Bis-dibutylamino-6-(2,2,6,6-tetramethylpiperidin-1-yl)-1,3,5-triazine is obtained as a colorless oil having a boiling point of 173° at 6.5 Pa.

EXAMPLE 7

2,4-Dimorpholino-6-(2,2,6,6-tetramethylpiperidin-1-yl)-1,3,5-triazine.

36.6 g of morpholine (1st portion: 17.4 g; 2nd portion: 19.2 g) are used in place of dibutylamine and the procedure is otherwise as described in Example 6. 2,4-Dimorpholino-6-(2,2,6,6-tetramethylpiperidinl-1-yl)-1,3,5-triazine is obtained, after crystallization from ethanol, having a melting point of 147°–48°.

EXAMPLE 8

2,4-Bis-butylamino-6-(2,2,6,6-tetramethyl-4-benzoyloxypiperidin-1-yl)-1,3,5triazine.

20.5 g of 2,4-dichloro-6-(2,2,6,6-tetramethyl-4-benzoyloxypiperidin-1-yl)-1,3,5-triazine (prepared according to Example 2) are stirred in 200 ml of xylene with 8.0 g of n-butylamine at reflux for 4 hours. 4.4 g of pulverized sodium hydroxide are added to the reaction mixture and it is stirred for a further 15 hours at reflux. The contents of the flask are cooled to room temperature and, after addition of 100 ml of water, are vigorously stirred until the precipitated salt has completely gone into solution. The aqueous phase is separated off, and the xylene solution is washed three times, each with 100 ml of water, and evaporated in vacuo. The oily residue is dried at 100° and 13 Pa. 2,4-Bis-butylamino-6-(2,2,6,6-tetramethyl-4-benzoylpiperidin-1-yl)-1,3,5-triazine is obtained as a yellowish viscous material.

EXAMPLE 9

2,4-Bis-butylamino-6-(2,2,6,6-tetramethyl-4-hydroxypiperidin-1-yl)-1,3,5-triazine.

10 g of 2,4-bis-butylamino-6-(2,2,6,6-tetramethyl-4-benzoyloxypiperidin-1-yl)1,3,5-triazine (prepared according to Example 8) are heated at reflux for 6 hours with 50 ml of methanol and 50 ml of twenty per cent sodium hydroxide solution. The methanol is distilled off from the reaction mixture in vacuo. 100 ml of toluene and 50 ml of water are added to the residue, shaken thoroughly, the aqueous phase is separated off and the toluene solution is washed three times, each with 50 ml of water. After evaporating the toluene solution, 2,4-bis-butylamino-6-(2,2,6,6-tetramethyl-4-hydroxypiperidin-1yl)-1,3,5-triazine is obtained as a yellowish viscous material. Colorless crystals which melt at 90° C. are obtained by crystallization from acetonitrile.

EXAMPLE 10

2,4-Dichloro-6-(2,2,6,6-tetramethyl-4-hexyloxypiperidin-1-yl)-1,3,5-triazine.

62.7 g of 4-hexyloxy-2,2,6,6-tetramethylpiperidine are added with stirring to a solution of 23.9 g of cyanuric chloride in 100 ml of toluene. The mixture is subsequently heated to 80° for 24 hours. A white precipitate of the piperidine hydrochloride is formed during this. After cooling, the precipitate is filtered off, and the toluene solution is washed a number of times using 2N hydrochloric acid, dried over $Na_2SO_4$ and evaporated. The residue is recrystallized from acetonitrile. The product obtained melts at 49°–51°.

EXAMPLE 11

2,4-Dimorpholino-6-(2,2,6,6-tetramethyl-4-hexyloxypiperidin-1-yl)-1,3,5-triazine.

9.7 g of the product from Example 10 are heated under reflux for 3 hours with 50 ml of morpholine. The orange reaction mixture is poured into water. The crude product precipitating during this is dissolved in ethyl acetate and purified chromatographically on an $SiO_2$ column. The purified product is a viscous material.

Analysis: Calc.: C: 63.64%; H: 9.44%; N: 17.12%; Found: C: 63.64%; H: 9.29%; N: 17.08%.

EXAMPLE 12

Diisobutylamine is used in place of the morpholine in Example 11 and the procedure is otherwise exactly the same as in Example 11. 2,4-Bis-(diisobutylamino)-6-(2,2,6,6-tetramethyl-4-hexyloxypiperidin-1-yl)-1,3,5-triazine is obtained as a viscous liquid.

Analysis: Calc.: C: 75.12%; H: 12.35%; N: 10.51%; Found: C: 75.36%; H: 12.08%; N: 10.54%.

EXAMPLE 13

Dibutylamine is used instead of the morpholine in Example 11 and the procedure is otherwise as described in Example 11. 2,4-Bis-(dibutylamino)-6-(2,2,6,6-tetramethyl-4-hexyloxypiperidin-1-yl)-1,3,5-triazine is obtained as a viscous material.

Analysis: Calc.: C: 71.02%; H: 1.57%; N: 14.61%; Found: C: 71.09%; H: 10.96%; N: 14.69%.

EXAMPLE 14

Polycondensate of 2,4-dichloro-6-(2,2,6,6-tetramethylpiperidin-1-yl)-1,3,5-triazine and hexamethylenediamine.

A solution of 10.5 g (90 mmol) of hexamethylenediamine in 50 ml of xylene is slowly added dropwise at 100° with stirring to a solution of 12.4 g (43 mmol) of 2,4-dichloro-6-(2,2,6,6-tetramethylpiperidinl-1-yl)-1,3,5-triazine in 50 ml of xylene and the reaction mixture is stirred under reflux for 22 hours. After cooling the mixture is filtered, the filtrate is washed twice with 50 ml of water and sufficient hexane is added until no further precipitation takes place. The precipitate is filtered off, and the filtrate is washed three times with 50 ml of water, dried over $Na_2SO_4$ and evaporated. The residue is dried in vacuo at 50°. A resinous polymer of molecular weight $\overline{M}_n = 1029 / \overline{M}_w = 1545$ (gel permeation chromatography) is obtained.

EXAMPLE 15

2,4-Dichloro-6-(1,3,8-triaza-2,4-dioxo-3,7,7,9,9-pentamethylspiro[4,5]dec-1-yl)-1,3,5-triazine.

A solution of 35.1 g (0.19 mol) of cyanuric chloride in 200 ml of xylene is added dropwise at 0°–5° with stirring to a solution of 90.9 g (0.38 mol) of 1,3,8-triaza-2,4-dioxo-3,7,7,9,9-pentamethyl-spiro[4,5]decane in 500 ml of xylene. The mixture is subsequently heated to reflux for 24 hours. After cooling, the precipitate is filtered off and the filtrate is washed, first with water which has been adjusted to pH 5 with acetic acid, then with an $Na_2CO_3$ solution and finally with water. The xylene solution is filtered, dried over $Na_2SO_4$ and evaporated in vacuo. The residue is recrystallized from 70 ml of acetonitrile. A brownish powder which melts at 237°–242° is obtained.

Analysis: Calc.: C: 46.52%; H: 21.70%; N: 5.21%; Found: C: 46.40%; H: 21.85%; N: 5.22%.

EXAMPLE 16

2,4-Dimorpholino-6-(1,3,8-triaza-2,4-dioxo-3,7,7,9,9-pentamethyl-spiro[4,5]dec-1-yl)-1,3,5-triazine.

5.4 g of morpholine are slowly added with ice cooling to 6 g of the product from Example 15. A further 30 ml of morpholine are then added and the reaction mixture is heated to reflux. After heating to reflux for 38 hours, the mixture is cooled and 50 ml of water is added. The precipitate depositing during this is filtered off, washed with water and dried. The product is recrystallized from methylene chloride/hexane. A white powder which melts at 319°–321° with decomposition is obtained.

Analysis: Calc.: C: 56.54%; H: 22.93%; N: 7.43%; Found: C: 56.55%; H: 22.88%; N: 7.53%.

EXAMPLE 17

2,4-Dichloro-6-(4,4-ethylenedioxy-2,2,6,6-tetramethylpiperidin-1yl)-1,3,5-triazine.

A solution of 55.3 g (0.3 mol) of cyanuric chloride in 300 ml of xylene is added dropwise with stirring and cooling to 0°–5° to a solution of 119.6 g (0.6 mol) of 4,4-ethylenedioxy-2,2,6,6-tetramethylpiperidine in 100 ml of xylene. The mixture is subsequently heated to reflux and kept at boiling point for 26 hours. After addition of 150 ml of xylene, the mixture is allowed to cool and the precipitate is filtered off. The filtrate is evaporated in vacuo. The residue is recrystallized from 300 ml of acetonitrile. The product obtained is a brownish powder which melts at 169°–172°.

Analysis: Calc.: C: 48.43%; H: 16.41%; N: 5.81%; Found: C: 48.49%; H: 16.20%; N: 5.66%.

EXAMPLE 18

2-Chloro-4-diisopropylamino-6-(4,4-ethylenedioxy-2,2,6,6-tetramethylpiperidin-1-yl)-1,3,5-triazine.

26.1 g (258 mmol) of diisopropylamine are added with stirring to a solution of 29.9 g (86 mmol) of the product from Example 17 in 100 ml of toluene. The mixture is heated to reflux and kept at this temperature for 24 hours. After cooling, a solution of 4.1 g of NaOH in 21 ml of water is added. The solid product is filtered off and recrystallized from 25 ml of toluene. A yellowish powder which melts at 179°–184° is obtained.

Analysis: Calc.: C: 58.31%; H: 17.00%; N: 8.32%; Found: C: 58.34%; H: 16.97%; N: 8.42%.

EXAMPLE 19

2-Octylamino-4-diisopropylamino-6-(4,4-ethylenedioxy-2,2,6,6-tetramethylpiperidin-1-yl)-1,3,5-triazine.

15 g (36.4 mmol) of the product from Example 18 are heated to 120° for 3 hours together with 30 ml of octylamine. After cooling, 40 ml of water are added and the mixture is extracted three times using 30 ml of methylene chloride. The $CH_2Cl_2$ solution is washed with water, dried over $Na_2SO_4$ and evaporated. The oily residue is dissolved in hexane/acetone and purified chromatographically on an $SiO_2$ column. The main fraction is a viscous material.

Analysis: Calc.: C: 66.63%; H: 16.65%; N: 10.38%; Found: C: 66.76%; H: 16.48%; N: 10.30%.

EXAMPLE 20

2,4-Dimorpholino-6-(4,4-ethylenedioxy-2,2,6,6-tetramethylpiperidinl-1-yl)-1,3,5-triazine.

40 g of morpholine are added with ice cooling to 40 g of the product from Example 17. After addition of a further 100 g of morpholine, the mixture is slowly heated to 130° with stirring and refluxed for 6 hours. After cooling to room temperature, 150 ml of water are added. The precipitate formed is filtered off, washed with water and recrystallized from acetonitrile. The product obtained melts at 216°–221°.

Analysis: Calc.: C: 58.91%; H: 18.74%; N: 8.09%; Found: C: 58.92%; H: 18.88%; N: 8.01%.

EXAMPLE 21

2,4-Dimorpholino-6-(4-oxo-2,2,6,6-tetramethylpiperidin-1-yl)-1,3,5-triazine.

29.6 g of the product from Example 20 are introduced with stirring into 200 ml of a solution of 1.26 g of p-toluenesulfonic acid in a 1:1 mixture of tetrahydrofuran and water. After addition of a further 60 ml of tetrahydrofuran, the mixture is warmed to 50° for 5 hours. 1.26 g of toluenesulfonic acid is then again added and the mixture is stirred at 50° for a further 14 hours. After cooling, the mixture is extracted five times using 50 ml of methylene chloride. The combined $CH_2Cl_2$ solutions are washed with water, dried over $Na_2SO_4$ and evaporated. The residue is recrystallized from 80 ml of acetonitrile. The white crystals obtained melt at 188°–192°.

Analysis: Calc.: C: 59.38%; H: 20.78%; N: 7.97%; Found: C: 59.58%; H: 20.57%; N: 7.93%.

EXAMPLE 22

2,4-Dichloro-6-(2,2,6,6-tetramethyl-4-dodecyloxypiperidin-1-yl)-1,3,5-triazine.

An identical mole equivalent amount of 4-dodecyloxy-2,2,6,6-tetramethylpiperidine is used in place of the 4-hexyloxy-2,2,6,6-tetramethylpiperidine described in Example 10 and the procedure is otherwise exactly the same as described in Example 10. The above compound is obtained as a slightly yellowish oil.

Analysis: Calc.: C: 60.88%; H: 8.94%; N: 11.83%; Cl: 14.97%; Found: C: 61.14%; H: 8.69%; N: 11.62%; Cl: 14.66%.

EXAMPLE 23

2,4-Dichloro-6-(2,2,6,6-tetramethyl-4-allyloxypiperidin-1-yl)-1,3,5-triazine.

An identical mole equivalent amount of 4-allyloxy-2,2,6,6-tetramethylpiperidine is used in place of the 4-hexyloxy-2,2,6,6-tetramethylpiperidine described in Example 10 and the procedure is otherwise exactly the same as described in Example 10. The above compound is obtained as a crystalline product which can be recrystallized from ethanol. The product obtained melts at 53°–55° C.

EXAMPLE 24

Di-(2-ethyl-hexy)-amine is used instead of the morpholine in Example 11 and the procedure is otherwise exactly the same as described in Example 11. 2,4Bis[di-(2-ethyl-hexyl)-amino]-6-(2,2,6,6-tetramethyl-4-hexyloxypiperidin-1-yl)-1,3,5-triazine is obtained as a yellowish oil.

Analysis: Calc.: C: 75.12%; H: 12.35%; N: 10.51%; Found: C: 75.36%; H: 12.08%; N: 10.54%.

EXAMPLE 25

4-Butylamino-2,2,6,6-tetramethylpiperidine is used in place of the morpholine in Example 11 and the procedure is otherwise exactly the same as described in Example 11. 2,4-Bis-[N-(2,2,6,6-tetramethylpiperidin-4-yl)-butylamino]-6-(2,2,6,6-tetramethyl-4-hexyloxypiperidin-1-yl)-1,3,5-triazine is obtained as white crystals which can be recrystallized from acetonitrile. M.p.: 135°–137° C.

EXAMPLE 26

2-Chloro-4-diisopropylamino-6-(2,2,6,6-tetramethylpiperidin-4-hexyloxypiperidin-1-yl)-1,3,5-triazine.

The identical mole equivalent amount of the compound prepared in Example 10 is used in place of 2,4-dichloro-6-(2,2,6,6-tetramethylpiperidinl-1-yl)-1,3,5-triazine and a mole equivalent amount of diisopropylamine in place of an ethylamine solution in Example 3 and the procedure is otherwise exactly the same as described in Example 3. The above compound is obtained as a colorless oil.

Analysis: Calc.: C: 63.47%; H: 9.76%; N: 15.42%; Cl: 7.80%; Found: C: 63.64%; H: 9.73%; N: 15.47%; Cl: 7.80%.

EXAMPLE 27

N,N'-bis-[4-diisopropylamino-6-(4,4-ethylenedioxy-2,2,6,6-tetramethylpiperidin-1-yl)-triazin-2-yl]-hexamethylenediamine.

2.07 g (17 mmol) of 1,6-diamino-hexane and a solution of 1.36 g (34 mmol) of sodium hydroxide in 4 ml of water are added at 100° to 14 mg (34 mmol) of the product from Example 18 in 40 ml of xylene. The internal temperature is increased to 135° C. while distilling off water. After 21 hours, 0.1 g of 1,6-diamino-hexane is added and allowed to react further during the course of 6 hours at the same temperature. The mixture is allowed to cool to 70° C., 0.26 g of sodium hydroxide, dissolved in 7.4 ml of water, is added, the mixture is stirred for 30 minutes and the two phases are separated. The organic phase is washed three times with water, dried over $Na_2SO_4$ and evaporated. The residue is dissolved in chloroform and purified chromatographically on an $SiO_2$ column. The above product which melts at 145°–147° after drying well is obtained as the main fraction.

Analysis: Calc.: C: 63.71%; H: 9.53%; N: 19.38%; Found: C: 64.13%; H: 9.52%; N: 19.01%.

EXAMPLE 28

2,4-Dichloro-6-(1,3,8-triaza-2,4-dioxo-3-dodecyl-7,7,9,9-tetramethyl-spiro[4,5]dec-1-yl)-1,3,5-triazine.

A mole equivalent amount of 1,3,8-triaza-2,4-dioxo-3-dodecyl-7,7,9,9-tetramethyl-spiro[4,5]-decane is used in place of the 1,3,8-triaza-2,4-dioxo-3,7,7,9,9-pentamethyl-spiro[4,5]decane described in Example 15 and the procedure is otherwise exactly the same as given in Example 15. The above product which melts at 109°–115° is obtained after the product produced has been dissolved in hexane/acetone and purified chromatographically on an $SiO_2$ column.

EXAMPLE 29

2,4-Dimorpholino-6-(1,3,8-triaza-2,4-dioxo-3-dodecyl-7,7,9,9-tetramethyl-spiro[4,5]dec-1-yl)-1,3,5-triazine.

A mole equivalent amount of the 2,4-dichloro-6-(1,3,8-triaza-2,4-dioxo-3-dodecyl-7,7,9,9-tetramethyl-spiro[4,5]dec-1-yl)-1,3,5-triazine described in Example 28 is used in place of the 2,4-dichloro-6-(1,3,8-triaza-2,4-dioxo-3,7,7,9,9-pentamethyl-spiro[4,5]dec-1-yl)-1,3,5-triazine described in Example 15 and the procedure is otherwise the same as given in Example 16. The above product which melts at 185°–188° is obtained.

Analysis: Calc.: C: 63.52%; H: 9.09%; N: 17.43%; Found: C: 63.39%; H: 9.20%; N: 17.38%.

EXAMPLE 30

2,4-Bis-N-butylmethylamino-6-(1,3,8-triaza-2,4-dioxo-3-dodecyl-7,7,9,9-tetramethyl-spiro[4,5]dec-1-yl)-1,3,5-triazine.

The procedure is the same as given in Example 29, but a mole equivalent amount of N-butylmethylamine is used in place of morpholine. The above compound, which melts at 93°–96°, is obtained.

Analysis: Calc.: C: 67.25%; H: 10.35%; N: 17.43%; Found: C: 67.05%; H: 10.26%; N: 17.55%.

EXAMPLE 31

2,4-Bis-N-butylmethylamino-6-(4,4-ethylenedioxy-2,2,6,6-tetramethylpiperidin-1-yl)-1,3,5-triazine.

24 ml of N-butylmethylamine are added with ice cooling to 15 g of the product from Example 17. After addition of a further 50 ml of N-butylmethylamine, the mixture is slowly heated to 88° with stirring and refluxed for 24 hours. After cooling to room temperature, 150 ml of water are added and some HCl until the pH is 2. The mixture is then extracted by shaking with methylene chloride; the organic phase is dried over $Na_2SO_4$, evaporated and dried. The product of the above formula is produced as a slightly yellow oil during this.

Analysis: Calc.: C: 64.25%; H: 9.89%; N: 18.73%; Found: C: 64.58%; H: 10.17%; N: 18.51%.

EXAMPLE 32

2,4-Bis-dibutylamino-6-(4,4-ethylenedioxy-2,2,6,6-tetramethylpiperidin-1-yl)-1,3,5-triazine.

A mole equivalent amount of dibutylamine is used in place of the N-butylmethylamine described in Example 31 and the procedure is otherwise exactly the same as given in Example 31, the product finally being dissolved using toluene/hexane and purified chromatographically on an $SiO_2$ column. The above product is obtained as a colorless oil.

Analysis: Calc.: C: 67.63%; H: 10.59%; N: 15.77%; Found: C: 67.27%; H: 10.37%; N: 15.45%.

EXAMPLE 33

2,4-Bis-N-butylmethylamino-6-(4-oxo-2,2,6,6-tetramethylpiperidin-1-yl)-1,3,5-triazine.

A mole equivalent amount of the 2,4-bis-N-butylmethylamino-6-(4,4-ethylenedioxy-2,2,6,6-tetramethylpiperidin-1-yl)-1,3,5-triazine described in Example 31 is used in place of the 2,4-dimorpholino-6-(4,4-ethylenedioxy-2,2,6,6-tetramethylpiperidin-1-yl)-1,3,5-triazine described in Example 21 and the procedure is otherwise exactly the same as given in Example 31, the product finally being dissolved in hexane/acetone and purified chromatographically on an $SiO_2$ column. The above product is obtained as a colorless oil.

Analysis: Calc.: C: 65.31%; H: 9.97%; N: 20.77%; Found: C: 65.11%; H: 9.86%; N: 20.53%;

EXAMPLE 34

2,4-Dimorpholino-6-(4-hydroxy-2,2,6,6-tetramethylpiperidin-1-yl)-1,3,5-triazine.

5 g of 2,4-dimorpholino-6-(4-oxo-2,2,6,6-tetramethylpiperidin-1-yl)-1,3,5-triazine (product from Example 21) are hydrogenated in 100 ml of tetrahydrofuran at 60° and a pressure of 100 bar until the reaction stops using Raney nickel as the catalyst. The reaction mixture is filtered, the solution is evaporated and the residue is recrystallized from 20 ml of toluene. The above substance is produced as white crystals which melt at 202°–204°.

Analysis: Calc.: C: 59.09%; H: 8.43%; N: 20.67%; Found: C: 59.27%; H: 8.35%; N: 20.54%.

EXAMPLE 35

2-Chloro-4-(1-acetyl-2,2,6,6-tetramethylpiperidin-4-oxy)-6-(2,2,6,6-tetramethylpiperidin-1-yl)-1,3,5-triazine.

43.4 g of 2,4-dichloro-6-(2,2,6,6-tetramethylpiperidin-1-yl)-1,3,5-triazine (product from Example 1) are dissolved in 175 ml of toluene, after which 42.1 g of pulverized KOH, 1 g of potassium carbonate and 3.4 g of tetrabutylammonium hydrogen sulfate are added. A solution of 29.9 g of 1-acetyl-2,2,6,6-tetramethyl-4-hydroxy-piperidine in 110 ml of toluene is then added dropwise, the internal temperature being maintained at 10° using an ice bath. After stirring for 3.5 hours, 100 ml of water are added. The phases are separated, and the organic phase is washed with water, dried over $Na_2SO_4$ and evaporated. After recrystallizing from hexane, the above product is produced as a white powder which melts at 114°–116° C.

Analysis: Calc.: C: 61.11%; H: 8.47%; N: 15.49%; Found: C: 61.46%; H: 8.50%; N: 15.27%.

EXAMPLE 36

2-Chloro-4-(1-hydroxyl-2,2,6,6-tetramethylpiperidin-4-oxy)-6-( 2,2,6,6-tetramethylpiperidin-1-yl)-1,3,5-triazine.

A mole equivalent amount of 1-hydroxyl-2,2,6,6-tetramethyl-4-hydroxypiperidine is used in place of the 1-acetyl-2,2,6,6-tetramethyl-4-hydroxypiperidine described in Example 35 and the procedure is otherwise the same as given in Example 35, the product finally being recrystallized from acetonitrile. The above product is obtained as a reddish powder which melts at 152°–153°.

Analysis: Calc.: C: 59.35%; H: 8.30%; N: 16.48%; Found: C: 59.08%; H: 8.29%; N: 16.65%.

Example 37

N,N'-bis-[4-(1-acetyl-2,2,6,6-tetramethylpiperidin-4-oxy)-6-(2,2,6,6-tetramethylpiperidin-1-yl)-triazine-2-yl]-hexamethylenediamine.

60 ml of xylene, 2.6 g of 1,6-diaminohexane and a solution of 1.8 g of sodium hydroxide in 5 ml of water are added to 20 g of 2-chloro-4-(1-acetyl-2,2,6,6-tetramethylpiperidin-4-oxy)-6-(2,2,6,6-tetramethylpiperidin-1-yl)-1,3,5-triazine (product from Example 35). The mixture is then heated, the water being removed by distillation. When the temperature remains constant, the mixture is stirred under reflux for another 24 hours. After cooling, some sodium hydroxide solution is added, after which the phases are separated. The organic phase is dried over Na$_2$SO$_4$ and evaporated. After recrystallization from chloroform/hexane, dissolving the product in chloroform/methanol and chromatographic purification on an SiO$_2$ column, the above product is obtained as a white powder which melts at 201°–202°.

Analysis: Calc.: C: 65.93%; H: 9.58%; N: 17.74%; Found: C: 65.78%; H: 9.73%; N: 17.67%.

EXAMPLE 38

2-Morpholino-4-(1-hydroxyl-2,2,6,6-tetramethylpiperidine-4-oxy)-6-(2,2,6,6-tetramethylpiperidin-1-yl)-1,3,5-triazine.

5 g of 2-chloro-4-(1-hydroxyl-2,2,6,6-tetramethylpiperidin-4-oxy)-6-(2,2,6,6-tetramethylpiperidin-1-yl)-1,3,5-triazine (product from Example 36) are stirred under reflux with 50 ml of morpholine for 3 hours. After cooling to 20°, 200 ml of water are added and the precipitate is filtered off. After recrystallization from petroleum ether, the above product is obtained as reddish crystals which melt at 153°–157°.

Analysis: Calc.: C: 63.13%; H: 9.11%; N: 17.67%; Found: C: 62.94%; H: 9.27%; N: 17.42%.

EXAMPLE 39

2-(1-Acetyl-2,2,6,6-tetramethylpiperidin-4-oxy)-4-(1-hydroxyl-2,2,6,6-tetramethylpiperidin-4-oxy)-6-(2,2,6,6-tetramethylpiperidin-1-yl)-1,3,5-triazine.

4 g of 2-chloro-4-(1-hydroxyl-2,2,6,6-tetramethylpiperidin-4-oxy)-6-(2,2,6,6-tetramethylpiperidin-1-yl)-1,3,5-triazine (product from Example 36) are dissolved in 30 ml of toluene, after which 2.6 g of pulverized KOH, 1 g of potassium carbonate and 0.15 g of tetrabutylammonium hydrogen sulfate are added. 1.95 g of 1-acetyl-2,2,6,6-tetramethyl-4-hydroxypiperidine are added with stirring. The mixture is warmed to 60° for 17 hours. After cooling, 30 ml of water are added. The phases are separated. The organic phase is dried over Na$_2$SO$_4$ and evaporated. After recrystalling from methylene chloride/hexane, dissolving the product in hexane/acetic acid and chromatographic purification on an SiO$_2$ column, the above product, which melts at 175°–176°, is obtained.

Analysis: Calc.: C: 65.38%; H: 9.43%; N: 14.40%; Found: C: 65.42%; H: 9.45%; N: 14.04%.

EXAMPLE 40

2-Chloro-4-[N-bis(2,2,6,6-tetramethylpiperidin-4-yl)-amino]-6-(2,2,6,6-tetramethylpiperidin-1-yl)-1,3,5-triazine.

29.5 g of bis-(2,2,6,6-tetramethylpiperidin-4-yl)-amine, dissolved in 60 ml of toluene, are added to 28.9 g of 2,4-dichloro-6-(2,2,6,6-tetramethylpiperidin-1-yl)-1,3,5-triazine (product from Example 1), dissolved in 130 ml of toluene. After stirring under reflux for 26 hours and allowing to cool, 5.6 g of pulverized KOH and 30 ml of water are added, after which the phases are separated. The organic phase is dried over Na$_2$SO$_4$ and evaporated. After recrystallization from acetonitrile, the above product is obtained as a white powder which melts at 240°–242°.

Analysis: Calc.: C: 65.72%; H: 9.93%; N: 17.88%; Found: C: 65.69%; H: 9.89%; N: 17.69%.

EXAMPLE 41

N,N'-bis-4-[N-bis(2,2,6,6-tetramethylpiperidin-4-yl)-amino]-6-(2,2,6,6-tetramethylpiperidin-1-yl)-triazin-2-yl)-hexamethylenediamine.

A mole equivalent amount of the product described under Example 40 is used in place of the 2-chloro-4-(1-acetyl-2,2,6,6-tetramethylpiperidin-4-oxy)-6-(2,2,6,6-tetramethylpiperidin-1-yl)-1,3,5-triazine described in Example 37 and the procedure is otherwise the same as described in Example 37. The above product is obtained as a white powder which melts at 216°–218°.

Analysis: Calc.: C: 69.55%; H: 10.79%; N: 19.66%; Found: C: 69.43%; H: 10.67%; N: 19.44%.

EXAMPLE 42

Compound of the formula

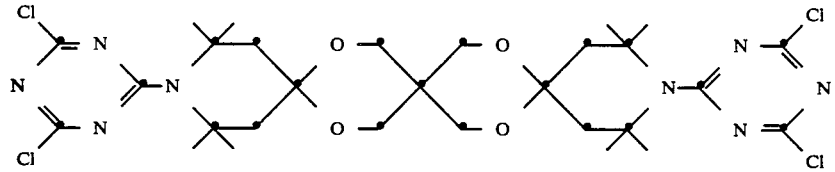

66 g of cyanuric chloride, dissolved in 500 ml of xylene, are added at 0° to 150 g of 2,2,4,4,14,14,16,16-octamethyl-7,11,18,21-tetraoxa-3,15-diazatrispiro[5,2,2,5,2,2-]heneicosane, suspended in 300 ml of xylene. After stirring under reflux for 51 hours, the mixture was allowed to cool somewhat, filtered and the liquid phase evaporated. After dissolving in acetone/chloroform/methylene chloride, chromatographic purification on an SiO$_2$ column and recrystallization from toluene, the compound of the above structure, which melts at 277°–278°, is obtained.

Analysis: Calc.: C: 49.30%; H: 5.71%; N: 15.86%; Found: C: 49.16%; H: 5.68%; N: 15.70%.

EXAMPLE 43

Compound of the formula

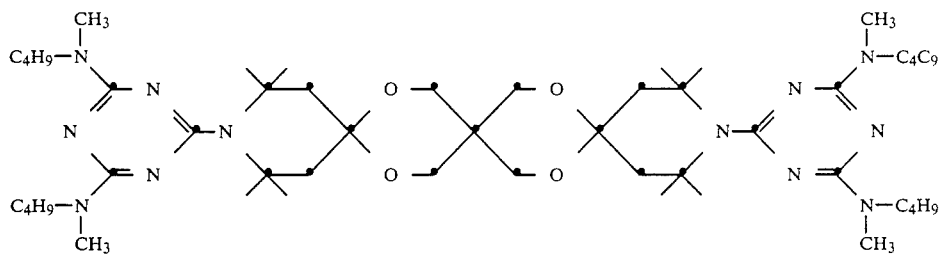

A mole equivalent amount of the tetrachloro compound described in Example 42 is used in place of the 2,4-dichloro-6-(4,4-ethylenedioxy-2,2,6,6tetramethylpiperidin- 1-yl)-1,3,5-triazine employed in Example 31 and the procedure is otherwise the same as given in Example 31. The compound of the above structure which melts at 141°–143°, is obtained after recrystallization from acetone.

Analysis: Calc.: C: 64.72%; H: 9.75%; N: 18.48%; Found: C: 64.66%; H: 9.79%; N: 18.37%.

EXAMPLE 44

2-Chloro-4-morpholino-6-(4,4-ethylenedioxy-2,2,6,6-tetramethylpiperidin-1-yl)-1,3,5-triazine.

3.8 g of morpholine and, 15 minutes later, a solution of 1.7 g of NaOH in 5 ml of water are added to a solution of 30 g of 2,4-dichloro-6-(4,4-ethylenedioxy-2,2,6,6-tetramethylpiperidin-1-yl)-1,3,5-triazine (product from Example 17) in 100 ml of toluene. The mixture is then warmed to 6020 and after 45 minutes a further 3.8 g of morpholine and 1.7 g of NaOH in 5 ml of water are added. After a further 1.5 hours, the reaction has ended. After cooling and adding 200 ml of toluene, the phases are separated. The organic phase is dried over Na2SO4 and evaporated. Recrystallizing from acetonitrile leads to the compound of the above structure which melts at 154°–156° (white powder).

Analysis: Calc.: C: 54.33%; H: 7.09%; N: 17.60%; Found: C: 54.58%; H: 7.18%; N: 17.70%.

EXAMPLE 45

2-[Bis-(2-hydroxyethyl)-amino]-4-morpholino-6-(4,4-ethylenedioxy-2,2,6,6-tetramethylpiperidin-1-yl)-1,3,5-triazine.

5.3 g of diethanolamine and a solution of 1 g of NaOH in 3 ml of water are added to a solution of 20 g of 2-chloro-4-morpholino-6-(4,4-ethylenedioxy-2,2,6,6-tetramethylpiperidin-1-yl)-1,3,5-triazine (product from Example 44) in 50 ml of xylene. 1 g of NaOH in 3 ml of water is again added after 1.75 hours with stirring under reflux. After 14 hours, 7.9 g of diethanolamine are added, after which the mixture is stirred under reflux for a further 28 hours. It is then allowed to cool and washed with water, and the organic phase is separated off. After drying over Na2SO4, evaporating and recrystallizing twice from toluene, the above product is obtained as a white powder which melts at 135°–140°.

Analysis: Calc.: C: 56.63%; H: 8.21%; N: 18.01%; Found: C: 56.67%; H: 8.13%; N: 17.90%.

EXAMPLE 46

Polycondensate from 2-[bis-(2-hydroxyethyl)-amino]-4-morpholino-6-(4,4-ethylenedioxy-2,2,6,6-tetramethylpiperidin-1-yl)-1,3,5-triazine and diethyl succinate. 3.5 ml of diethyl succinate and 0.4 g of tetrabutyl orthotitanate (monomer) are added to a solution of 9.8 g of 2-[bis-(2-hydroxyethyl)-amino]-4-morpholino-6-(4,4-ethylenedioxy-2,2,6,6-tetramethypiperidin-1-yl)-1,3,5-triazine (product from Example 45) in 50 ml of toluene. The mixture is heated for 24 hours so that toluene is removed very slowly by distillation. After cooling somewhat, the product is filtered through bleaching earth and evaporated. The residue is dried in vacuo at 80°. A resinous polymer of molecular weight $\overline{M}_n=966/\overline{M}_w=1409$ (gel permeation chromatography) is obtained.

EXAMPLE 47

2,4-Bis-morpholino-6-(4-butylamino-2,2,6,6-tetramethylpiperidin-1-yl)-1,3,5-triazine.

12 g of 2,4-bis-morpholino-6-(4-oxo-2,2,6,6-tetramethylpiperidin-1-yl)-1,3,5-triazine (product from Example 21) are hydrogenated in 120 ml of methanol and 60 ml of ethyl acetate at 40° and a pressure of 80 bar with 5% platinum on charcoal as the catalyst in the presence of 6 g of butylamine and 0.25 g of p-toluenesulfonic acid until the reaction has ended. The reaction mixture is filtered and evaporated. After dissolving the residue in methylene chloride and washing with water, the organic phase is dried over Na2SO4 and evaporated. The residue is dissolved in toluene/acetone and purified chromatographically on an SiO2 column. The oily product crystallizes after a few days and melts at 82°–87°.

Analysis: Calc.: C: 62.44%; H: 9.39%; N: 21.24%; Found: C: 62.88%; H: 9.39%; N: 20.45%.

EXAMPLE 48

Compound of the formula

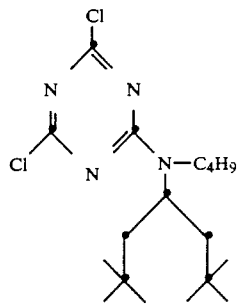

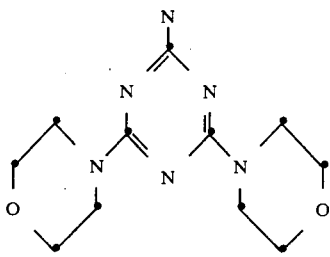

8 g of 2,4-bis-morpholino-6-(4-butylamino-2,2,6,6-tetramethylpiperidin-1-yl)-1,3,5-triazine (product from Example 47) in 30 ml of acetone are added dropwise with cooling to 0° to a solution of 3.2 g of cyanuric chloride in 40 ml of acetone. After adding 0.8 g of NaOH in 2 ml of water, the mixture is stirred at 0° for 3 hours, after which 60 ml of water are added. The product precipitated in this way is filtered off and recrystallized from acetonitrile. The white crystals of the above structure thus obtained melt at 198°–203°.

Analysis: Calc.: C: 53.20%; H: 6.94%; N: 22.98%; Found: C: 53.32%; H: 6.93%; N: 22.92%.

EXAMPLE 49

Compound of the formula

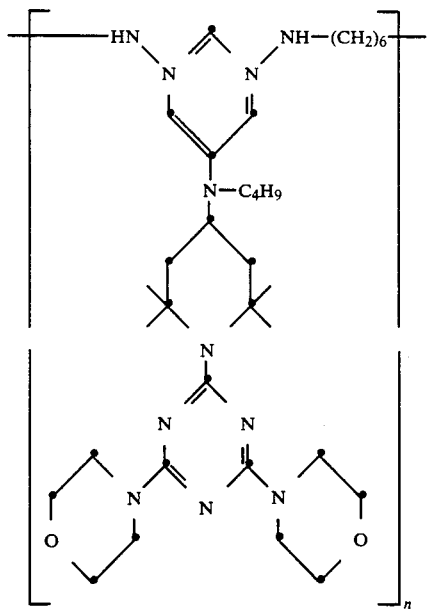

Polycondensate from compound from Example 48 and hexamethylenediamine. The dichloro compound described in Example 48 is used in mole equivalent amount in place of the 2,4-dichloro-6-(2,2,6,6-tetramethylpiperidin-1-yl)-1,3,5triazine described in Example 14 and the procedure is otherwise the same as described in Example 14. A pulverizable polymer of molecular weight $\overline{M}_n = 1520/\overline{M}_w = 1985$ is obtained (gel permeation chromatography).

EXAMPLE 50

2,4-Bis-morpholino-6-(4-methacryloyloxy-2,2,6,6-tetramethylpiperidin-1-yl)-1,3,5-triazine.

10.2 g of 2,4-dimorpholino-6-(4-hydroxy-2,2,6,6-tetramethylpiperidin-1-yl)-1,3,5-triazine (product from Example 34) are heated to 120° together with 6.9 ml of ethyl methacrylate, 0.04 g of 2,6-bis-tert-butyl-p-cresol and 0.04 ml of tetrabutylorthotitanate (monomer), some liquid slowly being removed by distillation. The mixture is allowed to react for 50 hours, some ethyl methacrylate and catalyst subsequently being added periodically. After the reaction has ended, the product is filtered through bleaching earth and evaporated. The residue is dissolved in toluene/acetone and purified chromatographically on an SiO$_2$ column, the above product being obtained as a colorless resin.

Analysis: Calc.: C: 60.74%; H: 8.07%; N: 17.71%; Found: C: 60.60%; H: 8.10%; N: 17.10%.

EXAMPLE 51

Homopolymer of 2,4-bis-morpholino-6-(4-methacryloyloxy-2,2,6,6-tetramethylpiperidin-1-yl)-1,3,5-triazine.

6 g of 2,4-bis-morpholino-6-(4-methacryloyloxy-2,2,6,6-tetramethylpiperidin-1-yl)-1,3,5-triazine (product from Example 50) are heated to 75° for 12 hours together with 0.13 g of dodecylmercaptan and 0.1 g of α,α'-azoisobutyronitrile in 25 ml of isopropyl methyl ketone under nitrogen. After evaporating the mixture and drying the residue for 72 hours at 60° in vacuo, a white, pulverizable polymer of molecular weight $\overline{M}_n = 3188/\overline{M}_w = 12064$ is obtained (gel permeation chromatography).

EXAMPLE 52

N,N'-bis[1-(2,4-dimorpholino-1,3,5-triazin-6-yl)-2,2,6,6-tetramethylpiperidin-4-yl]-hexamethylenediamine.

A mole equivalent amount of 1,6-diaminohexane is used in place of the butylamine employed in Example 47 and the procedure is otherwise the same as given in Example 47. The above compound is obtained as a white powder which melts at 198°–202°.

EXAMPLE 53

2-Chloro-4,6-bis-(2,2,6,6-tetramethylpiperidin-1-yl)-1,3,5-triazine.

18.4 g of cyanuric chloride and 113 g of 2,2,6,6-tetramethylpiperidine are heated for 10 hours at 180° and then for 10 hours at 210° in a 300 ml autoclave. The contents of the autoclave are then taken up in 500 ml of water, and the insoluble residue is filtered off by suction, washed with water and dried. The brownish residue is crystallized from ligroin. 2-Chloro-4,6-bis-(2,2,6,6-tetramethylpiperidin-1-yl)-1,3,5-triazine is obtained as colorless crystals having a melting point of 188°.

EXAMPLE 54

2,4-Dichloro-6-[2,2,6,6-tetramethyl-4-(N-acetylbutylamino)-piperidin-1-yl]-1,3,5-triazine.

9.2 g of cyanuric chloride and 26.7 g of 2,2,6,6-tetramethyl-4-(N-acetylbutylamino)-piperidine are reacted in 100 ml of xylene as described in Example 1 and worked up. 2,4-Dichloro-6-[2,2,6,6-tetramethyl-4-(N-acetylbutylamino)-piperidin-1-yl]-1,3,5-triazine is obtained as colorless crystals having a melting point of 131°–133°.

EXAMPLE 55

2-Chloro-4-isopropyloxy-6-(2,2,6,6-tetramethyl-piperidin-1-yl)-1,3,5-triazine.

104.0 g of 2,4-dichloro-6-isopropyloxy-1,3,5-triazine and 148.3 g of 2,2,6,6-tetramethylpiperidine are reacted in 300 ml of xylene as described in Example 1 and worked up. 2-Chloro-4-isopropyloxy-6-(2,2,6,6-tetramethylpiperidin-1-yl)-1,3,5-triazine is obtained by crystallization from hexane as colorless crystals having a melting point of 111°–112°.

EXAMPLE 56

2,4-Bis-isopropyloxy-6-(2,2,6,6-tetramethylpiperidin-1-yl)-1,3,5-triazine.

12.5 g of 2-chloro-4-isopropyloxy-6-(2,2,6,6-tetramethylpiperidin-1-yl)- 1,3,5-triazine (product from Example 55), 11.2 g of finely pulverized potassium hydroxide and 0.7 g of tetrabutylammonium hydrogen sulfate are initially introduced in 60 ml of toluene. 2.6 g of isopropanol are added dropwise during the course of 15 minutes to this orange-colored suspension: weakly exothermic reaction to about 30+. The pale brown contents of the flask are stirred at 60° for 8 hours, cooled to 0°–5°, and diluted with 80 ml of water and then with 40 ml of toluene. The brown, aqueous phase is separated off from the colorless, organic phase and the latter is washed four times, each with 80 ml of water, dried over sodium sulfate and completely evaporated in vacuo. A weakly yellowish oil is obtained which solidifies after a short time to give 2,4-bis-isopropyloxy-6-(2,2,6,6-tetramethylpiperidin-1-yl)-1,3,5-triazine with a melting range of 70°–98°.

EXAMPLE 57

2-Isopropyloxy-4-n-octoxy-6-(2,2,6,6-tetramethyl-piperidin-1-yl)-1,3,5-triazine.

5.7 g of 1-octanol are used in place of isopropanol and the procedure is as described in Example 56. 2-Isopropyloxy-4-n-octoxy-6-(2,2,6,6-tetramethylpiperidin-1-yl)-1,3,5-triazine is obtained as a weakly yellowish resin.

Analysis: Calc.: 13.7% N, found 13.87% N.

EXAMPLE 58

2-Isopropyloxy-4-dibutylamino-6-(2,2,6,6-tetramethylpiperidin-1-yl)-1,3,5-triazine.

12.5 g of 2-chloro-4-isopropyloxy-6-(2,2,6,6-tetramethylpiperidin-1-yl)-1,3,5-triazine and 5.5 g of dibutylamine are dissolved in 100 ml of xylene. After addition of a solution of 1.8 g of sodium hydroxide in 10 ml of water, the water is slowly removed by distillation in a water separator under a weak flow of nitrogen. The contents of the flask are subsequently stirred at 135° for about 16 hours. The mixture is allowed to cool somewhat, 50 ml of water are added to the contents of the flask and the mixture is stirred vigorously for 10 minutes. The aqueous phase is separated off and the organic layer is washed four times, each with 50 ml of water, dried over sodium sulfate and completely evaporated in vacuo. The 2-isopropyloxy-4-dibutylamino-6-(2,2,6,6-tetramethylpiperidin-1-yl)-1,3,5-triazine obtained is a weakly yellowish resin.

Analysis N: Calc. 17.27%, found 17.29%.

EXAMPLE 59

Compound of the formula

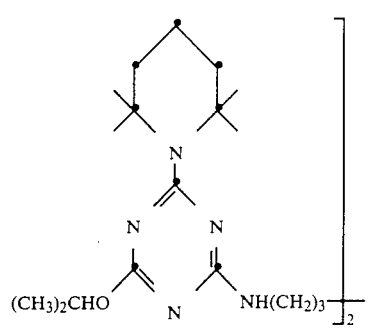

18.8 g of 2-chloro-4-isopropyloxy-6-(2,2,6,6-tetramethylpiperidin-1-yl)-1,3,5-triazine, 3.6 g of 1,6-diaminohexane and a solution of 2.6 g of sodium hydroxide in 10 ml of water are reacted in 100 ml of xylene as described in Example 58. The compound of the above formula is obtained as colorless crystals having a melting point of 224°–226° by crystallization from xylene.

EXAMPLE 60

2,4-Bis-(2-hydroxyethylamino)-6-(2,2,6,6-tetramethylpiperidin-1-yl)-1,3,5-triazine 26.9 g of ethanolamine (1st portion: 12.2 g; 2nd portion: 14.7 g) are used in place of dibutylamine and the procedure is otherwise as described in Example 6. 2,4-Bis-(2-hydroxyethylamino)-6-(2,2,6,6-tetramethyl-piperidin-1-yl)-1,3,5-triazine having a melting point of 147°–148° is obtained after crystallization from toluene.

EXAMPLE 61

Polymer of the formula

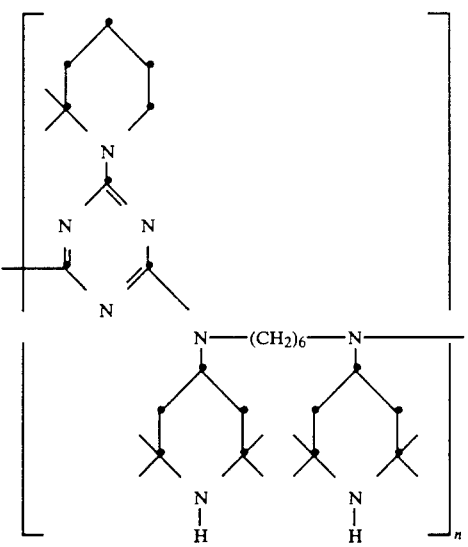

23.1 g of 2,4-dichloro-6-(2,2,6,6-tetramethylpiperidin-1-yl)-1,3,5-triazine and 31.4 g of 1,6-bis-(2,2,6,6-tetramethyl-4-piperidylamino)-hexane are reacted as described in Example 6 in the presence of 6.8 g of sodium hydroxide in 200 ml of xylene. The slightly yellowish resin obtained has a molecular weight of 1330.

EXAMPLE 62

Compound of the formula

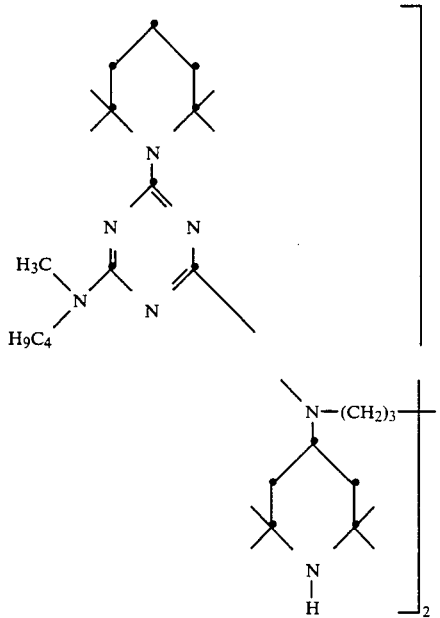

57.8 g of 2,4-dichloro-6-(2,2,6,6-tetramethylpiperidin-1-yl)-1,3,5-triazine are initially introduced in 200 ml of xylene. 127.4 g of N-methylbutylamine are added dropwise to this during the course of 15 minutes. The temperature climbs to 50°. A solution of 8.8 g of sodium hydroxide in 30 ml of water is then added dropwise to the reaction mixture during the course of 10 minutes and the mixture is stirred at 60° for 2 hours. The aqueous phase is then separated off, 41.4 g of 1,6-bis-(2,2,6,6-tetramethyl-4-piperidyl-amino)-hexane are added, the mixture is heated to 90° and a solution of 9.6 g of sodium hydroxide in 30 ml of water is then added. The water is then slowly removed by distillation in a water separator under a weak stream of nitrogen and the contents of the flask are then stirred at 135° for 18 hours. After allowing to cool somewhat, 100 ml of water are added to the reaction mixture and it is stirred vigorously for 10 minutes. The aqueous phase is separated off and the organic solution is washed three times, each with 50 ml of water, dried over sodium sulfate and evaporated in vacuo. The compound of the above formula is obtained as colorless crystals having a melting point of 137°–138° by crystallization of the residue from methyl ethyl ketone.

EXAMPLE 63

Compound of the formula

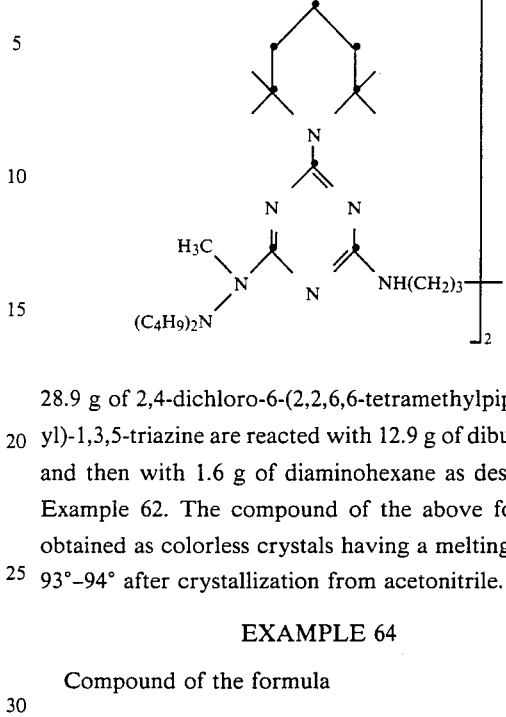

28.9 g of 2,4-dichloro-6-(2,2,6,6-tetramethylpiperidin-1-yl)-1,3,5-triazine are reacted with 12.9 g of dibutylamine and then with 1.6 g of diaminohexane as described in Example 62. The compound of the above formula is obtained as colorless crystals having a melting point of 93°–94° after crystallization from acetonitrile.

EXAMPLE 64

Compound of the formula

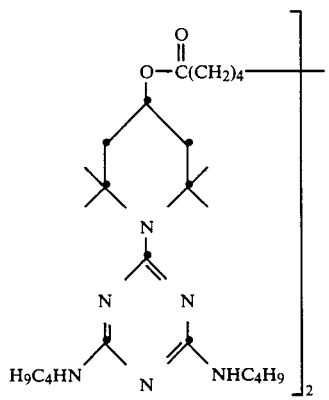

19.0 g of 2,4-bis-butylamino-6-(2,2,6,6-tetramethyl-4-hydroxypiperidin-1-yl)-1,3,5-triazine (prepared according to Example 9) are heated to reflux for 12 hours with 5.8 g of dimethyl sebacate in 150 ml of xylene after the addition of 0.2 g of lithium amide under a weak stream of nitrogen and removal of the methanol formed by distillation. The reaction mixture is allowed to cool to about 100°, 5 g of Tonsil Optimum (bleaching earth) is added, and the mixture is stirred for 5 minutes and filtered. By evaporating the solvent, the compound of the above formula is obtained as a slightly yellow resin.

Analysis: Calc. 18.20% N, found 18.51% N

EXAMPLE 65

Compound of the formula

EXAMPLE 67

2,4-Bis-butylamino-6-{2,2,6,6-tetramethyl-4-[2-(3,5-di-tert-butyl-4-hydroxyphenyl)-propionyloxy]-piperidin-1-yl}-1,3,5-triazine 14.6 g of methyl 2-(3,5-di-tert-butyl-4-hydroxyphenyl)-propionate is used in place of dimethylsebacate and the procedure is as described in Example 64. 2,4-Bis-butylamino-6-{2,2,6,6-tetramethyl-4-[2-(3,5-di-tert-butyl-4-hydroxyphenyl)-propionyloxy]-piperidin-1-yl}-1,3,5-triazine is obtained as a weakly yellowish resin. Analysis: calc. 13.15% N, found 13.36% N

EXAMPLE 68

Compound of the formula

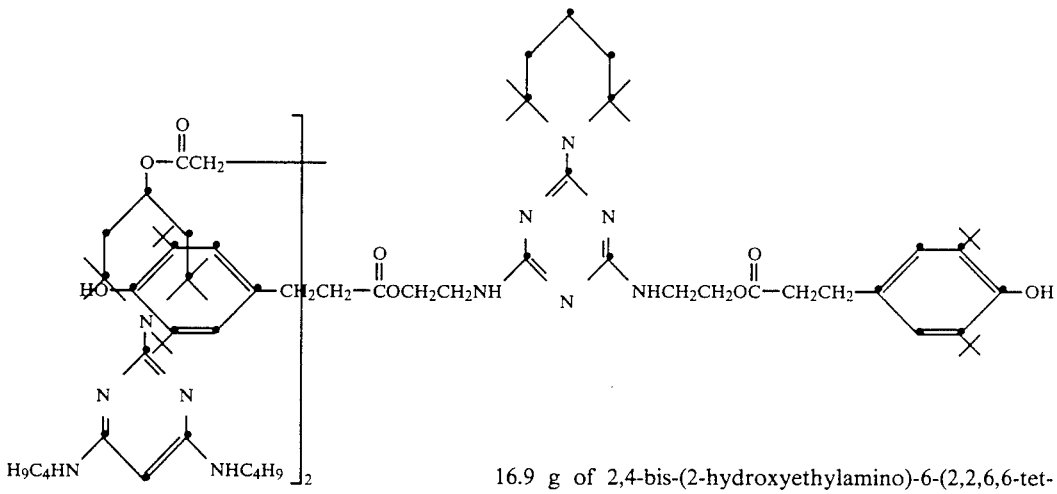

3.6 g of dimethyl succinate are used in place of dimethyl sebacate and the procedure is as described in Example 64. The compound of the above formula is obtained as colorless crystals having a melting point of 131° after crystallization from acetonitrile.

EXAMPLE 66

Compound of the formula 16.9 g of 2,4-bis-(2-hydroxyethylamino)-6-(2,2,6,6-tetramethylpiperidin-1-yl)-1,3,5-triazine (prepared according to Example 60) are heated to reflux for 12 hours with 29.2 g of methyl β-(3,5-di-tert-butyl-4-hydroxyphenyl)-propionate in 100 ml of xylene after the addition of 0.2 g of lithium amide under a weak stream of nitrogen and removal of the methanol formed by distillation. The reaction mixture is allowed to cool to about 100°, 5 g of Tonsil Optimum (bleaching earth) is added, and the mixture is stirred for 5 minutes and filtered.

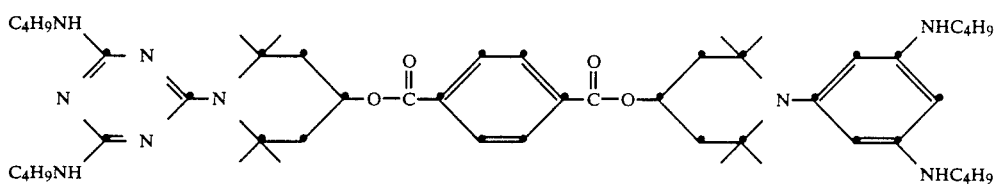

4.8 g of dimethyl terephthalate are used in place of dimethyl sebacate and the procedure is as described in Example 64. The compound of the above formula is obtained as colorless crystals having a melting point of 181° after crystallization from xylene.

After evaporating the solvent, the compound of the above formula is obtained as a yellowish resin.
Analysis: Calc. 9.78% N, found 0.67% N.

EXAMPLE 69

Compound f the formula

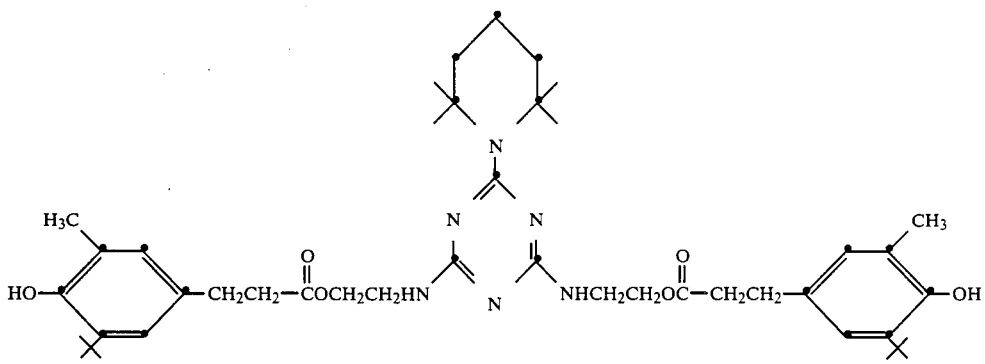

25.0 g of methyl β-(3-methyl-4-hydroxy-5-tert-butyl-phenyl)-propionate is used in place of methyl β-(3,5-di-tert-butyl-4-hydroxyphenyl)-propionate and the procedure is as described in Example 68. The compound of the above formula is obtained as a yellowish, pulverizable resin.

Analysis: Calc. 10.84% N, found 10.57% N.

EXAMPLE 70

2-Chloro-4-[N-(2,2,6,6-tetramethyl-4piperidyl)-n-butylamino]-6-(2,2,6,6-tetramethyl-4-hexyloxypiperidin-1yl)-1,3,5-triazine The dichloro derivative from Example 10 is reacted with an equivalent of 12.5 g of 2-chloro-4-isopropyloxy-6-(2,2,6,6-tetramethylpiperidin-1-yl)-4-butylamino-2,2,6,6-tetramethylpiperidine and the procedure in this case is as described in Example 26. The title compound is obtained as a colorless oil.

Analysis: Calc. 14.87% N, found 14.74% N.

EXAMPLE 71

N,N′,N″-Tris{2-(2,2,6,6-tetramethyl-4-hexyloxypiperidin-1-yl)-4-[N-(2,2,6,6-tetramethylpiperidin-4-yl)-butylamino]-1,3,5-triazin-6-yl}-diethylenetriamine 0.71 ml of diethylenetriamine and 0.9 g of NaOH, dissolved in 3 ml of water, are added to 10.6 g of the monochloro derivative from Example 70, dissolved in 50 ml of toluene. After warming to 100°, the solvent begins to distill off. A further 50 ml of toluene and 1 g of polyethylene glycol 1000 and 0.9 g of NaOH are added and the mixture is heated with stirring for 14 h under reflux. After cooling, the reaction mixture is diluted using 100 ml of ethyl acetate and the solution is washed four times with water. The organic solution is dried over Na$_2$SO$_4$ and evaporated. The residue is dissolved in 50 ml of methanol, filtered through 200 g of silica gel and washed with 500 ml of methanol. The methanol solution is evaporated, the residue being a nearly colorless resin.

Analysis: Calc. 17.4% N, found 17.4% N.

EXAMPLE 72

Stabilization of a two-coat varnish

A clear varnish is prepared by mixing the following components:

58.3 parts of an acrylate resin VIACRYL ®VC 373, Vianova AG)
27.3 parts of a melamine resin (MAPRENAL ®MF 590 Hoechst AG)
4.0 parts of an aromatic solvent mixture (SOLVESSO ®150)
5.4 parts of xylene
4.0 parts of butyl glycol acetate
1.0 parts of a flow control auxiliary (BAYSILON ®A, Bayer AG)

The light stabilizers shown in Table 1 are added to this varnish. The varnish is diluted until sprayable using a 1:1:1 mixture of butyl acetate and xylene and sprayed onto an aluminum sheet painted with a metallic silver base coat. The samples are then hardened at 130° C. for 30 minutes. A coat thickness of the clear varnish of 40-45 μm results.

The samples prepared in this way are weathered in an UVCON ® exposure apparatus (Atlas Corp.) with a cycle of 8 h UV irradiation at 70° C. and 4 h condensation at 50° C.

After 400 h weathering in each case, the 20° gloss of the samples is measured according to DIN 67530. The results are shown in Table 1.

TABLE 1

| Light stabilizer[1] | 20° gloss after | | | |
|---|---|---|---|---|
| | 0 | 400 | 800 | 1200 h |
| none | 85 | 83 | 19[2] | |
| 1% of Example 5 | 86 | 84 | 67 | 28[2] |
| 1% of Example 6 | 87 | 85 | 75 | 43 |
| 1% of Example 7 | 88 | 86 | 74 | 40 |
| 1% of Example 13 | 86 | 85 | 78 | 31 |
| 1% of Example 24 | 87 | 86 | 80 | 35 |

[1]Amount data relative to the solids content of the varnish
[2]Formation of cracks

EXAMPLE 73

Open air weathering of a two-coat layer

A two-coat varnishing is prepared as described in Example 70. The samples are exposed to open air weathering in Florida for 54 months. The 20° gloss is measured every 12 months according to DIN 67530. The results are shown in Table 2.

TABLE 2

| Light stabilizer[1] | 20° gloss after | | | | | |
|---|---|---|---|---|---|---|
| months | 0 | 12 | 24 | 36 | 48 | 54 |
| none | 93 | 70 | 49 | 36[2] | 16 | — |
| 1% of Example 4 | 94 | 73 | 76 | 69 | 57 | 53[2] |
| 1% of Example 5 | 95 | 72 | 73 | 69 | 64 | 67 |

[1]Amount data relative to the solids content of the varnish
[2]Formation of cracks

EXAMPLE 74

0.087 g of the yellow coupler of the formula

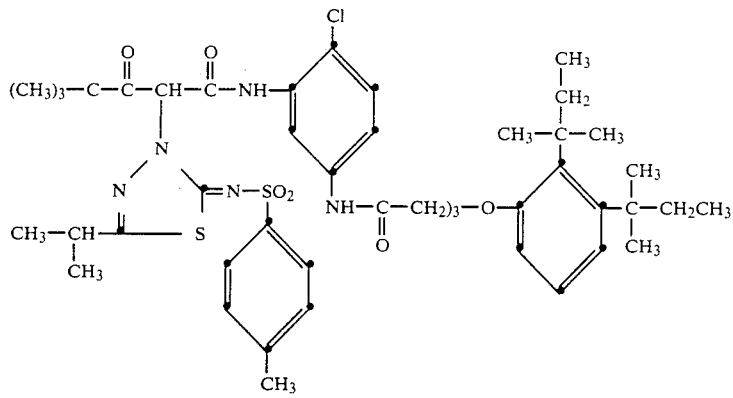

are dissolved in 2.0 ml of a solution of the stabilizer shown in Table 3 in ethyl acetate (2.25 g/100 ml). 9.0 ml of a 2.3% aqueous gelatin solution which is adjusted to a pH of 6.5 and contains 1.744 g/l of the wetting agent of the formula

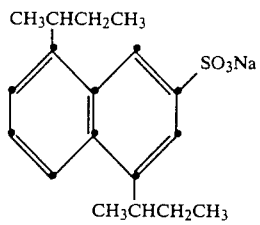

is added to 1.0 ml of this solution.

2 ml of a silver bromide emulsion having a silver content of 6.0 g/l and 1.0 ml of a 0.7% aqueous solution of the hardener of the formula

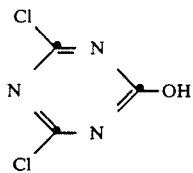

is added to 5.0 ml of the coupler emulsion thus obtained and it is poured onto a 13×18 cm plastic-coated paper. After a hardening time of 7 days, the samples are exposed to 125 Lux.s behind a silver step wedge and subsequently processed in the Kodak EKTAPRINT 2 ® process.

The yellow wedges obtained are irradiated with a total of 60 k Joule/cm$^2$ in an Atlas Weather-Ometer using a 2500W xenon lamp behind a UV filter (Kodak 2C).

A sample without stabilizer is treated at the same time as a standard.

Table 3 which follows gives the color density loss occurring during the irradiation at the absorption maximum of the yellow dye, measured using a Macbeth TR 924A densitometer.

The light stabilizer effect is evident from the color density loss. The smaller the density loss, the higher the light stabilizer effectiveness.

TABLE 3

| Stabilizer | Colour density loss (in %) |
|---|---|
| none | 35 |
| Product from Example 68 | 18 |
| Product from Example 69 | 14 |

EXAMPLE 75

0.033 g each of the cyan coupler of the formula

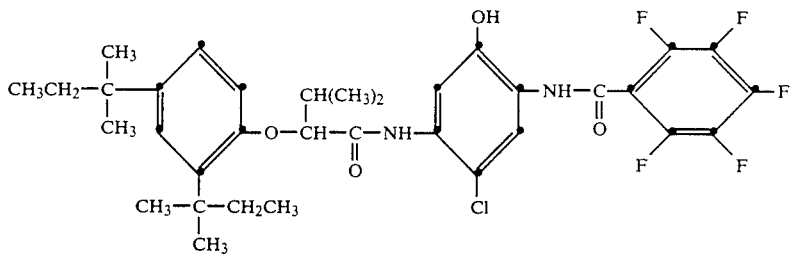

and of the stabilizer given in Table 4 are dissolved in 2.0 ml of a mixture of dibutyl phthalate/ethyl acetate (0.8 g/100 ml).

9.0 ml of a 2.3% aqueous gelatin solution which is adjusted to a pH of 6.5 and contains 0.872 g/l of the wetting agent sodium dibutylnaphthalenesulfonate is added to 1.0 ml of this solution.

Then, the procedure using the emulsion is used as described in Example 72, but with the difference that the silver bromide emulsion has a silver content of 3 g/l.

The color step wedges obtained are irradiated with a total of 60 k Joule/cm$^2$ in an Atlas Weather-Ometer using a 2500 W xenon lamp behind a UV filter (Kodak 2c), and the color density loss is subsequently determined, as described in Example 72.

The results are summarized in the following Table 4.

TABLE 4

| Stabilizer | Colour density loss (in %) |
| --- | --- |
| none | 43 |
| Product from Example 68 | 22 |
| Product from Example 69 | 23 |

What is claimed is:

1. A 2,2,6,6-tetramethyl-1-piperidyl-triazinyl compound of the formula II

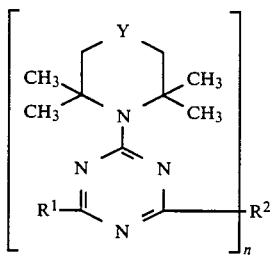

in which n is an integer from 1 to 6, $R^1$ is a radical of the formula

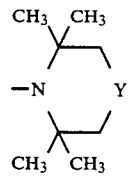

or Cl, OH, $-OR^3$, $-SR^3$ or $-NR^4R^5$, where $R^3$ is $C_1-C_{18}$alkyl, allyl, cyclohexyl, benzyl, phenyl or a group of the formula A

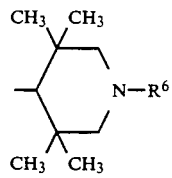

$R^4$ is hydrogen, $C_1-C_{12}$alkyl, 2-hydroxyethyl, allyl, cyclohexyl, benzyl or a group of the formula A, $R^5$ is $C_1-C_{12}$alkyl, 2-hydroxyethyl, allyl, cyclohexyl, benzyl, phenyl, phenyl which is substituted by halogen, $C_1-C_4$alkyl or $C_1-C_4$alkoxy, a group of the formula A or a group of the formula C

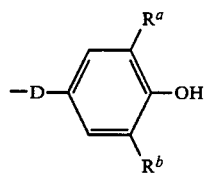

in which D is $C_2-C_{20}$alkylene interrupted by

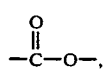

$R^a$ and $R^b$ are $C_1-C_{12}$alkyl, $C_5-C_6$cycloalkyl, $C_6-C_{10}$aryl or $C_7-C_9$phenylalkyl and $R^a$ is also hydrogen, or $R^4$ and $R^5$ together are $C_4-C_8$alkylene which may optionally be interrupted by $-O-$ or $-N(R^8)-$ and in which $R^8$ is hydrogen, $C_1-C_4$ alkyl or acetyl, $R^6$ is hydrogen, $C_1-C_{12}$ alkyl, $C_7-C_9$phenylalkyl, $C_3-C_5$alkenyl, $C_2-C_4$alkanoyl, $C_3-C_5$alkenoyl, $-O$, $-OH$ or $-OR^7$ and $R^7$ is $C_1-C_{18}$alkyl, $C_5-C_8$cycloalkyl, $C_7-C_9$phenylalkyl, phenyl, $C_2-C_{18}$alkanoyl or benzoyl, $R^2$, if n=1, is Cl, OH, $-OR^3$, $-SR^3$ or $-NR^4R^5$, if n=2, $R^2$ is a group $-O-R^9-O-$, $-S-R^9-S-$, $-N(R^{10})-R^9-N(R^{10})-$, $-O-R^9-N(R^{10})-$,

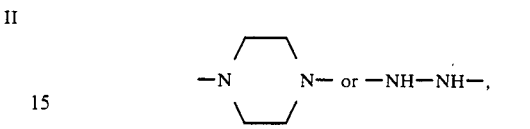

where $R^9$ is $C_2-C_{20}$alkylene which may optionally be interrupted by one or more $-O-$, $-N(R^8)-$ or $-OOC-R^{17}-COO-$, $C_4-C_8$alkenylene, $C_5-C_8$cycloalkylene, xylylene, phenylene or tolylene, $R^{10}$ is hydrogen, $C_1-C_{12}$alkyl, allyl, 2-hydroxyethyl, benzyl, phenyl or a group of the formula A, if n=3, $R^2$ is a group

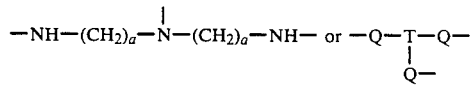

in which a is 2 or 3, Q is $-O-$, $-S-$ or $-N(R^{10})-$ and T is $C_3-C_{20}$alkanetriyl or a group

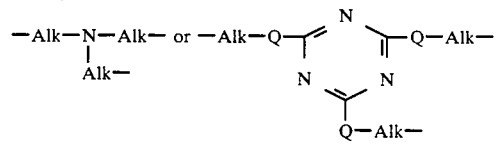

in which Alk is a $C_2-C_{12}$alkylene group, if n=4, $R^2$ is a group $C(CH_2O-)_4$ or

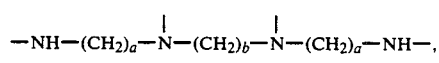

in which a is 2 or 3 and b is 2-12, if n=5, $R^2$ is a group

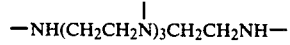

and if n=6, $R^2$ is a group

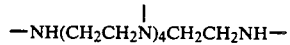

Y is a group

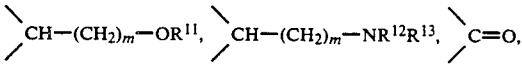

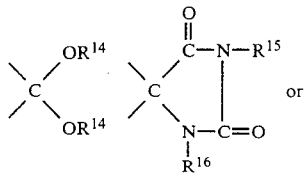 or

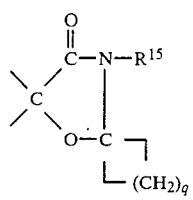

in which m is 0, 1 or 2, q is an integer from 5–11, $R^{11}$ is hydrogen, $C_1$–$C_{18}$alkyl, $C_3$–$C_7$alkenyl, $C_5$–$C_8$cycloalkyl, $C_7$–$C_{11}$aralkyl or a group —CO—$R^{18}$, $R^{12}$ is hydrogen, $C_1$–$C_{12}$alkyl, $C_3$–$C_7$alkenyl, $C_5$–$C_8$cycloalkyl, $C_7$–$C_{11}$aralkyl, $C_2$–$C_4$hydroxyalkyl, $C_3$–$C_8$alkoxyalkyl, $C_4$–$C_{20}$dialkylaminoalkyl, $C_3$–$C_{14}$alkoxycarbonylalkyl or a group of the formula A, $R^{13}$ is $C_1$–$C_{12}$alkyl, $C_2$–$C_4$hydroxyalkyl, $C_3$–$C_7$alkenyl, $C_5$–$C_8$cycloalkyl, phenyl, phenyl which is substituted by halogen, $C_1$–$C_4$alkyl or $C_1$–$C_4$alkoxy, $C_2$–$C_{20}$alkanoyl, $C_3$–$C_8$alkenoyl, benzoyl, phenylacetyl or a triazinyl radical of the formula B

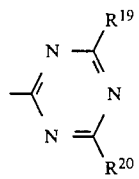

or $R^{12}$ and $R^{13}$ together are $C_4$–$C_8$alkylene which may optionally be interrupted by —O— or —N($R^8$)— or $R^{12}$ and $R^{13}$ together are a radical of the formula

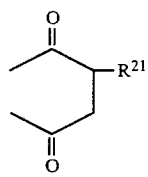

in which $R^{21}$ is $C_1$–$C_{18}$alkyl, $R^{14}$ is $C_1$–$C_{18}$alkyl, $C_5$–$C_8$cycloalkyl or $C_7$–$C_9$phenylalkyl or both groups $R^{14}$ together are $C_2$–$C_6$alkylene, o-phenylene or o-xylylene, $R^{15}$ is hydrogen, $C_1$–$C_{12}$alkyl, $C_3$–$C_5$alkenyl, $C_7$–$C_9$phenylalkyl, $C_2$–$C_4$hydroxyalkyl, $C_3$–$C_8$alkoxyalkyl or $C_3$–$C_{14}$alkoxycarbonylalkyl, $R^{16}$ is hydrogen, $C_1$–$C_{12}$alkyl, allyl or benzyl, $R^{17}$ is $C_1$–$C_{12}$alkylene, vinylene, cyclohexylene, xylylene or $C_6$–$C_{12}$arylene, $R^{18}$ is $C_1$–$C_{18}$alkyl, $C_2$–$C_6$alkenyl, $C_5$–$C_8$cycloalkyl, $C_7$–$C_9$phenylalkyl, phenyl or phenyl which is substituted by halogen, nitro, $C_1$–$C_4$alkyl, hydroxyl or $C_1$–$C_4$alkoxy or $C_7$–$C_9$phenylalkyl which is substituted by hydroxyl and $C_1$–$C_4$alkyl, $R^{19}$ is as defined for $R^1$, and $R^{20}$ is Cl, —OH, —$OR^3$, —$SR^3$ or —$NR^4R^5$.

2. A 2,2,6,6-tetramethyl-1-piperidyl-triazinyl compound of the formula III

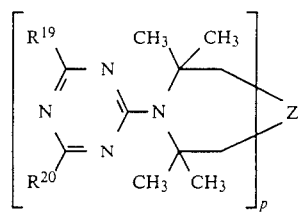

in which p is 2, 3 or 4, $R^{19}$ is a radical of the formula

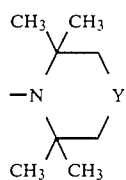

or Cl, OH, —$OR^3$, —$SR^3$ or —$NR^4R^5$, where $R^3$ is $C_1$–$C_{18}$alkyl, allyl, cyclohexyl, benzyl, phenyl or a group of the formula A

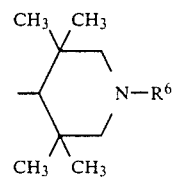

$R^4$ is hydrogen, $C_1$–$C_{12}$alkyl, 2-hydroxyethyl, allyl, cyclohexyl, benzyl or a group of the formula A, $R^5$ is $C_1$–$C_{12}$alkyl, 2-hydroxyethyl, allyl, cyclohexyl, benzyl, phenyl, phenyl which is substituted by halogen, $C_1$–$C_4$alkyl or $C_1$–$C_4$alkoxy, a group of the formula A or a group of the formula C

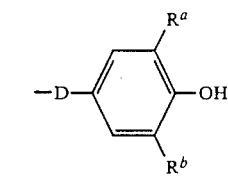

in which D is $c_2$–$C_{20}$alkylene interrupted by

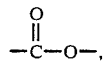

$R^a$ and $R^b$ are $C_1$–$C_{12}$alkyl, $C_5$–$C_6$cycloalkyl, $C_6$–$C_{10}$aryl or $C_7$–$C_9$phenylalkyl and $R^a$ is also hydrogen, or $R^4$ and $R^5$ together are $C_4$–$C_8$alkylene which may optionally be interrupted by —O— or —N($R^8$)— and in which $R^8$ is hydrogen, $C_1$–$C_4$alkyl or acetyl, $R^6$ is hydrogen, $C_1$–$C_{12}$alkyl, $C_7$–$C_9$phenylalkyl, $C_3$–$C_5$alkenyl, $C_2$–$C_4$alkanoyl, $C_3$–$C_5$alkenoyl, —O, —OH or —$OR^7$ and $R^7$ is $C_1$–$C_{18}$alkyl, $C_5$–$C_8$cycloalkyl, $C_7$–$C_9$phenylalkyl, phenyl, $C_2$–$C_{18}$alkanoyl or benzoyl, $R^{20}$ is Cl, —OH, —$OR^3$, $SR^3$ or $NR^4R^5$, and Z, if p=2, is one of the groups

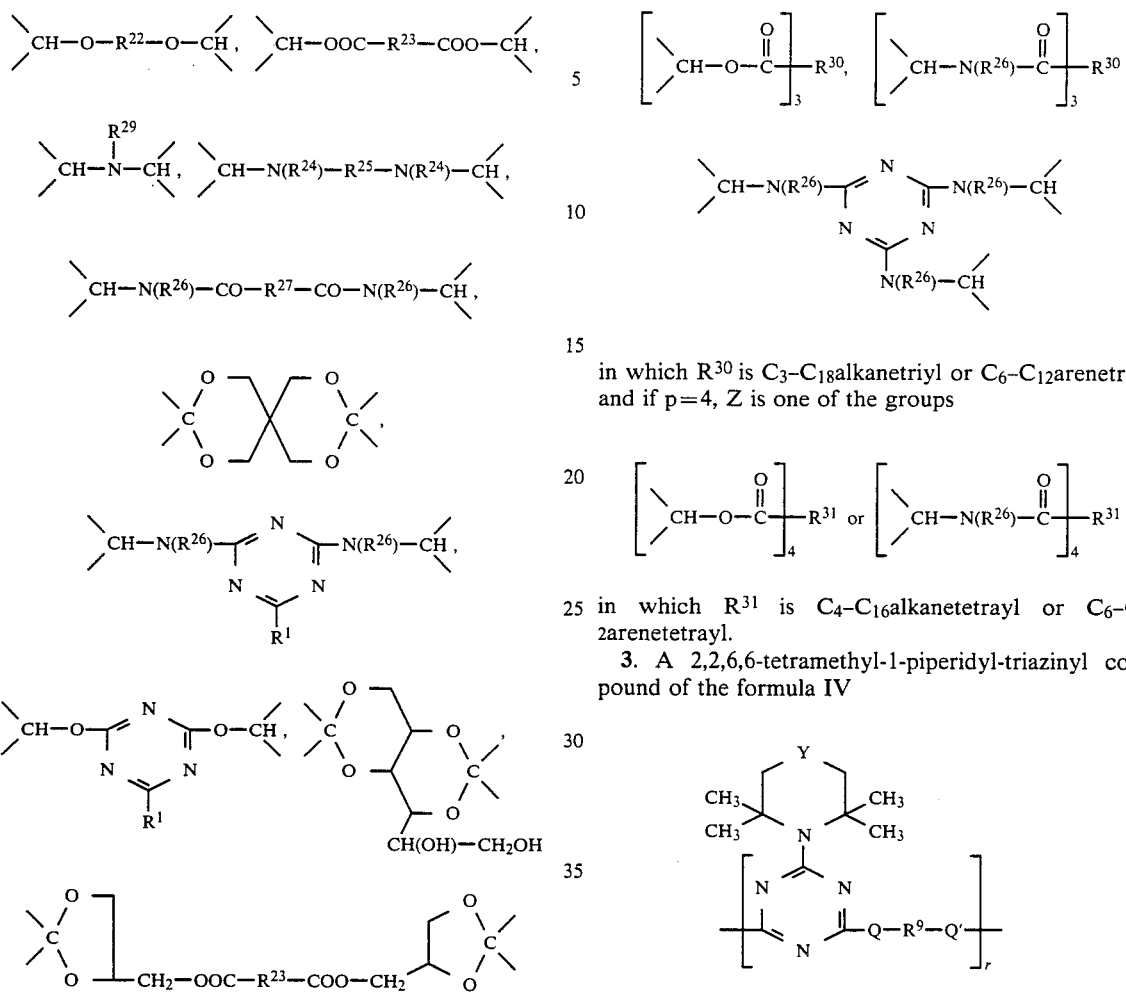

in which $R^{22}$ is $C_2$-$C_{12}$alkylene, $C_4$-$C_8$alkenylene, xylylene or —CO—, $R^{23}$ is $C_1$-$C_{12}$alkylene, vinylene, cyclohexylene, xylylene, $C_6$-$C_{12}$arylene or phenylene which is substituted by halogen, nitro or $C_1$-$C_4$alkyl, or a direct bond, $R^{24}$ is hydrogen, $C_1$-$C_{12}$alkyl, $C_5$-$C_8$cycloalkyl, $C_7$-$C_9$phenylalkyl, $C_3$-$C_7$alkenyl, $C_2$-$C_{18}$alkanoyl, $C_3$-$C_7$alkenoyl, or benzoyl, $R^{25}$ is $C_2$-$C_{12}$alkylene, $C_4$-$C_{16}$alkylene which is interrupted by NH or O, $C_4$-$C_8$alkenylene, xylylene or cyclohexylene, $R^{26}$ is hydrogen, $C_1$-$C_{12}$alkyl, $C_5$-$C_8$cycloalkyl or a group of the formula A, $R^{27}$ is as defined for $R^{23}$ or is a group —NH—$R^{28}$—NH—, $R^{28}$ is $C_2$-$C_{12}$alkylene or $C_6$-$C_{12}$arylene which may optionally be substituted by $C_1$-$C_4$alkyl, $R^{29}$ is hydrogen, $C_1$-$C_{12}$alkyl, $C_2$-$C_{18}$alkanoyl or a triazinyl radical of the formula B

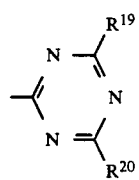

and $R^1$ is as defined for $R^{19}$, $R^{20}$ is Cl, —OH, —$OR^3$, —$SR^3$ or —$NR^4R^5$, and if p=3, Z is one of the groups

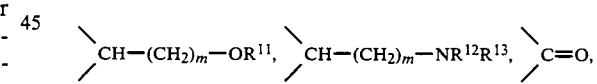

in which $R^{30}$ is $C_3$-$C_{18}$alkanetriyl or $C_6$-$C_{12}$arenetriyl, and if p=4, Z is one of the groups

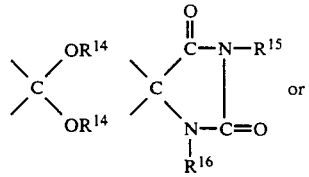

in which $R^{31}$ is $C_4$-$C_{16}$alkanetetrayl or $C_6$-$C_{12}$arenetetrayl.

3. A 2,2,6,6-tetramethyl-1-piperidyl-triazinyl compound of the formula IV

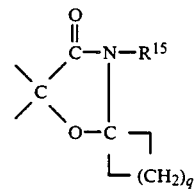

in which r has a value from 3 to 50, Q and Q' independently of one another are —O—, —S— or —N($R^{10}$)—, Y is a group in which m is 0, 1 or 2, q is an integer from 5-11, $R^{11}$ is hydrogen, $C_1$-$C_{18}$alkyl, $C_3$-$C_7$alkenyl, $C_5$-$C_8$cycloalkyl, $C_7$-$C_{11}$aralkyl or a group —CO—$R^{18}$, $R^{12}$ is hydrogen, $C_1$-$C_{12}$alkyl, $C_3$-$C_7$alkenyl, $C_5$-$C_8$cycloalkyl, C$_7$-C$_{11}$aralkyl, C$_2$-C$_4$hydroxyalkyl, C$_3$-C$_8$alkoxyalkyl, C$_4$-C$_{20}$dialkylaminoalkyl, C$_3$-C$_{14}$alkoxycarbonylalkyl or a group of the formula A

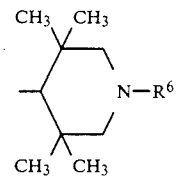

R$^6$ is hydrogen, C$_1$-C$_{12}$alkyl, C$_7$-C$_9$phenylalkyl, C$_3$-C$_5$alkenyl, C$_2$-C$_4$alkanoyl, C$_3$-C$_5$alkenoyl, —O, —OH or —OR$^7$, R$^7$ is C$_1$-C$_{18}$alkyl, C$_5$-C$_8$cycloalkyl, C$_7$-C$_9$phenylalkyl, phenyl, phenyl which is substituted by halogen, C$_1$-C$_4$alkyl or C$_1$-C$_4$alkoxy, C$_2$-C$_{20}$alkanoyl, C$_3$-C$_8$alkenoyl, benzoyl, phenylacetyl or a triazinyl radical of the formula B

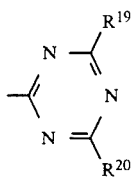

or R$^{12}$ and R$^{13}$ together are C$_4$-C$_8$alkylene which may optionally be interrupted by —O— or —N(R$^8$)— wherein R$^8$ is hydrogen, C$_1$-C$_4$alkyl or acetyl, or R$^{12}$ and R$^{13}$ together are a radical of the formula

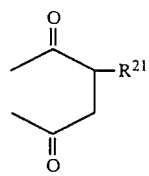

R$^{19}$ is a radical of the formula

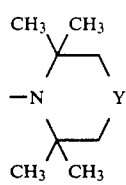

or Cl, OH, —OR$^3$, —SR$^3$ or —NR$^4$R$^5$, where R$^3$ is C$_1$-C$_{18}$alkyl, allyl, cyclohexyl, benzyl, phenyl or a group of the formula A, R$^4$ is hydrogen, C$_1$-C$_{12}$alkyl, 2-hydroxyethyl, allyl, cyclohexyl, benzyl or a group of the formula A, R$^5$ is C$_1$-C$_{12}$alkyl, 2-hydroxyethyl, ally, cyclohexyl, benzyl, phenyl, phenyl which is substituted by halogen, C$_1$-C$_4$alkyl or C$_1$-C$_4$alkoxy, a group of the formula A or a group of the formula C

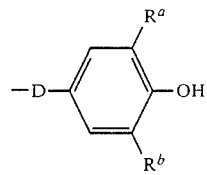

in which D is C$_2$-C$_{20}$alkylene interrupted by

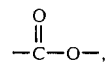

R$^a$ and R$^b$ are C$_1$-C$_{12}$alkyl, C$_5$-C$_6$cycloalkyl, C$_6$-C$_{10}$aryl or C$_7$-C$_9$phenylalkyl and R$^a$ is also hydrogen, or R$^4$ and R$^5$ together are C$_4$-C$_8$alkylene which may optionally be interrupted by —O— or —N(R$^8$)—, C$_1$-C$_4$alkyl or acetyl, R$^{20}$ is Cl, —OH, —OR$^3$, —SR$^3$ or NR$^4$R$^5$, R$^{21}$ is C$_1$-C$_{18}$alkyl, R$^{14}$ is C$_1$-C$_{18}$alkyl, C$_5$-C$_8$cycloalkyl or C$_7$-C$_9$phenylalkyl or both groups R$^{14}$ together are C$_2$-C$_5$alkylene, o-phenylene or o-xylylene, R$^{15}$ is hydrogen, C$_1$-C$_{12}$alkyl, C$_3$-C$_5$alkenyl, C$_7$-C$_9$phenylalkyl, C$_2$-C$_4$hydroxyalkyl, C$_3$-C$_8$alkoxyalkyl or C$_3$-C$_{14}$alkoxycarbonylalkyl, R$^{16}$ is hydrogen, C$_1$-C$_{12}$alkyl, allyl or benzyl, R$^{17}$ is C$_1$-C$_{12}$alkylene, vinylene, cyclohexylene, xylylene or C$_5$-C$_{12}$arylene, R$^{18}$ is C$_1$-C$_{18}$alkyl, C$_2$-C$_6$alkenyl, C$_5$-C$_8$cycloalkyl, C$_7$-C$_9$phenylalkyl, phenyl or phenyl which is substituted by halogen, nitro, C$_1$-C$_4$alkyl, hydroxyl or C$_1$-C$_4$alkoxy or C$_7$-C$_9$phenylalkyl which is substituted by hydroxyl and C$_1$-C$_4$alkyl, R$^9$ is C$_2$-C$_{20}$alkylene which may be optionally interrupted by one or more —O—, —N(R$^8$)— or —OOC—R$^{17}$—COO—, C$_4$-C$_8$alkenylene, C$_5$-C$_8$cycloalkylene, xylylene, phenylene or tolylene, R$^{10}$ is hydrogen, C$_1$-C$_{12}$alkyl, allyl, 2-hydroxyethyl, benzyl, phenyl or a group of the formula A or in which —Q—R$^9$—Q'— is a group —NHNH—,

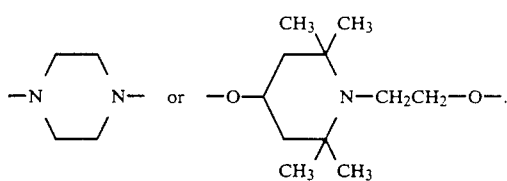

4. A 2,2,6,6-tetramethyl-1-piperidyl-triazinyl compound of the formula V

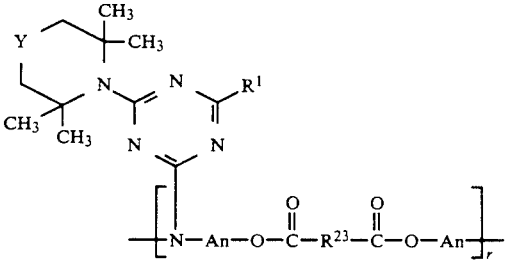

in which r has a value from 3 to 50, R$^1$ is a radical of the formula

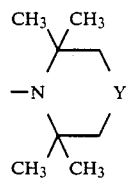

or Cl, OH, —OR$^3$, —SR$^3$ or —NR$^4$R$^5$, where R$^3$ is C$_1$-C$_{18}$alkyl, allyl, cyclohexyl, benzyl, phenyl or a group of the formula A

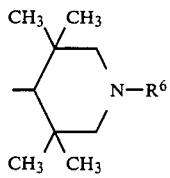

R$^4$ is hydrogen, C$_1$-C$_{12}$alkyl, 2-hydroxyethyl, allyl, cyclohexyl, benzyl or a group of the formula A, R$^5$ is C$_1$-C$_{12}$alkyl, 2-hydroxyethyl, allyl, cyclohexyl, benzyl, phenyl, phenyl which is substituted by halogen, C$_1$-C$_4$alkyl or C$_1$-C$_4$alkoxy, a group of the formula A or a group of the formula C

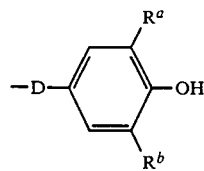

in which D is C$_2$-C$_{20}$alkylene interrupted by

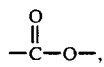

R$^a$ and R$^b$ are C$_1$-C$_{12}$alkyl, C$_5$-C$_6$cycloalkyl, C$_6$-C$_{10}$aryl or C$_7$-C$_9$phenylalkyl and R$^a$ is also hydrogen, or R$^4$ and R$^5$ together are C$_4$-C$_8$alkylene which may optionally be interrupted by —O— or —N(R$^8$)— and in which R$^8$ is hydrogen, C$_1$-C$_4$alkyl or acetyl, R$^6$ is hydrogen, C$_1$-C$_{12}$alkyl, C$_7$-C$_9$phenylalkyl, C$_3$-C$_5$alkenyl, C$_2$-C$_4$alkanoyl, C$_3$-C$_5$alkenoyl, —O, —OH or —OR$^7$ and R$^7$ is C$_1$-C$_{18}$alkyl, C$_5$-C$_8$cycloalkyl, C$_7$-C$_9$phenylalkyl, phenyl, C$_2$-C$_{18}$alkanoyl or benzoyl, Y is a group

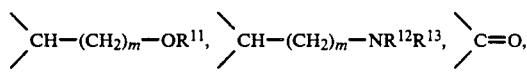

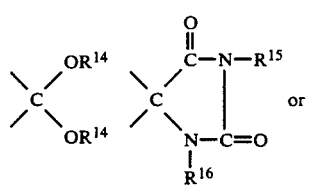

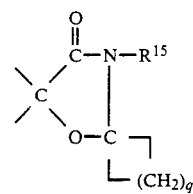

in which m is 0, 1 or 2, q is an integer from 5-11, R$^{11}$ is hydrogen, C$_1$-C$_{18}$alkyl, C$_3$-C$_7$alkenyl, C$_5$-C$_8$cycloalkyl, C$_7$-C$_{11}$aralkyl or a group —CO—R$^{18}$, R$^{12}$ is hydrogen, C$_1$-C$_{12}$alkyl, C$_3$-C$_7$alkenyl, C$_5$-C$_8$cycloalkyl, C$_7$-C$_1$aralkyl, C$_2$-C$_4$hydroxyalkyl, C$_3$-C$_8$alkoxyalkyl, C$_4$-C$_{20}$dialkylaminoalkyl, C$_3$-C$_{14}$alkoxycarbonylalkyl or a group of the formula A, R$^{13}$ is C$_1$-C$_{12}$alkyl, C$_2$-C$_4$hydroxyalkyl, C$_3$-C$_7$alkenyl, C$_5$-C$_8$cycloalkyl, phenyl, phenyl which is substituted by halogen, C$_1$-C$_4$alkyl or C$_1$-C$_4$alkoxy, C$_2$-C$_{20}$alkanoyl, C$_3$-C$_8$alkenoyl, benzoyl, phenylacetyl or a triazinyl radical of the formula B

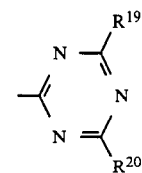

or R$^{12}$ and R$^{13}$ together are C$_4$-C$_8$alkylene which may optionally be interrupted by —O— or —N(R$^8$)— or R$^{12}$ and R$^{13}$ together are a radical of the formula

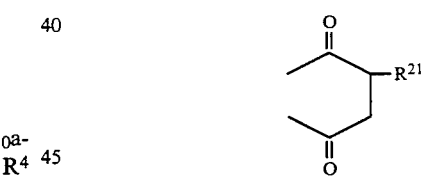

in which R$^{21}$ is C$_1$-C$_{18}$alkyl, R$^{14}$ is C$_1$-C$_{18}$alkyl, C$_5$-C$_8$cycloalkyl or C$_7$-C$_9$phenylalkyl or both groups R$^{14}$ together are C$_2$-C$_6$alkylene, o-phenylene or o-xylylene, R$^{15}$ is hydrogen, C$_1$-C$_{12}$alkyl, C$_3$-C$_5$alkenyl, C$_7$-C$_9$phenylalkyl, C$_2$-C$_4$hydroxyalkyl, C$_3$-C$_8$alkoxyalkyl or C$_3$-C$_{14}$alkoxycarbonylalkyl, R$^{16}$ is hydrogen, C$_1$-C$_{12}$alkyl, allyl or benzyl, R$^{18}$ is C$_1$-C$_{18}$alkyl, C$_2$-C$_6$alkenyl, C$_5$-C$_8$cycloalkyl, C$_7$-C$_9$phenylalkyl, phenyl or phenyl which is substituted by halogen, nitro, C$_1$-C$_4$alkyl, hydroxyl or C$_1$-C$_4$alkoxy or C$_7$-C$_9$phenylalkyl which is substituted by hydroxyl and C$_1$-C$_4$alkyl, R$^{19}$ is a s defined for R$^1$, R$^{20}$ is Cl, —OH, —OR$^3$, —SR$^3$ or —NR$^4$R$^5$, R$^{23}$ is C$_1$-C$_{12}$alkylene, vinylene, cyclohexylene, xylylene, C$_6$-C$_{12}$arylene or phenylene which is substituted by halogen, nitro or C$_1$-C$_4$alkyl, or a direct bond and An is a C$_2$-C$_4$alkylene group.

5. A 2,2,6,6tetramethyl-1-piperidyl-triazinyl compound of the formula VI

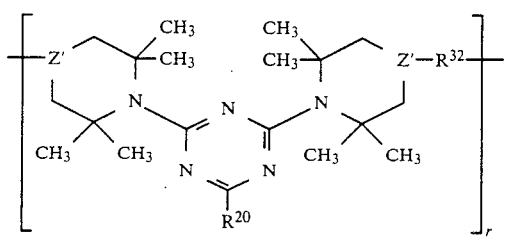 VI in which r has a value from 3 to 50, $R^{20}$ is Cl, —OH, —$OR^3$, $SR^3$ or $NR^4R^5$, where $R^3$ is $C_1$-$C_{18}$alkyl, allyl, cyclohexyl, benzyl, phenyl or a group of the formula A

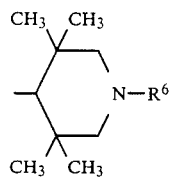 A $R^4$ is hydrogen, $C_1$-$C_{12}$alkyl, 2-hydroxyethyl, allyl, cyclohexyl, benzyl or a group of the formula A, $R^5$ is $C_1$-$C_{12}$alkyl, 2-hydroxyethyl, allyl, cyclohexyl, benzyl, phenyl, phenyl which is substituted by halogen, $C_1$-$C_4$alkyl or $C_1$-$C_4$alkoxy, a group of the formula A or a group of the formula C

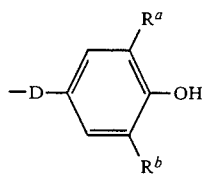 C in which D is $C_2$-$C_{20}$alkylene interrupted by

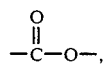

$R^a$ and $R^b$ are $C_1$-$C_{12}$alkyl, $C_5$-$C_6$cycloalkyl, $C_6$-$C_{10}$aryl or $C_7$-$C_9$phenylalkyl and $R^a$ is also hydrogen, or $R^4$ and $R^5$ together are $C_4$-$C_8$alkylene which may optionally be interrupted by —O— or —N($R^8$)— and in which $R^8$ is hydrogen, $C_1$-$C_4$alkyl or acetyl, $R^6$ is hydrogen, $C_1$-$C_{12}$alkyl, $C_7$-$C_9$phenylalkyl, $C_3$-$C_5$alkenyl, $C_2$-$C_4$alkanoyl, $C_3$-$C_5$alkenoyl, —O, —OH or —$OR^7$ and $R^7$ is $C_1$-$C_{18}$alkyl, $C_5$-$C_8$cycloalkyl, $C_7$-$C_9$phenylalkyl, phenyl, $C_2$-$C_{18}$alkanoyl or benzoyl, and

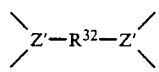

is one of the following groups

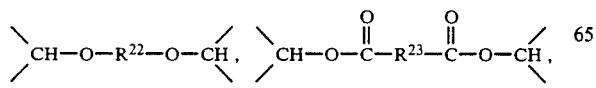

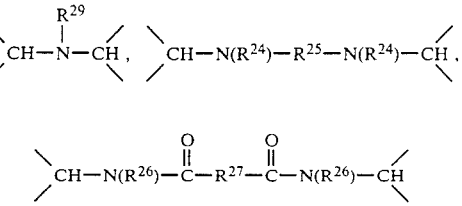

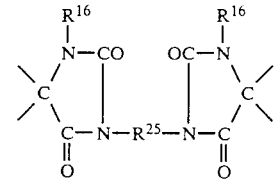

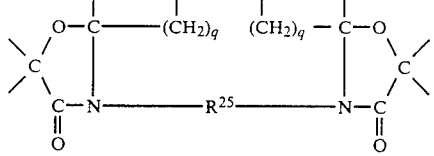

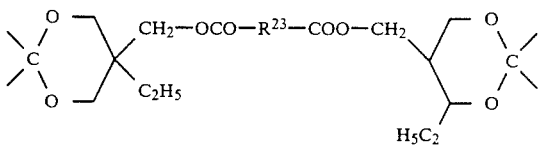

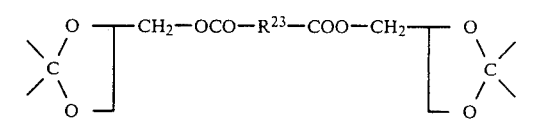

in which q is an integer from 5-11, $R^{16}$ is hydrogen, $C_1$-$C_{12}$alkyl, allyl or benzyl, $R^{22}$ is $C_2$-$C_{12}$alkylene, $C_4$-$C_8$alkenylene, xylylene or —CO—, $R^{23}$ is $C_1$-$C_{12}$alkylene, vinylene, cyclohexylene, xylylene, $C_6$-$C_{12}$arylene or phenylene which is substituted by halogen, nitro or $C_1$-$C_4$alkyl, or a direct bond, $R^{24}$ is hydrogen, $C_1$-$C_{12}$alkyl, $C_5$-$C_8$cycloalkyl, $C_7$-$C_9$phenylalkyl, $C_3$-$C_7$alkenyl, $C_2$-$C_{18}$alkanoyl, $C_3$-$C_7$alkenoyl, or benzoyl, $R^{25}$ is $C_2$-$C_{12}$alkylene, $C_4$-$C_{16}$alkylene which is interrupted by NH or O, $C_4$-$C_8$alkenylene, xylylene or cyclohexylene, $R^{26}$ is hydrogen, $C_1$-$C_{12}$alkyl, $C_5$-$C_8$cycloalkyl or a group of the formula A, $R^{27}$ is as defined for $R^{23}$ or is a group —NH—$R^{28}$—NH—, $R^{28}$ is $C_2$-$C_{12}$alkylene or $C_6$-$C_{12}$arylene which may optionally be substituted by $C_1$-$C_4$alkyl, $R^{29}$ is hydrogen, $C_1$-$C_{12}$alkyl, $C_2$-$C_{18}$alkanoyl or a triazinyl radical of the formula B

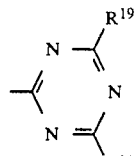 B $R^{19}$ is a radical of the formula

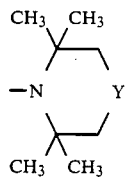

or Cl, OH, —OR$^3$, —SR$^3$ or —NR$^4$R$^5$ and Y is a group

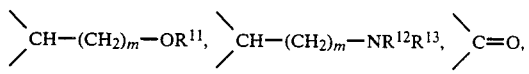

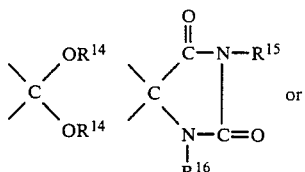

or

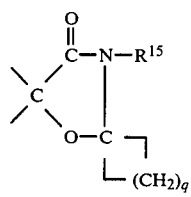

in which m is 0, 1 or 2, R$^{11}$ is hydrogen, C$_1$-C$_{18}$alkyl, C$_3$-C$_7$alkenyl, C$_5$-C$_8$cycloalkyl, C$_7$-C$_{11}$aralkyl or a group —CO—R$^{18}$, R$^{12}$ is hydrogen, C$_1$-C$_{12}$alkyl, C$_3$-C$_7$alkenyl, C$_5$-C$_8$cycloalkyl, C$_7$-C$_{11}$aralkyl, C$_2$-C$_4$-hydroxyalkyl, C$_3$-C$_8$alkoxyalkyl, C$_4$-C$_{20}$dialkylaminoalkyl, C$_3$-C$_{14}$alkoxycarbonylalkyl or a group of the formula A, R$^{13}$ is C$_1$-C$_{12}$alkyl, C$_2$-C$_4$hydroxyalkyl, C$_3$-C$_7$alkenyl, C$_5$-C$_8$cycloalkyl, phenyl, phenyl which is substituted by halogen, C$_1$-C$_4$alkyl or C$_1$-C$_4$alkoxy, C$_2$-C$_{20}$alkanoyl, C$_3$-C$_8$alkenoyl, benzoyl, phenylacetyl or a triazinyl radical of the formula B or R$^{12}$ and R$^{13}$ together are C$_4$-C$_8$alkylene which may optionally be interrupted by —O— or —N(R$^8$)— or R$^{12}$ and R$^{13}$ together are a radical of the formula

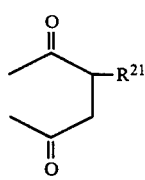

in which R$^{21}$ is C$_1$-C$_{18}$alkyl, R$^{14}$ is C$_1$-C$_{18}$alkyl, C$_5$-C$_8$cycloalkyl or C$_7$-C$_9$phenylalkyl or both groups R$^{14}$ together are C$_2$-C$_6$alkylene, o-phenylene or o-xylylene, R$^{15}$ is hydrogen, C$_1$-C$_{12}$alkyl, C$_3$-C$_5$alkenyl, C$_7$-C$_9$-phenylalkyl, C$_2$-C$_4$hydroxyalkyl, C$_3$-C$_8$alkoxyalkyl or C$_3$-C$_{14}$alkoxycarbonylalkyl, R$^{18}$ is C$_1$-C$_{18}$alkyl, C$_2$-C$_6$alkenyl, C$_5$-C$_8$cycloalkyl, C$_7$-C$_9$phenylalkyl, phenyl or phenyl which is substituted by halogen, nitro, C$_1$-C$_4$alkyl, hydroxyl or C$_1$-C$_4$alkoxy or C$_7$-C$_9$phenylalkyl which is substituted by hydroxyl and C$_1$-C$_4$alkyl.

6. A 2,2,6,6-tetramethyl-1-piperidyl-triazinyl compound of the formula VII

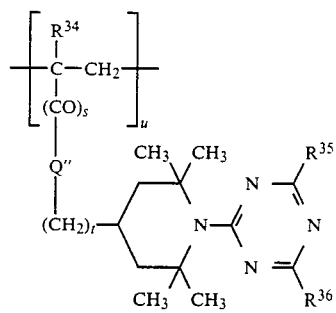

in which s is 0 or 1, t is 0 or 2 and u has a value from 5 to 100, Q" is —O—, —NH— or —N(C$_1$-C$_4$alkyl)-, R$^{34}$ is hydrogen or methyl, R$^{35}$ and R$^{36}$ independently of one another are —OY$^3$, —SR$^3$ or —NR$^4$R$^5$, where R$^3$ is C$_1$-C$_{18}$alkyl, allyl, cyclohexyl, benzyl, phenyl or a group of the formula A

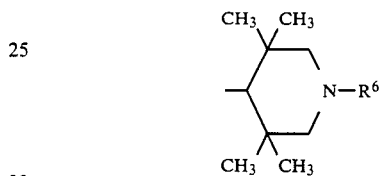

R$^4$ is hydrogen, C$_1$-C$_{12}$alkyl, 2-hydroxyethyl, allyl, cyclohexyl, benzyl or a group of the formula A, R$^5$ is C$_1$-C$_{12}$alkyl, 2-hydroxyethyl, allyl, cyclohexyl, benzyl, phenyl, phenyl which is substituted by halogen, C$_1$-C$_4$alkyl or C$_1$-C$_4$alkoxy, a group of the formula A or a group of the formula C

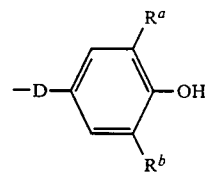

in which D is C$_2$-C$_{20}$alkylene interrupted by

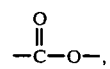

R$^a$ and R$^b$ are C$_1$-C$_{12}$alkyl, C$_5$-C$_6$cycloalkyl, C$_6$-C$_{10}$aryl or C$_7$-C$_9$phenylalkyl and R$^a$ is also hydrogen, or R$^4$ and R$^5$ together are C$_4$-C$_8$alkylene which may optionally be interrupted by —O— or —N(R$^8$)— and in which R$^8$ is hydrogen, C$_1$-C$_4$alkyl or acetyl, R$^6$ is hydrogen, C$_1$-C$_{12}$alkyl, C$_7$-C$_9$phenylalkyl, C$_3$-C$_5$alkenyl, C$_2$-C$_4$alkanoyl, C$_3$-C$_5$alkenoyl, —O, —OH or —OR$^7$ and R$^7$ is C$_1$-C$_{18}$alkyl, C$_5$-C$_8$cycloalkyl, C$_7$-C$_9$phenylalkyl, phenyl, C$_2$-C$_{18}$alkanoyl or benzoyl, and copolymers of such a compound with (meth)-acrylic acid, alkyl(meth)acrylates, hydroxyalkyl(meth)acrylates or maleic anhydride.

7. A 2,2,6,6-tetremethyl-1-piperidyl-triazinyl compound of the formula VIII

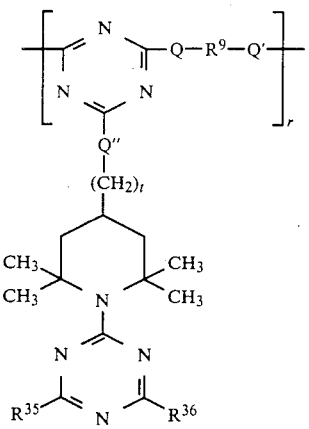

in which r has a value from 3 to 50, t is 0 or 2, Q is —O—, —S— or —N(R$^{10}$)—, where R$^9$ is C$_2$-C$_{20}$alkylene which may be optionally interrupted by one or more —O—, —N(R$^8$)— or —OOC—R$^{17}$—COO—, C$_4$-C$_8$alkenylene, C$_5$-C$_8$cycloalkylene, xylylene, phenylene or tolylene, R$^{10}$ is hydrogen, C$_1$-C$_{12}$alkyl, allyl, 2-hydroxyethyl, benzyl, phenyl or a group of the formula A

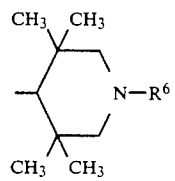

R$^8$ is hydrogen, C$_1$-C$_4$alkyl or acetyl, R$^{17}$ is C$_1$-C$_{12}$alkylene, vinylene, cyclohexylene, xylylene or C$_5$-C$_{12}$arylene, or in which —Q—R$^9$—Q'— is a group —NHNH—,

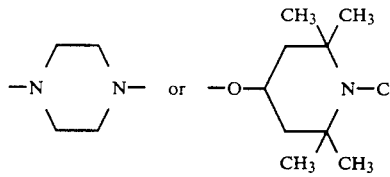

R$^{35}$ and R$^{36}$ independently of one another are —OR$^3$, —SR$^3$ or —NR$^4$R$^5$, where R$^3$ is C$_1$-C$_{18}$alkyl, allyl, cyclohexyl, benzyl, phenyl or a group of the formula A, R$^4$ is hydrogen, C$_1$-C$_{12}$alkyl, 2-hydroxyethyl, allyl, cyclohexyl, benzyl or a group of the formula A, R$^5$ is C$_1$-C$_{12}$alkyl, 2-hydroxyethyl, allyl, cyclohexyl, benzyl, phenyl, phenyl which is substituted by halogen, C$_1$-C$_4$alkyl or C$_1$-C$_4$alkoxy, a group of the formula A or a group of the formula C

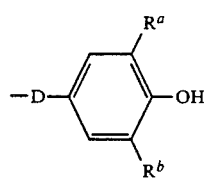

in which D is C$_2$-C$_{20}$alkylene interrupted by

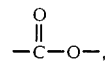

R$^a$ and R$^b$ are C$_1$-C$_{12}$alkyl, C$_5$-C$_6$cycloalkyl, C$_6$-C$_{10}$aryl or C$_7$-C$_9$phenylalkyl and R$^a$ is also hydrogen, or R$^4$ and R$^5$ together are C$_4$-C$_8$alkylene which may optionally be interrupted by —O— or —N(R$^8$)—, R$^6$ is hydrogen, C$_1$-C$_{12}$alkyl, C$_7$-C$_9$phenylalkyl, C$_3$-C$_5$alkenyl, C$_2$-C$_4$alkanoyl, C$_3$-C$_5$alkenoyl, —O, —OH or —OR$^7$ and R$^7$ is C$_1$-C$_{18}$alkyl, C$_5$-C$_8$cycloalkyl, C$_7$-C$_9$phenylalkyl, phenyl, C$_2$-C$_{18}$alkanoyl or benzoyl, and Q'' is —O—, —NH—, or —N(C$_1$-C$_4$alkyl)—.

8. A 2,2,6,6-tetramethyl-1-piperidyl-triazinyl compound of the formula IX

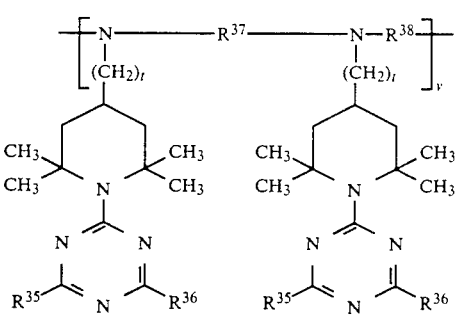

in which v has a value from 2 to 30, t is 1 or 2, R$^{35}$ and R$^{36}$ independently of one another are —OR$^3$, —SR$^3$ or —NR$^4$R$^5$, where R$^3$ is C$_1$-C$_{18}$alkyl, allyl, cyclohexyl, benzyl, phenyl or a group of the formula A

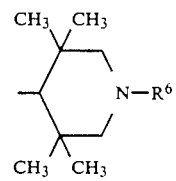

R$^4$ is hydrogen, C$_1$-C$_{12}$alkyl, 2-hydroxyethyl, allyl, cyclohexyl, benzyl or a group of the formula A, R$^5$ is C$_1$-C$_{12}$alkyl, 2-hydroxyethyl, allyl, cyclohexyl, benzyl, phenyl, phenyl which is substituted by halogen, C$_1$-C$_4$alkyl or C$_1$-C$_4$alkoxy, a group of the formula A or a group of the formula C

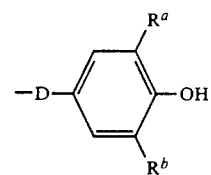

in which D is C$_2$-C$_{20}$alkylene interrupted by

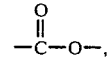

R$^a$ and R$^b$ are C$_1$-C$_{12}$alkyl, C$_5$-C$_6$cycloalkyl, C$_6$-C$_{10}$aryl or C$_7$-C$_9$phenylalkyl and R$^a$ is also hydrogen, or R$^4$ and R$^5$ together are C$_4$-C$_8$alkylene which may optionally be interrupted by —O— or —N(R$^8$)— in which R$^8$ is hydrogen, $C_1-C_4$alkyl or acetyl, $R^6$ is hydrogen, $C_1-C_{12}$alkyl, $C_7-C_9$phenylalkyl, $C_3-C_5$alkenyl, $C_2-C_4$alkanoyl, $C_3-C_5$alkenoyl, —O, —OH or —OR$^7$ and $R^7$ is $C_1-C_{18}$alkyl, $C_5-C_8$cycloalkyl, $C_7-C_9$phenylalkyl, phenyl, $C_2-C_{18}$alkanoyl or benzoyl, $R^{37}$ is $C_2-C_8$alkylene, $C_4-C_8$alkenylene, xylylene, —CH$_2$—CH(OH)—CH$_2$— or —CH$_2$CH(OH)CH$_2$—O—R$^{39}$—O—CH$_2$CH(CH)CH$_2$—, $R^{38}$ is as defined for $R^{37}$ or is

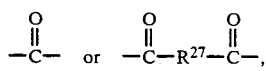

$R^{39}$ is $C_2-C_8$alkylene, phenylene or

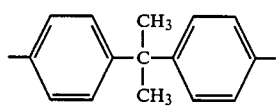

and $R^{27}$ is $C_1-C_{12}$alkylene, vinylene, cyclohexylene, xylylene, $C_6-C_{12}$arylene or phenylene which is substituted by halogen, nitro or $C_1-C_4$alkyl, a direct bond or is a group —NH—R$^{28}$—NH—, $R^{28}$ is $C_2-C_{12}$alkylene or $C_6-C_{12}$arylene which may optionally be substituted by $C_1-C_4$alkyl.

9. A 2,2,6,6-tetramethyl-1-piperidyl-triazinyl compound of the formula X

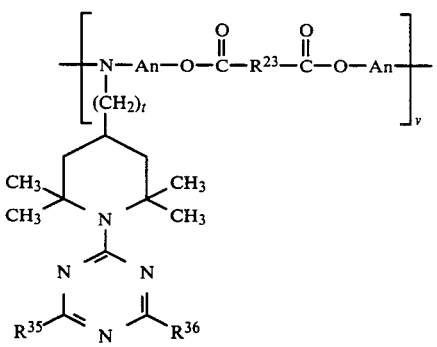

in which t is 0 or 2, v has a value from 2–30, An is $C_2-C_4$alkylene, $R^{23}$ is $C_1-C_{12}$alkylene, vinylene, cyclohexylene, xylylene, $C_6-C_{12}$arylene or phenylene which is substituted by halogen nitro or $C_1-C_4$alkyl, or a direct bond, and $R^{35}$ and $R^{36}$ independently of one another are —OR$^3$, —SR$^3$ or —NR$^4$R$^5$, where $R^3$ is $C_1-C_{18}$alkyl, allyl, cyclohexyl, benzyl, phenyl or a group of the formula A

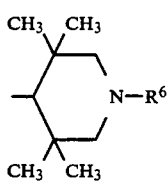

$R^4$ is hydrogen, $C_1-C_{12}$alkyl, 2-hydroxyethyl, allyl, cyclohexyl, benzyl or a group of the formula A, $R^5$ is $C_1-C_{12}$alkyl, 2-hydroxyethyl, allyl, cyclohexyl, benzyl, phenyl, phenyl which is substituted by halogen, $C_1-C_4$alkyl or $C_1-C_4$alkoxy, a group of the formula A or a group of the formula C

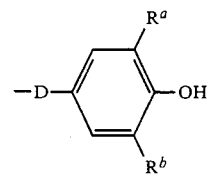

in which D is $C_2-C_{20}$alkylene interrupted by $$-\overset{O}{\underset{\|}{C}}-O-,$$

$R^a$ and $R^b$ are $C_1-C_{12}$alkyl, $C_5-C_6$cycloalkyl, $C_6-C_{10}$aryl or $C_7-C_9$phenylalkyl and $R^a$ is also hydrogen, or $R^4$ and $R^5$ together are $C_4-C_8$alkylene which may optionally be interrupted by —O— or —N(R$^8$)— and in which $R^8$ is hydrogen, $C_1-C_4$alkyl or acetyl, $R^6$ is hydrogen, $C_1-C_{12}$alkyl, $C_7-C_9$phenylalkyl, $C_3-C_5$alkenyl, $C_2-C_4$alkanoyl, $C_3-C_5$alkenoyl, —O, —OH or —OR$^7$ and $R^7$ is $C_1-C_{18}$alkyl, $C_5-C_8$cycloalkyl, $C_7-C_9$phenylalkyl, phenyl, $C_2-C_{18}$alkanoyl or benzoyl.

10. A 2,2,6,6-tetramethyl-1-piperidyl-triazinyl compound of the formula XI

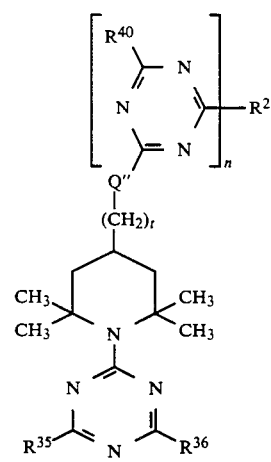

in which n is an integer from 1 to 6, t is 0 or 2, $R^{35}$ and $R^{36}$ independently of one another are —OR$^3$, —SR$^3$ or —NR$^4$R$^5$, where $R^3$ is $C_1-C_{18}$alkyl, allyl, cyclohexyl, benzyl, phenyl or a group of the formula A

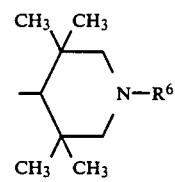

$R^4$ is hydrogen, $C_1-C_{12}$alkyl, 2-hydroxyethyl, allyl, cyclohexyl, benzyl or a group of the formula A, $R^5$ is $C_1-C_{12}$alkyl, 2-hydroxyethyl, allyl, cyclohexyl, benzyl, phenyl, phenyl which is substituted by halogen, $C_1-C_4$alkyl or $C_1-C_4$alkoxy, a group of the formula A or a group of the formula C

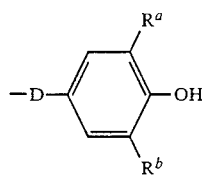

in which D is C$_2$-C$_{20}$alkylene interrupted by

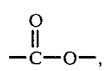

R$^a$ and R$^b$ are C$_1$-C$_{12}$alkyl, C$_5$-C$_6$cycloalkyl, C$_6$-C$_{10}$aryl or C$_7$-C$_9$phenylalkyl and R$^a$ is also hydrogen, or R$^4$ and R$^5$ together are C$_4$-C$_8$alkylene which may optionally be interrupted by —O— or —N(R$^8$)— and in which R$^8$ is hydrogen, C$_1$-C$_4$alkyl or acetyl, R$^6$ is hydrogen, C$_1$-C$_{12}$alkyl, C$_7$-C$_9$phenylalkyl, C$_3$-C$_5$alkenyl, C$_2$-C$_4$alkanoyl, C$_3$-C$_5$alkenoyl, —O, —OH or —OR$^7$ and R$^7$ is C$_1$-C$_{18}$alkyl, C$_5$-C$_8$cycloalkyl, C$_7$-C$_9$phenylalkyl, phenyl, C$_2$-C$_{18}$alkanoyl or benzoyl, and R$^{40}$ is a radical of the formula

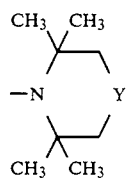

or Cl, OH, —OR$^3$, —SR$^3$, —NR$^4$R$^5$ or is a group

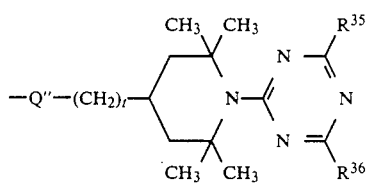

Y is a group

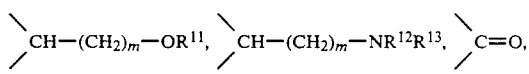

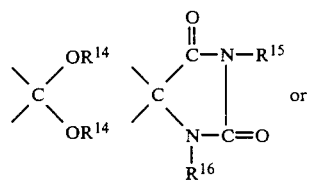

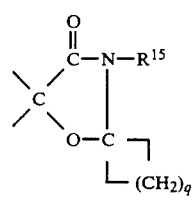

in which m is 0, 1 or 2, q is an integer from 5–11, R$^{11}$ is hydrogen, C$_1$-C$_{18}$alkyl, C$_3$-C$_7$alkenyl, C$_5$-C$_8$cycloalkyl, C$_7$-C$_{11}$aralkyl or a group —CO—R$^{18}$, R$^{12}$ is hydrogen, C$_1$-C$_{12}$alkyl, C$_3$-C$_7$alkenyl, C$_5$-C$_8$cycloalkyl, C$_7$-C$_{11}$aralkyl, C$_2$-C$_4$hydroxyalkyl, C$_3$-C$_8$alkoxyalkyl, C$_4$-C$_{20}$dialkylaminoalkyl, C$_3$-C$_{14}$alkoxycarbonylalkyl or a group of the formula A, R$^{13}$ is C$_1$-C$_{12}$alkyl, C$_2$-C$_4$hydroxyalkyl, C$_3$-C$_7$alkenyl, C$_5$-C$_8$cycloalkyl, phenyl, phenyl which is substituted by halogen, C$_1$-C$_4$alkyl or C$_1$-C$_4$alkoxy, C$_2$-C$_{20}$alkanoyl, C$_3$-C$_8$alkenoyl, benzoyl, phenylacetyl or a triazinyl radical of the formula B

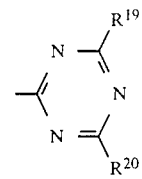

or R$^{12}$ and R$^{13}$ together are C$_4$-C$_8$alkylene which may optionally be interrupted by —O— or —N(R$^8$)— or R$^{12}$ and R$^{13}$ together are a radical of the formula

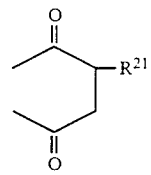

in which R$^{21}$ is C$_1$-C$_{18}$alkyl, R$^{14}$ is C$_1$-C$_{18}$alkyl, C$_5$-C$_8$cycloalkyl or C$_7$-C$_9$phenylalkyl or both groups R$^{14}$ together are C$_2$-C$_6$alkylene, o-phenylene or o-xylylene, R$^{15}$ is hydrogen, C$_1$-C$_{12}$alkyl, C$_3$-C$_5$alkenyl, C$_7$-C$_9$phenylalkyl, C$_2$-C$_4$hydroxyalkyl, C$_3$-C$_8$alkoxyalkyl or C$_3$-C$_{14}$alkoxycarbonylalkyl, R$^{16}$ is hydrogen, C$_1$-C$_{12}$alkyl, allyl or benzyl, R$^{17}$ is C$_1$-C$_{12}$alkylene, vinylene, cyclohexylene, xylylene or C$_6$-C$_{12}$arylene, R$^{18}$ is C$_1$-C$_{18}$alkyl, C$_2$-C$_6$alkenyl, C$_5$-C$_8$cycloalkyl, C$_7$-C$_9$phenylalkyl, phenyl or phenyl which is substituted by halogen, nitro, C$_1$-C$_4$alkyl, hydroxyl or C$_1$-C$_4$alkoxy or C$_7$-C$_9$phenylalkyl which is substituted by hydroxyl and C$_1$-C$_4$alkyl, R$^{19}$ is a radical of the formula

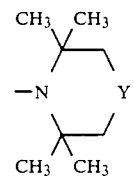

or Cl, OH, —OR$^3$, —SR$^3$ or —NR$^4$R$^5$, R$^{20}$ is Cl, —OH, —OR$^3$, —SR$^3$ or —NR$^4$R$^5$, if n=1, R$^2$ is Cl, OH, —OR$^3$, —SR$^3$ or —NR$^4$R$^5$, if n=2, R$^2$ is a group —O—R$^9$—O—, —S—R$^9$—S—, —N(R$^{10}$)—R$^9$—N(R$^{10}$)—, —O—R$^9$—N(R$^{10}$)—,

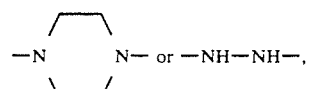

where R$^9$ is C$_2$-C$_{20}$alkylene which may optionally be interrupted by one or more —O—, —N(R$^8$)— or —OOC—R$^{17}$—COO—, C$_4$-C$_8$alkenylene, C$_5$-C$_8$cycloalkylene, xylylene, phenylene or tolylene, R$^{10}$ is hydrogen, $C_1$-$C_{12}$alkyl, allyl, 2-hydroxyethyl, benzyl, phenyl or a group of the formula A, if n=3, $R^2$ is a group

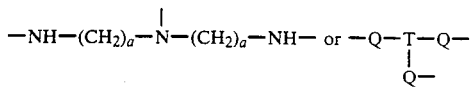

in which a is 2 or 3, Q is —O—, —S— or —N($R^{10}$)— and T is $C_3$-$C_{20}$alkanetriyl or a group

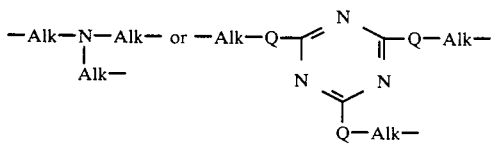

in which Alk is a $C_2$-$C_{12}$alkylene group, if n=4, $R^2$ is a group $C(CH_2O—)_4$ or

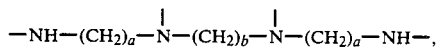

in which a is 2 or 3 and b is 2-12, if n=5, $R^2$ is a group

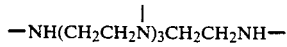

and if n=6, $R^2$ is a group

—NH(CH$_2$CH$_2$N)$_4$CH$_2$CH$_2$NH— and Q'' is —O—, —NH— or —N($C_1$-$C_4$alkyl).

11. A compound according to claim 1 of the formula II, in which n is an integer from 1-4, $R^1$ is a radical Cl, —OR$^3$ or —NR$^4$R$^5$, $R^2$, if n=1, is Cl, —OR$^3$ or —NR$^4$R$^5$, if n=2, $R^2$ is a group —N($R^{10}$)—$R^9$—N($R^{10}$)— or

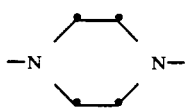

if n=3, $R^2$ is a group

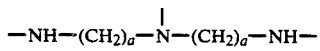

and if n=4, $R^2$ is a group

in which a is 2 or 3 and b is 2 to 8 and Y is a group

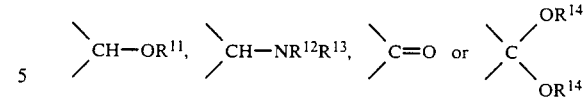

12. A compound according to claim 1 of the formula II, in which n is 1 or 2, $R^1$ is a radical of the formula

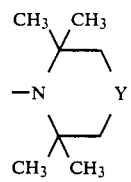

or Cl, —OR$^3$ or NR$^4$R$^5$, where R$^3$ is $C_1$-$C_{12}$alkyl, allyl or a group o the formula A, R$^4$ is hydrogen, $C_1$-$C_8$alkyl, 2-hydroxyalkyl or a group of the formula A, R$^5$ is $C_1$-$C_8$alkyl, 2-hydroxyethyl, a group of the formula A or a group of the formula

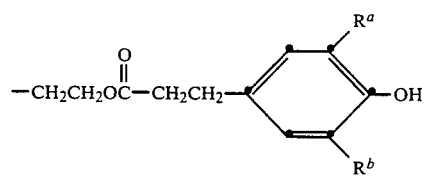

in which R$^a$ and R$^b$ are $C_1$-$C_4$alkyl, or R$^4$ and R$^5$ together are 3-oxapentamethylene, R$^2$, with n=1, is Cl, —OR$^3$ or —NR$^4$R$^5$, and with n=2, is —NH(CH$_2$)$_6$—NH—, Y is one of the groups

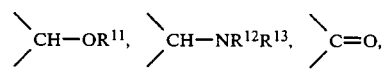

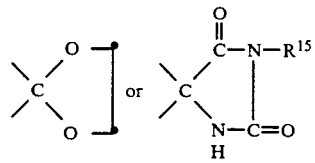

in which R$^{11}$ is hydrogen, $C_1$-$C_6$alkyl, acetyl, acryloyl, benzyl or a group of the formula

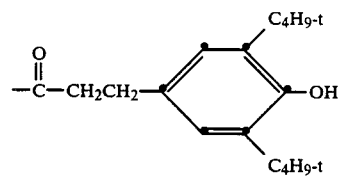

R$^{12}$ is hydrogen or $C_1$-$C_4$alkyl, R$^{13}$ is $C_1$-$C_4$alkyl or a radical of the formula B in which R$^{19}$ and R$^{20}$ are Cl or —NR$^4$R$^5$, and R$^{15}$ is $C_1$-$C_{12}$alkyl.

13. A compound according to claim 2 of the formula III, in which p is 2, R$^{19}$ and R$^{20}$ are Cl or —NR$^4$R$^5$, in which R$^4$ and R$^5$ are $C_1$-$C_4$alkyl, and Z is one of the groups

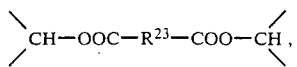

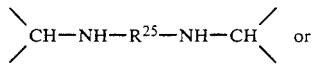

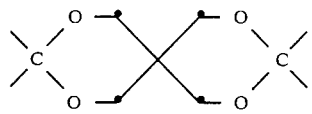

in which $R^{23}$ is $C_2-C_8$alkylene or phenylene and $R^{25}$ is —(CH$_2$)$_6$—.

14. A compound according to claim 3 of the formula IV, in which r has a value from 3 to 25, Q and Q' are —O— or —N(R$^{10}$)—.

15. A compound according to claim 3 of the formula IV in which r has a value from 3 to 50, Y is a group

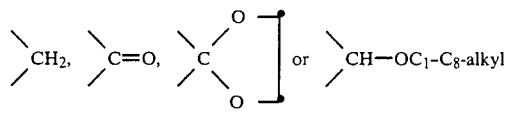

Q and Q' are —NH— and $R^9$ is —(CH$_2$)$_6$—.

16. A compound according to claim 4 of the formula V, in which r has a value from 3 to 50, Y is a group of the formula

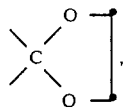

An is —CH$_2$CH$_2$— and $R^{23}$ is $C_2-C_8$alkylene.

17. A compound according to claim 2 of the formula III, in which p is 2, 3 or 4, and $R^{19}$ and $R^{20}$ independently of one another are —OR$^3$ or NR$^4$R$^5$, where R$^3$ is $C_1-C_{18}$alkyl, allyl, cyclohexyl, benzyl, phenyl or a group of the formula A

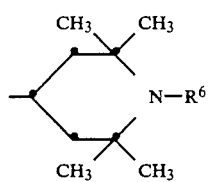

$R^4$ is hydrogen, $C_1-C_{12}$alkyl, 2-hydroxyethyl, allyl, cyclohexyl, benzyl or a group of the formula A, $R^5$ is $C_1-C_{12}$alkyl, 2-hydroxyethyl, allyl, cyclohexyl, benzyl, phenyl, phenyl which is substituted by halogen, $C_1-C_4$alkyl or $C_1-C_4$alkoxy, a group of the formula A or a group of the formula C

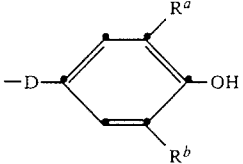

in which D is $C_2-C_{20}$alkylene interrupted by

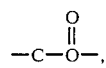

$R^a$ and $R^b$ are $C_1-C_{12}$alkyl, $C_5-C_6$cycloalkyl, $C_6-C_{10}$aryl or $C_7-C_9$phenylalkyl and $R^a$ is also hydrogen, or $R^4$ and $R^5$ together are $C_4-C_8$alkylene which can be interrupted by —O— or —N(R$^8$)— and in which $R^8$ is hydrogen, $C_1-C_4$alkyl or acetyl, $R^6$ is hydrogen, $C_1-C_{12}$alkyl, $C_7-C_9$phenylalkyl, $C_3-C_5$alkenyl, $C_2-C_4$alkanoyl, $C_3-C_5$alkenoyl, —O, —OH or —OR$^7$ and $R^7$ is $C_1-C_{18}$alkyl, $C_5-C_8$cycloalkyl, $C_7-C_9$phenylalkyl, phenyl, $C_2-C_{18}$alkanoyl or benzoyl, Z, if p=2, is one of the groups

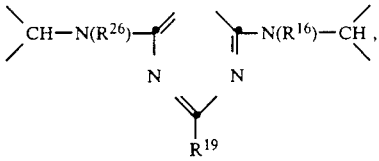

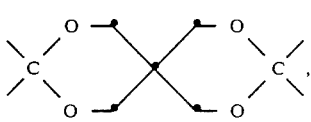

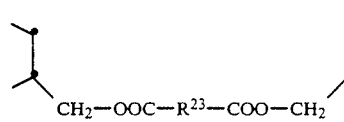

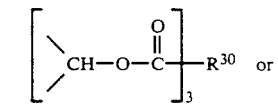

wherein p=3, Z is one of the groups

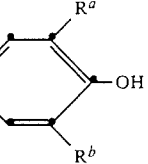

-continued

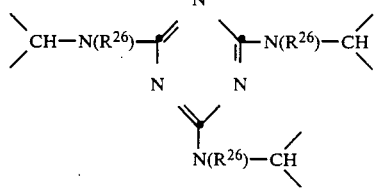

in which $R^{30}$ is $C_3$-$C_8$alkanetriyl or $C_6$-$C_{12}$arenetriyl, and if p=4, Z is a group

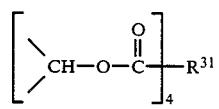

in which $R^{31}$ is $C_4$-$C_{12}$alkane.

18. A 2,2,6,6-tetramethyl-1-piperidyl-triazinyl compound of the formula XIII

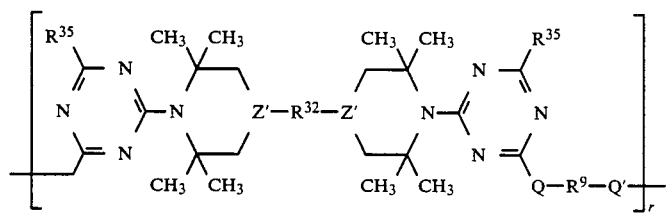

in which r has a value from 3 to 50, $R^9$ is $C_2$-$C_{20}$alkylene which may optionally be interrupted by one or more —O—, —N($R^8$)— or —OOC—$R^{17}$—COO—, $C_4$-$C_8$alkenylene, $C_5$-$C_8$cycloalkylene, xylylene, phenylene or tolylene, $R^8$ is hydrogen, $C_1$-$C_4$alkyl or acetyl, $R^{17}$ is $C_1$-$C_{12}$alkylene, vinylene, cyclohexylene, xylylene or $C_6$-$C_{12}$arylene,

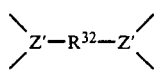

is one of the following groups

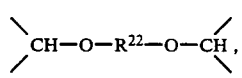

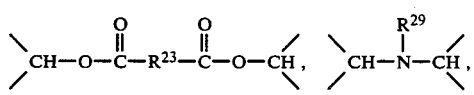

in which q is an integer from 5-11, $R^{16}$ is hydrogen, $C_1$-$C_{12}$alkyl, allyl or benzyl, $R^{22}$ is $C_2$-$C_{12}$alkylene, $C_4$-$C_8$alkenylene, xylylene or —CO—, $R^{23}$ is $C_1$-$C_{12}$alkylene, vinylene, cyclohexylene, xylylene, $C_6$-$C_{12}$arylene or phenylene which is substituted by halogen, nitro or $C_1$-$C_4$alkyl, or a direct bond, $R^{24}$ is hydrogen, $C_1$-$C_{12}$alkyl, $C_5$-$C_8$cycloalkyl, $C_7$-$C_9$phenylalkyl, $C_3$-$C_7$alkenyl, $C_2$-$C_{18}$alkanoyl, $C_3$-$C_7$alkenoyl, or benzoyl, $R^{25}$ is $C_2$-$C_{12}$alkylene, $C_4$-$C_{16}$alkylene which is interrupted by NH or O, $C_4$-$C_8$alkenylene, xylylene or cyclohexylene, $R^{26}$ is hydrogen, $C_1$-$C_{12}$alkyl, $C_5$-$C_8$cycloalkyl or a group of the formula A

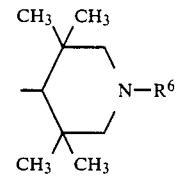

$R^{27}$ is as defined for $R^{23}$ or is a group —NH—$R^{28}$—NH—, $R^{28}$ is $C_2$-$C_{12}$alkylene or $C_6$-$C_{12}$arylene which may optionally be substituted by $C_1$-$C_4$alkyl, $R^{29}$ is hydrogen, $C_1$-$C_{12}$alkyl, $C_2$-$C_{18}$alkanoyl or a triazinyl radical of the formula B

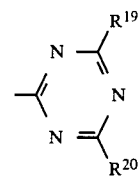

$R^{19}$ is a radical of the formula

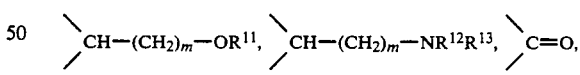

or Cl, OH, —$OR^3$, —$SR^3$ or —$NR^4R^5$, Y is a group

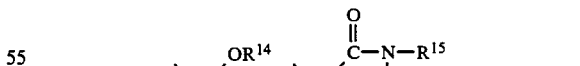

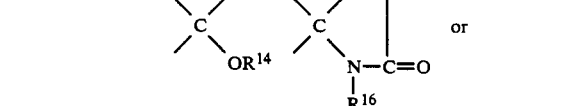

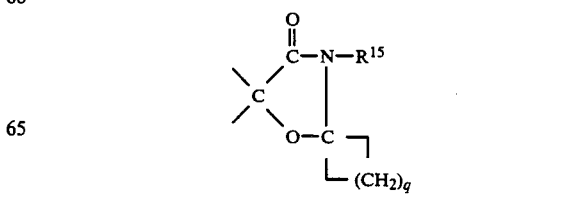

in which m is 0, 1 or 2, q is an integer from 5-11, $R^{11}$ is hydrogen, $C_1$-$C_{18}$alkyl, $C_3$-$C_7$alkenyl, $C_5$-$C_8$cycloalkyl, $C_7$-$C_{11}$aralkyl or a group —CO—$R^{18}$, $R^{12}$ is hydrogen, $C_1$-$C_{12}$alkyl, $C_3$-$C_7$alkenyl, $C_5$-$C_8$cycloalkyl, $C_7$-$C_{11}$aralkyl, $C_2$-$C_4$hydroxyalkyl, $C_3$-$C_8$alkoxyalkyl, $C_4$-$C_{20}$dialkylaminoalkyl, $C_3$-$C_{14}$alkoxycarbonylalkyl or a group of the formula A, $R^{13}$ is $C_1$-$C_{12}$alkyl, $C_2$-$C_4$hydroxyalkyl, $C_3$-$C_7$alkenyl, $C_5$-$C_8$cycloalkyl, phenyl, phenyl which is substituted by halogen, $C_1$-$C_4$alkyl or $C_1$-$C_4$alkoxy, $C_2$-$C_{20}$alkanoyl, $C_3$-$C_8$alkenoyl, benzoyl, phenylacetyl or a triazinyl radical of the formula B, or $R^{12}$ and $R^{13}$ together are $C_4$-$C_8$alkylene which may optionally be interrupted by —O— or —N($R^8$)— or $R^{12}$ and $R^{13}$ together are a radical of the formula

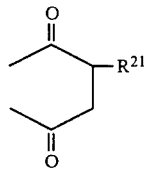

in which $R^{21}$ is $C_1$-$C_{18}$alkyl, $R^{14}$ is $C_1$-$C_{18}$alkyl, $C_5$-$C_8$cycloalkyl or $C_7$-$C_9$phenylalkyl or both groups $R^{14}$ together are $C_2$-$C_6$alkylene, o-phenylene or o-xylylene, $R^{15}$ is hydrogen, $C_1$-$C_{12}$alkyl, $C_3$-$C_5$alkenyl, $C_7$-$C_9$phenylalkyl, $C_2$-$C_4$hydroxyalkyl, $C_3$-$C_8$alkoxyalkyl or $C_3$-$C_{14}$alkoxycarbonylalkyl, $R^{18}$ is $C_1$-$C_{18}$alkyl, $C_2$-$C_6$alkenyl, $C_5$-$C_8$cycloalkyl, $C_7$-$C_9$phenylalkyl, phenyl or phenyl which is substituted by halogen, nitro, $C_1$-$C_4$alkyl, hydroxyl or $C_1$-$C_4$alkoxy or $C_7$-$C_9$phenylalkyl which is substituted by hydroxyl and $C_1$-$C_4$alkyl, $R^{20}$ is Cl, —OH, —$OR^3$, —$SR^3$ or —$NR^4R^5$, $R^{35}$ is —$OR^3$, —$SR^3$ or —$NR^4R^5$, where $R^3$ is $C_1$-$C_{18}$alkyl, allyl, cyclohexyl, benzyl, phenyl or a group of the formula A, $R^4$ is hydrogen, $C_1$-$C_{12}$alkyl, 2-hydroxyethyl, allyl, cyclohexyl, benzyl or a group of the formula A, $R^5$ is $C_1$-$C_{12}$alkyl, 2-hydroxyethyl, allyl, cyclohexyl, benzyl, phenyl, phenyl which is substituted by halogen, $C_1$-$C_4$alkyl or $C_1$-$C_4$alkoxy, a group of the formula A or a group of the formula C

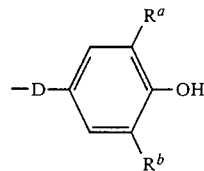

in which D is $C_2$-$C_{20}$alkylene interrupted by

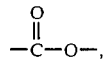

$R^a$ and $R^b$ are $C_1$-$C_{12}$alkyl, $C_5$-$C_6$cycloalkyl, $C_6$-$C_{10}$aryl or $C_7$-$C_9$phenylalkyl and $R^a$ is also hydrogen, or $R^4$ and $R^5$ together are $C_4$-$C_8$alkylene which may optionally be interrupted by —O— or —N($R^9$)— and in which $R^8$ is hydrogen, $C_1$-$C_4$alkyl or acetyl, $R^6$ is hydrogen, $C_1$-$C_{12}$alkyl, $C_7$-$C_9$phenylalkyl, $C_3$-$C_5$alkenyl, $C_2$-$C_4$alkanoyl, $C_3$-$C_5$alkenoyl, —O, —OH or —$OR^7$ and $R^7$ is $C_1$-$C_{18}$alkyl, $C_5$-$C_8$cycloalkyl, $C_7$-$C_9$phenylalkyl, phenyl, $C_2$-$C_{18}$alkanoyl or benzoyl, and Q and Q' independently of one another are —O—, —S— or —N($R^{10}$)—, wherein $R^{10}$ is hydrogen, $C_1$-$C_{12}$alkyl, allyl, 2-hydroxyethyl, benzyl, phenyl or a group of the formula A.

* * * * *